US011952426B2

(12) United States Patent
Adams et al.

(10) Patent No.: US 11,952,426 B2
(45) Date of Patent: Apr. 9, 2024

(54) METHODS FOR TREATING MULTIPLE MYELOMA

(71) Applicant: Janssen Biotech Inc., Horsham, PA (US)

(72) Inventors: Homer Adams, Glenside, PA (US); Arnob Banerjee, Baltimore, MD (US); Suzette Girgis, Spring House, PA (US); Jenna Goldberg, Spring House, PA (US); Tara Stephenson, Spring House, PA (US); Raluca Verona, Spring House, PA (US); Shun xin Wang lin, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 17/317,789

(22) Filed: May 11, 2021

(65) Prior Publication Data
US 2022/0041742 A1 Feb. 10, 2022

Related U.S. Application Data

(60) Provisional application No. 63/159,303, filed on Mar. 10, 2021, provisional application No. 63/024,209, filed on May 13, 2020, provisional application No. 63/023,092, filed on May 11, 2020.

(51) Int. Cl.
*C07K 16/28* (2006.01)
*A61K 39/395* (2006.01)
*A61K 45/06* (2006.01)
*A61P 35/00* (2006.01)
*C07K 16/46* (2006.01)
*A61K 39/00* (2006.01)

(52) U.S. Cl.
CPC ...... *C07K 16/2878* (2013.01); *A61K 39/3955* (2013.01); *A61K 39/39558* (2013.01); *A61K 45/06* (2013.01); *A61P 35/00* (2018.01); *C07K 16/2809* (2013.01); *C07K 16/468* (2013.01); *A61K 2039/505* (2013.01); *A61K 2039/507* (2013.01); *A61K 2039/545* (2013.01); *C07K 2317/31* (2013.01); *C07K 2317/56* (2013.01); *C07K 2317/73* (2013.01); *C07K 2317/76* (2013.01)

(58) Field of Classification Search
CPC ............ C07K 16/2878; C07K 16/2809; C07K 2317/31; C07K 16/468; C07K 16/2896; C07K 2317/56; C07K 2317/73; C07K 2317/76; A61P 35/00; A61K 2039/545; A61K 2039/507; A61K 2039/505; A61K 39/395; A61K 39/3955; A61K 39/39558
See application file for complete search history.

(56) References Cited

U.S. PATENT DOCUMENTS

| 6,521,427 | B1 | 2/2003 | Evans |
| 6,670,127 | B2 | 12/2003 | Evans |
| 6,737,056 | B1 | 5/2004 | Presta |
| 7,994,289 | B2 | 8/2011 | Waldmann et al. |
| 8,236,308 | B2 | 8/2012 | Kischel et al. |
| 10,072,088 | B2 | 9/2018 | Pillarisetti et al. |
| 2005/0276803 | A1 | 12/2005 | Chan et al. |
| 2009/0182127 | A1 | 7/2009 | Kjaergaard et al. |
| 2010/0015133 | A1 | 1/2010 | Igawa et al. |
| 2010/0028637 | A1 | 2/2010 | Tavsanli et al. |
| 2011/0123532 | A1 | 5/2011 | Gurney et al. |
| 2012/0149876 | A1 | 6/2012 | Von Kreudenstein et al. |
| 2013/0156769 | A1 | 6/2013 | Kufer et al. |
| 2013/0195849 | A1 | 8/2013 | Spreter Von Kreudenstein et al. |
| 2014/0154254 | A1 | 6/2014 | Kannan et al. |
| 2016/0297885 | A1* | 10/2016 | Kuo .................. A61K 47/6849 |
| 2017/0051068 | A1* | 2/2017 | Pillarisetti ............... A61P 35/02 |
| 2019/0263920 | A1 | 8/2019 | Vu et al. |
| 2019/0352421 | A1 | 11/2019 | Adams et al. |
| 2019/0367628 | A1 | 12/2019 | Abujoub et al. |
| 2020/0179511 | A1 | 6/2020 | Daley et al. |
| 2020/0190205 | A1 | 6/2020 | Adams et al. |
| 2020/0308284 | A1 | 10/2020 | Bandekar et al. |
| 2021/0128619 | A1 | 5/2021 | Campbell et al. |
| 2022/0373550 | A1 | 11/2022 | Pillarisetti et al. |
| 2022/0411525 | A1 | 12/2022 | Adams, III et al. |
| 2023/0272102 | A1* | 8/2023 | Goldberg ............... C07K 16/30 424/136.1 |

FOREIGN PATENT DOCUMENTS

| EP | 0999853 B1 | 1/2003 |
| EP | 2762497 A1 | 8/2014 |
| WO | 1988001649 A1 | 3/1988 |
| WO | 1992001047 A1 | 1/1992 |
| WO | 1994013804 A1 | 6/1994 |
| WO | 1998044001 A1 | 10/1998 |
| WO | 2000041474 A2 | 7/2000 |

(Continued)

OTHER PUBLICATIONS

Caraccio et al. ("Bispecific Antibodies for Multiple Myeloma: A Review of Targets, Drugs, Clinical Trials, and Future Directions"; Front. Immunol., Apr. 24, 2020 Sec. Cancer Immunity and Immunotherapy) (Year: 2020).*

(Continued)

*Primary Examiner* — Bridget E Bunner

(74) *Attorney, Agent, or Firm* — TROUTMAN PEPPER HAMILTON SANDERS LLP

(57) ABSTRACT

Methods of treating cancers using a BCMAxCD3 bispecific antibody are described.

13 Claims, 21 Drawing Sheets

Specification includes a Sequence Listing.

(56) References Cited

FOREIGN PATENT DOCUMENTS

| WO | 2001024811 A1 | 4/2001 |
|---|---|---|
| WO | 2001024812 A1 | 4/2001 |
| WO | 2002066516 A2 | 8/2002 |
| WO | 2006028936 A2 | 3/2006 |
| WO | 2007059782 A1 | 5/2007 |
| WO | 2007117600 A2 | 10/2007 |
| WO | 2008119565 A2 | 10/2008 |
| WO | 2008119566 A2 | 10/2008 |
| WO | 2008119567 A2 | 10/2008 |
| WO | 2009085462 A1 | 7/2009 |
| WO | 2009132058 A2 | 10/2009 |
| WO | 2010037836 A2 | 4/2010 |
| WO | 2010037837 A2 | 4/2010 |
| WO | 2010037838 A2 | 4/2010 |
| WO | 2010051274 A2 | 5/2010 |
| WO | 2010093627 A2 | 8/2010 |
| WO | 2010104949 A2 | 9/2010 |
| WO | 2011131746 A2 | 10/2011 |
| WO | 2012066058 A1 | 5/2012 |
| WO | 2012143498 A1 | 10/2012 |
| WO | 2012158818 A2 | 11/2012 |
| WO | 2012163805 A1 | 12/2012 |
| WO | 2013020074 A2 | 2/2013 |
| WO | 2013072406 A1 | 5/2013 |
| WO | 2013072415 A1 | 5/2013 |
| WO | 2013158856 A2 | 10/2013 |
| WO | 2014056783 A1 | 4/2014 |
| WO | 2014089335 A2 | 6/2014 |
| WO | 2014093908 A2 | 6/2014 |
| WO | 2014122143 A1 | 8/2014 |
| WO | 2014122144 A1 | 8/2014 |
| WO | 2014124143 A1 | 8/2014 |
| WO | 2014140248 A1 | 9/2014 |
| WO | 2014145806 A2 | 9/2014 |
| WO | 2015052536 A1 | 4/2015 |
| WO | 2016166629 A1 | 10/2016 |
| WO | 2018083204 A1 | 5/2018 |
| WO | 2019220368 A1 | 11/2019 |
| WO | 2020089794 A1 | 5/2020 |
| WO | 2020261093 A1 | 12/2020 |
| WO | 2021092060 A1 | 5/2021 |
| WO | 2021113701 A1 | 6/2021 |

OTHER PUBLICATIONS

Avet-Loiseau et al. ("Evaluation of Minimal Residual Disease (MRD) By Next Generation Sequencing (NGS) Is Highly Predictive of Progression Free Survival in the IFM/DFCI 2009 Trial", Blood, vol. 126, Issue 23, 2015, p. 191) (Year: 2015).*
Clinical Trial NCT03145181, version dated Apr. 25, 2019; Dose Escalation Study of Teclistamab, a Humanized BCMA*CD3 Bispecific Antibody, in Participants With Relapsed or Refractory Multiple Myeloma (MajesTEC-1) ; https://clinicaltrials.gov/study/NCT03145181?term=NCT03145181&rank=1&tab=history&a=17.*
Girgis et al. Exploratory Pharmacokinetic/Pharmacodynamic and Tolerability Study of BCMAxCD3 in Cynomolgus Monkeys. Blood 128(22): 5668, 2016.*
Shah et al. B-cell maturation antigen (BCMA) in multiple myeloma: rationale for targeting and current therapeutic approaches. Leukemia 34: 985-1005, Feb. 2020.*
Abhinandan et al., "Analysis and Improvements to Kabat and Structurally Correct Numbering of Antibody Variable Domains", Molecular Immunology (2008) vol. 45, pp. 3832-3839.
Adams et al., "Recent Developments in the PHENIX Software for Automated Crystallographic Structure Determination," J. Synchrotron Rad. (2004) vol. 11, pp. 53-55.
Anasetti et al., "Treatment of Acute Graft-Versus-Host Disease With a Nonmitogenic Anti-CD3 Monoclonal Antibody," Transplantation (Nov. 1992) vol. 54(5), pp. 844-851.

Babb et al., "Cancer Phase I Clinical Trials: Efficient Dose Escalation with Overdose Control," Stat. Med. (1998) vol. 17, pp. 1103-1120.
Baert et al., "Influence of Immunogenicity on the Long-Term Efficacy of Infliximab in Crohn's Disease," N. Engl. J. Med. (2003) vol. 348, pp. 601-608.
Beiboer et al., "Guided Selection of a Pan Carcinoma Specific Antibody Reveals Similar Binding Characteristics yet Structural Divergence Between the Original Murine Antibody and its Human Equivalent," J. Mol. Biol. (2000) vol. 296, pp. 833-849.
Brudno et al., "T Cells Genetically Modified to Express an Anti-B-Cell Maturation Antigen Chimeric Antigen Receptor Cause Remissions of Poor-Prognosis Relapsed Multiple Myeloma," Journal of Clinical Oncology (Aug. 1, 2018) vol. 36, No. 22, pp. 2267-2280.
Carpenter et al., "B-Cell Maturation Antigen is a Promising Target for Adoptive T-Cell Therapy of Multiple Myeloma," Clin. Cancer Res. (2013) vol. 19(8), pp. 2048-2060.
Casset et al., "A Peptide Mimetic of an Anti-CD4 Monoclonal Antibody by Rational Design," BBRC (2003) vol. 307, pp. 198-205.
Chames et al., "Bispecific Antibodies for Cancer Therapy," Current Opinion in Drug Discovery & Development (2009) vol. 12(2), pp. 276-283.
Chari et al., "Oral Selinexor-Dexamethasone for Triple-Class Refractory Multiple Myelomam" N. Engl. J. Med. (2019) vol. 381, pp. 727-738.
Chen, et al., "Thymoglobulin Efficiently Explands Cytokine-Induced Killer Cells in a Clinical-Grade Culture Protocol," Chin. J. Cell. Mol. Immunol., 30(7):681-690 (2014).
Chothia et al., "Canonical Structures for the Hypervariable Regions of Immunoglobulins," J. Mol. Biol., (1987) vol. 196, pp. 901-917.
Cline, "Perspectives for Gene Therapy: Inserting New Genetic Information into Mammalian Cells by Physical Techniques and Viral Vectors," Pharmac. Ther. (1985) vol. 29, pp. 69-92.
DeLano, "PyMOL: An Open-Source Molecular Graphics Tool," DeLano Scientific, (2002) pp. 1-9.
Drach et al., "Presence of a p53 Gene Deletion in Patients with Multiple Myeloma Predicts for Short Survival After Conventional-Dose Chemotherapy," Blood (1998) vol. 92(3), pp. 802-809.
Emsley et al., "Coot: Model-Building Tools for Molecular Graphics," Acta Cryst. (2004) D60, pp. 2126-2132.
European Search Report for European Patent Application No. 20177664.8 dated Nov. 23, 2020.
Facon et al., "Chromosome 13 Abnormalities Identified by FISH Analysis and Serum ?2-microglobulin Produce a Powerful Myeloma Staging System for Patients Receiving High-Dose Therapy," Blood (Mar. 15, 2001) vol. 91(6), pp. 1566-1571.
Ferrara et al., "Modulation of Therapeutic Antibody Effector Functions by Glycosylation Engineering: Influence of Golgi Enzyme Localization Domain and Co-Expression of Heterologous ?1, 4-N-acetylglucosaminyltransferase III and Golgi ?-mannosidase II," Biotechnology and Bioengineering (Apr. 5, 2006) vol. 93, No. 5, pp. 851-861.
Ferrara et al., "The Carbohydrate at FcyRIIIa Asn-162: An Element Required for High Affinity Binding to Non-Fuscosylated IgG Glycoforms," The Journal of Biological Chemistry (Feb. 24, 2006) vol. 281, No. 8, pp. 5032-5036.
Frankel et al., "Targeting T Cells to Tumor Cells Using Bispecific Antibodies," Curr Opin Chem Biol (Jun. 2013) vol. 17 (3), pp. 385-392. (Abstract Only).
Frerichs et al., "Preclinical Activity of JNJ-7957, a Novel BCMA xCD3 Bispecific Antibody for the Treatment of Multiple Myeloma, is Potentiated by Daratumumab," Clin. Cancer Res. (2020) vol. 26(9) pp. 2203-2215.
Frerichs et al., "Preclinical Evaluation of the New BCMA xCD3 Bispecific Antibody JNJ-957 for the Treatment of Multiple Myeloma," HemaSphere (2018) 2(S1), p. 729, Abs. S1579.
Frigyesi et al., "Robust Isolation of Malignant Plasma Cells in Multiple Myeloma," Blood (Feb. 27, 2014) vol. 123(9), pp. 1336-1340.
Gadi et al., "In Vivo Sensitization of Ovarian Tumors to Chemotherapy by Expression of E. coli Purine Nucleoside Phosphorylase in a Small Fraction of Cells," Gene Therapy (2000) vol. 7, pp. 1738-1743.

(56) References Cited

OTHER PUBLICATIONS

Garfall et al., "180 Updated Phase 1 Results of Teclistamab, a B-Cell Maturation Antigen (BCMA) ×CD3 Bispecific Antibody, in Relapsed and/or Refractory Multiple Myeloma (RRMM)," 62nd ASH Annual Meeting and Exposition, Dec. 5-8, 2020, Abstract.
Garfall et al., "Updated Phase 1 Results of Teclistamab, a B-Cell Maturation Antigen (BCMA) ×CD3 Bispecific Antibody, in Relapsed and/or Refractory Multiple Myeloma (RRMM)," Blood (Nov. 5, 2020) vol. 136, Suppl. 1, p. 27.
Garfall et al., "Updated Phase 1 Results of Teclistamab, a B-Cell Maturation Antigen (BCMA) ×CD3 Bispecific Antibody, in Relapsed and/or Refractory Multiple Myeloma (RRMM)," Presented at the 62nd ASH Annual Meeting, 2020, Abstract 180.
Gertz et al., "Clinical Implications of t(11;14)(q13;q32), t(4;14)(p16.3;q32), and 17p13 in Myeloma Patients Treated with High-Dose Therapy," Blood (2005) vol. 106(8), pp. 2837-2840.
Girgis et al., "3194 Translational Approach of Using Ex Vivo Cytotoxicity and Early Clinical Data to Predict Teclistamab Efficacious Therapeutic Range in Multiple Myeloma Patients," 62nd ASH Annual Meeting and Exposition, Dec. 5-8, 2020, Abstract.
Girgis et al., "Effects of Teclistamab and Talquetamab on Soluble BCMA Levels in Patients with Relapsed/Refractory Multiple Myeloma," Blood Advances (Aug. 25, 2022) pp. 1-21.
Girgis et al., "Teclistamab and Talquetamab Modulate Levels of Soluble B-Cell Maturation Antigen in Patients with Relapsed and/or Refractory Multiple Myeloma," Journal of Clinical Oncology (May 20, 2021) vol. 39, No. 15 Suppl, p. 8047.
Girgis et al., "Translational Approach of Using Ex Vivo Cytotoxicity and Early Clinical Data to Predict Teclistamab Efficacious Therapeutic Range in Multiple Myeloma Patients," Blood (Nov. 5, 2020) vol. 136, Suppl. 1, p. 35.
Girgis et al., "Translational Approach of Using Ex Vivo Cytotoxicity and Early Clinical Data to Predict Teclistamab Efficacious Therapeutic Range in Multiple Myeloma Patients," Presented at the 62nd ASH Annual Meeting & Exposition, Dec. 5-8, 2020.
Gras et al., "BCMAp: An Integral Membrane Protein in the Golgi Aapparatus of Human Mature B Lymphocytes," International Immunology (1995) vol. 7, No. 7, pp. 1093-1106.
Gross et al., "TACI and BCMA are Receptors for a TNF Homologue Implicated in B-Cell Automimmune Disease," Nature, 404:995-999, (Apr. 27, 2000).
Hagner et al., "Targeting B-Cell Maturation Antigen (BCMA with CC-93269, a 2+1 T Cell Engager, Elicits Significant Apoptosis in Diffuse Large B-Cell Lymphoma Preclinical Models," Blood (Nov. 13, 2019) vol. 134, p. 1580.
Holliger et al., "Diabodies: Small Bivalent and Bispecific Antibody Fragments," Proc. Natl. Acad. Sci. USA (Jul. 1993) vol. 90, pp. 6444-6448.
Holt et al., "Domain Antibodies: Proteins for Therapy," Trends in Biotechnology (Nov. 2003) vol. 21, No. 11, pp. 484-490.
Honegger et al., "Yet Another Numbering Scheme for Immunoglobulin Variable Domains: An Automatic Modeling and Analysis Tool," J. Mol. Biol. (2001) vol. 309, pp. 657-670.
Hymowitz et al., "Structures of APRIL-Receptor Complexes," The Journal of Biological Chemistry, 280(8): 7218-7227, (Feb. 25, 2005).
International Search Report and Written Opinion for International PCT Application No. PCT/EP2021/062364 dated Aug. 4, 2021.
Keymeulen et al., "Insulin Needs after CDS-Antibody Therapy in New-Onset Type 1 Diabetes," The New England Journal of Medicine, 352(25):2598-2608, (Jun. 23, 2005).
Knappik et al., "Fully Synthetic Human Combinatorial Antibody Libraries (HuCAL) Based on Modular Consensus Frameworks and CDRs Randomized with Trinucleotides," J. Mol. Biol. (2000) vol. 296, pp. 57-86.
Konno et al., "Fucose Content of Monoclonal Antibodies can be Controlled by Culture Medium Osmolality for High Antibody-Dependent Cellular Cytotoxicity," Cytotechnology (2012) vol. 64, pp. 249-265.

Laabi et al., "The BCMA Gene, Preferentially Expressed During B Lymphoid Maturation, is Bidirectionally Transcribed," Nucleic Acids Res. (1994) vol. 22 No. 7, pp. 1147-1154.
Laabi, et al., "A New Gene, BCM, on Chromosome 16 is Fused to the Interleukin 2 Gene by a t(4:16) (q26;p13) Translocation in a Malignant T Cell Lymphoma," The EMBO Journal, 11(11):3897-3904, (1992).
Laurent et al., "Y-Secretase Directly Sheds the Survival Receptor BCMA from Plasma Cells," Nat. Commun. (2015) vol. 6, Art. No. 7333, pp. 1-12.
Lee et al., "Evaluation of B Cell Maturation Antigen as a Target for Antibody Drug Conjugate Mediated Cytotoxicity in Multiple Myeloma," Br J Haematol. (2016) vol. 174, pp. 911-922.
Lefranc et al., "IMGT Unique Numbering for Immunoglobulin and T Cell Receptor Variable Domains and Ig Superfamily V-Like Domains," Dev. Comp. Immunol. (2003) vol. 27, pp. 55-77.
Li, et al., "Effect of PS-341 on Multiple Myeloma Cells Migrationa nd Secretion BAFF and APRIL," Aerosoace Medicine, 21(6):885-888, (Jun. 2010).
Liu et al., "Ligand-Receptor Binding Revealed by the TNF Family Member TALL-1," Nature, 423:49-56, (May 1, 2003).
Lonial et al., "Belantamab Mafodotin for Relapsed or Refractory Multiple Myeloma (DREAMM-2): a Two-Arm, Randomised, Open-Label, Phase 2 Study," Lancet Oncol. (2020) vol. 21(2), pp. 207-221.
Madry et al., "The Characterization of Murine BCMA Gene Defines it as a New Member of the Tumor Necrosis Factor Receptor Superfamily," Int Immunol (1998) vol. 10, No. 11, pp. 1693-1702.
Marriuzza et al., "The Structural Basis of Antigen-Antibody Recognition," Ann. Rev. Biophys. Chem. (1987) vol. 16, pp. 139-159.
Martin et al., "Structural Families in Loops of Homologous Proteins: Automatic Classification, Modelling and Application to Antibodies," J. Mol. Biol., (1996) vol. 263, pp. 800-815.
May et al., "Advances in Bispecific Biotherapeutics for the Treatment of Cancer," Biochem. Pharmacol. (Nov. 1, 2012) vol. 84, pp. 1105-1112.
Mori et al., "Engineering Chinese Hamster Ovary Cells to Maximize Effector Function of Produced Antibodies Using FUT8 siRNA," Biotechnology and Bioengineering (Dec. 30, 2004) vol. 88, No. 7, pp. 901-908.
Myers et al., "Optimal Alignments in Linear Space," Cabios (1988) vol. 4, No. 1, pp. 11-17.
Needleman et al., "A General Method Applicable to the Search for Similarities in the Amino Acid Sequence of Two Proteins," J. Mol. Biol. (1970) vol. 48, pp. 443-453.
Neuenschwander et al., "Critical Aspects of the Bayesian Approach to Phase I Cancer Trials," Statist. Med. (2008) vol. 27(13), pp. 2420-2439.
Novak et al., "Expression of BCMA, TACI, and BAFF-R in Multiple Myeloma: A Mechanism for Growth and Survival," Blood (Jan. 15, 2004) vol. 103(2). pp. 689-694.
Nunez-Prado et al., "The Coming of Age of Engineered Multivalent Antibodies," Drug Discovery Today (2015) vol. 20, No. 5, pp. 588-594.
Okayama et al., "A cDNA Cloning Vector that Permits Expression of cDNA Inserts in Mammalian Cells," Molecular and Cellular Biology (Feb. 1983) vol. 3, No. 2, pp. 280-289.
Olivier et al., "EB66 Cell Line, a Duck Embryonic Stem Cell-Derived Substrate for the Industrial Production of Therapeutic Monoclonal Antibodies with Enhanced ADCC Activity," mAbs (2010) vol. 2, No. 4, pp. 405-415.
Osborn et al., "High-Affinity IgG Antibodies Develop Naturally in Ig-Knockout Rats Carrying Germline Human IgH/Igk/Ig? Loci Bearing the Rat CH Region," The Journal of Immunology (2013) vol. 190, pp. 1481-1490.
Otwinowski et al., "[20] Processing of X-Ray Diffraction Data Collected in Oscillation Mode," Methods in Enzymology (1997) vol. 276, pp. 307-326.
Padlan et al., Structure of an antibody-antigen complex: crystal structure of the HyHEL-1 O Fab-lysozyme complex, PNAS 86:5938-594, 1989.
Palaiologou et al., "CD138 (syndecan-1) Expression in Health and Disease," Histol. Histopathol. (2014) vol. 29(2), pp. 177-189.

(56) References Cited

OTHER PUBLICATIONS

Pascalis et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunology (2002) vol. 169, pp. 3076-3084.
Pillarisetti et al., "Teclistamab is an Active T Cell-Redirecting Bispecific Antibody Against B-Cell Maturation Antigen for Multiple Myeloma," Blood Advances (Sep. 22, 2020) vol. 4, No. 18, pp. 4538-4549.
Raje et al., "Anti-BCMA CAR T-Cell Therapy bb2121 in Relapsed or Refractory Multiple Myeloma," N. Engl. J. Med. (2019) vol. 380(18), pp. 1726-1737.
Read, "Pushing the Boundaries of Molecular Replacement with Maximum Likelihood," Acta Cryst. (2001) D57, pp. 1373-1382.
Revets et al., "Nanobodies as Novel Agents for Cancer Therapy," Expert Opin. Biol. Ther. (2005) vol. 5, No. 1, pp. 111-124.
Rickert et al., "Signaling by the TNFR Superfamily in B-Cell Biology and Disease," Immunol. Rev., 244(1): 115-133, Nov. 2011.
Salmeron et al., "A Conformational Epitope Expressed upon Association of CD3-Epsilon with Either CD3-delta or CD3-gamma is the Main Target for Recognition by Anti-CD3 Monoclonal Antibodies," The Journal of Immunology (1991) vol. 147, No. 9, pp. 3047-3052.
Sanchez et al., "Serum B-Cell Maturation Antigen is Elevated in Multiple Myeloma and Correlates with Disease Status and Survival," British Journal of Hematology (Jul. 18, 2012) vol. 158, No. 158, pp. 727-738.
Shi et al., "De Novo Selection of High-Affinity Antibodies from Synthetic Fab Libraries Displayed on Phage as pIX Fusion Proteins," J. Mol. Biol. (2010) vol. 397, pp. 385-396.
Shields et al., "Lack of Fucose on Human IgG1 N-Linked Oligosaccharide Improves Binding to Human FcγRIII and Antibody-Dependent Cellular Toxicity," The Journal of Biological Chemistry (2002) vol. 227, No. 30, pp. 26733-26740.
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry (2002) vol. 278, No. 5, pp. 3466-3473.
Stein et al., "Benefit-Risk Assessment of Blinatumomab in the Treatment of Relapsed/Refractory B-Cell Precursor Acute Lymphoblastic Leukemia," Drug. Saf. (2019) vol. 42, pp. 587-601.
Stickler et al., "The Human G1m1 Allotype Associates with CD4+ T-Cell Responsiveness to a Highly Conserved IgG1 Constant Region Peptide and Confers an Asparaginyl Endopeptidase Cleavage Site," Genes and Immunity (2011) vol. 12, pp. 213-221.
Tai et al., "Targeting B-Cell Maturation Antigen in Multiple Myeloma," Immunotherapy (Nov. 2015) vol. 7(11), pp. 1187-1199.

Topp et al., "8007: Evaluation of AMG 420, an Anti-BCMA Bispecific T-Cell Engager (BiTE) Immunotherapy, in R/R Multiple Myeloma (MM) Patients: Updates Results of a First-in-Human (FIH) Phase I Dose Escalation Study," Journal of Clinical Oncology (May 20, 2019) vol. 37, Suppl. 15, p. 8007.
Topp et al., "Anti-B-Cell Maturation Antigen BiTE Molecule AMG 420 Induces Responses in Multiple Myeloma," J. Clin. Oncol. (2020) vol. 38(8), pp. 775-783.
U.S. Appl. No. 18/052,174, filed Nov. 2, 2022.
U.S. Appl. No. 18/053,904, filed Nov. 9, 2022.
Usmani et al., "Phase 1 Study of Teclistamab, a Humanized B-Cell Maturation Antigen (BCMA) ×CD3 Bispecific Antibody, in Relapsed or Refractory Multiple Myeloma," Presented at the 56th ASCO Annual Meeting, 2020, Abstract 100.
Usmani et al., "Phase I Study of Teclistamab, A Humanized B-Cell Maturation Antigen (BCMA) ×CD3 Bispecific Antibody, in Relapsed/Refractory Multiple Myeloma (R/R MM)," 2020 ASCO Annual Meeting I, Meeting Abstract, Journal of Clinical Oncology, vol. 38, No. 15, Suppl 100.
Usmani et al., "Teclistamab, a B-Cell Maturation AntigenxCD3 Bispecific Antibody, in Patients with Relapsed or Refractory Multiple Myeloma (MajesTEC-1): a Multicentre, Open-Label, Single-Arm, Phase 1 Study," The Lancet (Aug. 1, 2021) vol. 398, No. 10301, pp. 665-674.
Ward et al., "Binding Activities of a Repertoire of Single Immunoglobulin Variable Domains Secreted from *Escherichia coli*," Nature (1989) vol. 341, pp. 544-546.
Wu et al., "An Analysis of the Sequences of the Variable Regions on Bence Jones Proteins and Myeloma Light Chains and Their Implications for Anti-Body Complementarity," J. Exp. Med. (1970) 132, pp. 211-250.
XP002762973, Anti-CD3 Epsilon Humanized Antibody VL Region Coding Gene, Seq ID 55, Database Geneseq (online), Jan. 17, 2013, Database Accession No. BAG88459.
XP002762974, Anti-Ha mAb (CL860UCA) Ligh Chain Variable Region Coding Gene, Seq 5, Database Geneseq (online) Apr. 11, 2013, Database Accession No. BAK30778.
XP002762975, Anti-CD3 Variant Humarized Antibody BH (XENP11810H1.15_L1.4), Seq 57, Database Geneseq (Online), Dec. 4, 2014, Database Accession No. BBP23340.
Yang et al., "A Common Pathway for T Lymphocyte Activation Involving Both the CD3-Ti Complex and CD2 Sheep Erythrocyte Receptor Determinants," The Journal of Immunology (1986) vol. 137, No. 4, pp. 1097-1100.
Zhou et al., "Development of A Simple and Rapid Method for Producing Non-Fucosylated Oligomannose Containing Antibodies With Increased Effector Function," Biotechnology and Bioengineering (2008) vol. 99, No. 3, pp. 652-665.

\* cited by examiner

SEM=standard error of the mean.

SEM=standard error of the mean.

One-way ANOVA was performed.
ANOVA=analysis of variance; dara=daratumumab; NDMM=newly diagnosed multiple myeloma; RRMM=relapsed/refractory multiple myeloma.

Analysis via paired t-test.
BM=bone marrow

BCMA=B cell maturation antigen; CD3=cluster of differentiation 3; NSG=NOD/scidγc-/-; PBMC=peripheral blood mononuclear cell; PBS=phosphate-buffered saline; SEM=standard error of the mean.

BCMA=B cell maturation antigen; CD3=cluster of differentiation 3; MM=multiple myeloma; NSG=NOD/scidyc-/-; PBMC=peripheral blood mononuclear cell; SEM=standard error of the mean.

CR = complete response, sCR = stringent complete response, VGPR = very good partial response, PR = partial response, MR = minimal response, SD = stable disease, PD = progressive disease, D/C = discontinued IV=intravenous; QW=weekly; Q2W=every other week Values reflect the median value per timepoint. [a]2 step-up doses, [b]3 step-up doses Values reflect the median value per timepoint. [a]2 step-up doses, [b]3 step-up doses

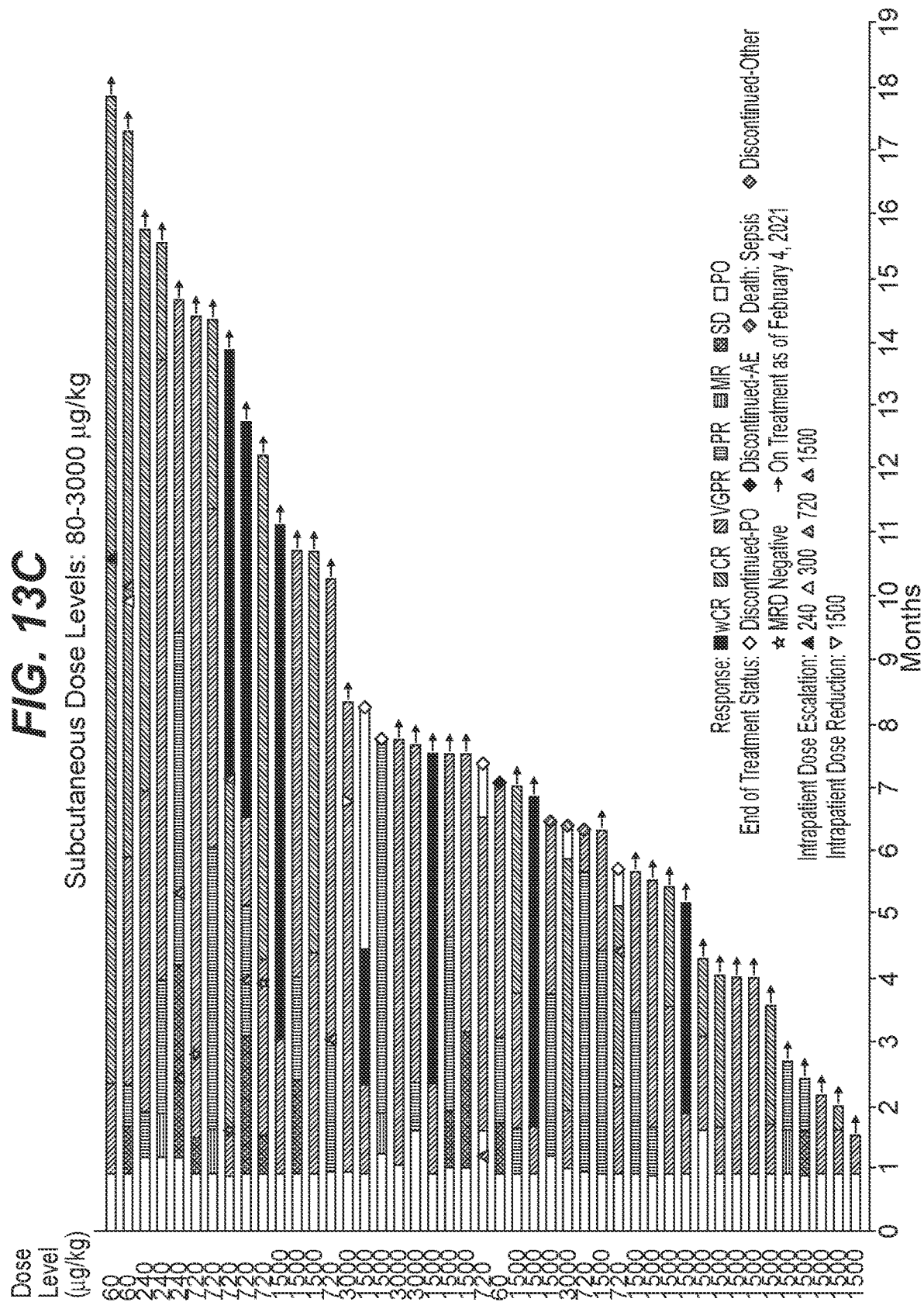

```
                        SEQUENCE LISTING

<160> NUMBER OF SEQ ID NOS: 24

<210> SEQ ID NO 1
<211> LENGTH: 184
<212> TYPE: PRT
<213> ORGANISM: Homo sapiens

<400> SEQUENCE: 1

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125
```

```
Glu Asp Cys Ile Lys Ser Lys Pro Lys Val Asp Ser Asp His Cys Phe
    130                 135                 140
Pro Leu Pro Ala Met Glu Gly Ala Thr Ile Leu Val Thr Thr Lys
145                 150                 155                 160
Thr Asn Asp Tyr Cys Lys Ser Leu Pro Ala Ala Leu Ser Ala Thr Glu
                165                 170                 175
Ile Glu Lys Ser Ile Ser Ala Arg
            180

<210> SEQ ID NO 2
<211> LENGTH: 207
<212> TYPE: PRT
<213> ORGANISM: Homo sapiens

<400> SEQUENCE: 2

Met Gln Ser Gly Thr His Trp Arg Val Leu Gly Leu Cys Leu Leu Ser
1               5                   10                  15
Val Gly Val Trp Gly Gln Asp Gly Asn Glu Glu Met Gly Gly Ile Thr
                20                  25                  30
Gln Thr Pro Tyr Lys Val Ser Ile Ser Gly Thr Thr Val Ile Leu Thr
            35                  40                  45
Cys Pro Gln Tyr Pro Gly Ser Glu Ile Leu Trp Gln His Asn Asp Lys
        50                  55                  60
Asn Ile Gly Gly Asp Glu Asp Asp Lys Asn Ile Gly Ser Asp Glu Asp
65                  70                  75                  80
His Leu Ser Leu Lys Glu Phe Ser Glu Leu Glu Gln Ser Gly Tyr Tyr
                85                  90                  95
Val Cys Tyr Pro Arg Gly Ser Lys Pro Glu Asp Ala Asn Phe Tyr Leu
            100                 105                 110
Tyr Leu Arg Ala Arg Val Cys Glu Asn Cys Met Glu Met Asp Val Met
        115                 120                 125
Ser Val Ala Thr Ile Val Ile Val Asp Ile Cys Ile Thr Gly Gly Leu
130                 135                 140
Leu Leu Leu Val Tyr Tyr Trp Ser Lys Asn Arg Lys Ala Lys Ala Lys
145                 150                 155                 160
Pro Val Thr Arg Gly Ala Gly Ala Gly Gly Arg Gln Arg Gly Gln Asn
                165                 170                 175
Lys Glu Arg Pro Pro Pro Val Pro Asn Pro Asp Tyr Glu Pro Ile Arg
            180                 185                 190
Lys Gly Gln Arg Asp Leu Tyr Ser Gly Leu Asn Gln Arg Arg Ile
        195                 200                 205

<210> SEQ ID NO 3
<211> LENGTH: 104
<212> TYPE: PRT
<213> ORGANISM: Homo sapiens

<400> SEQUENCE: 3

Asp Gly Asn Glu Glu Met Gly Gly Ile Thr Gln Thr Pro Tyr Lys Val
1               5                   10                  15
Ser Ile Ser Gly Thr Thr Val Ile Leu Thr Cys Pro Gln Tyr Pro Gly
                20                  25                  30
Ser Glu Ile Leu Trp Gln His Asn Asp Lys Asn Ile Gly Gly Asp Glu
            35                  40                  45
Asp Asp Lys Asn Ile Gly Ser Asp Glu Asp His Leu Ser Leu Lys Glu
        50                  55                  60
```

Phe Ser Glu Leu Glu Gln Ser Gly Tyr Tyr Val Cys Tyr Pro Arg Gly
65                  70                  75                  80

Ser Lys Pro Glu Asp Ala Asn Phe Tyr Leu Tyr Leu Arg Ala Arg Val
                85                  90                  95

Cys Glu Asn Cys Met Glu Met Asp
            100

<210> SEQ ID NO 4
<211> LENGTH: 7
<212> TYPE: PRT
<213> ORGANISM: Artificial Sequence
<220> FEATURE:
<223> OTHER INFORMATION: BCMB69 HCDR1

<400> SEQUENCE: 4

Ser Gly Ser Tyr Phe Trp Gly
1               5

<210> SEQ ID NO 5
<211> LENGTH: 16
<212> TYPE: PRT
<213> ORGANISM: Artificial Sequence
<220> FEATURE:
<223> OTHER INFORMATION: BCMB69 HCDR2

<400> SEQUENCE: 5

Ser Ile Tyr Tyr Ser Gly Ile Thr Tyr Tyr Asn Pro Ser Leu Lys Ser
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: BCMB69 HCDR3

<400> SEQUENCE: 6

His Asp Gly Ala Val Ala Gly Leu Phe Asp Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: BCMB69 LCDR1

<400> SEQUENCE: 7

Gly Gly Asn Asn Ile Gly Ser Lys Ser Val His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: BCMB69 LCDR2

<400> SEQUENCE: 8

Asp Asp Ser Asp Arg Pro Ser
1               5

<210> SEQ ID NO 9
<211> LENGTH: 11
<212> TYPE: PRT

<213> ORGANISM: Artificial Sequence
<220> FEATURE:
<223> OTHER INFORMATION: BCMB69 LCDR3

<400> SEQUENCE: 9

Gln Val Trp Asp Ser Ser Asp His Val Val
1               5                   10

<210> SEQ ID NO 10
<211> LENGTH: 121
<212> TYPE: PRT
<213> ORGANISM: Artificial Sequence
<220> FEATURE:
<223> OTHER INFORMATION: BCMB69 VH

<400> SEQUENCE: 10

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser
        115                 120

<210> SEQ ID NO 11
<211> LENGTH: 111
<212> TYPE: PRT
<213> ORGANISM: Artificial Sequence
<220> FEATURE:
<223> OTHER INFORMATION: BCMB69 VL

<400> SEQUENCE: 11

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Pro Pro Gly Gln Ala Pro Val Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Asp His
                85                  90                  95

Val Val Phe Gly Gly Gly Thr Lys Leu Thr Val Leu Gly Gln Pro
            100                 105                 110

<210> SEQ ID NO 12
<211> LENGTH: 448
<212> TYPE: PRT
<213> ORGANISM: Artificial Sequence

```
<220> FEATURE:
<223> OTHER INFORMATION: BCMB69 HC

<400> SEQUENCE: 12

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
            20                  25                  30

Ser Tyr Phe Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Asp Gly Ala Val Ala Gly Leu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 13
<211> LENGTH: 214
<212> TYPE: PRT
<213> ORGANISM: Artificial Sequence
<220> FEATURE:
<223> OTHER INFORMATION: BCMB69 LC

<400> SEQUENCE: 13

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Pro Pro Gly Gln Ala Pro Val Val Val Val Tyr
            35                  40                  45

Asp Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Val Tyr Tyr Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Gly Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 14
<211> LENGTH: 5
<212> TYPE: PRT
<213> ORGANISM: Artificial Sequence
<220> FEATURE:
<223> OTHER INFORMATION: CD3B219 HCDR1

<400> SEQUENCE: 14

Thr Tyr Ala Met Asn
1               5

<210> SEQ ID NO 15
<211> LENGTH: 19
<212> TYPE: PRT
```

<213> ORGANISM: Artificial Sequence
<220> FEATURE:
<223> OTHER INFORMATION: CD3B219 HCDR2

<400> SEQUENCE: 15

Arg Ile Arg Ser Lys Tyr Asn Asn Tyr Ala Thr Tyr Tyr Ala Ala Ser
1               5                   10                  15

Val Lys Gly

<210> SEQ ID NO 16
<211> LENGTH: 14
<212> TYPE: PRT
<213> ORGANISM: Artificial Sequence
<220> FEATURE:
<223> OTHER INFORMATION: CD3B219 HCDR3

<400> SEQUENCE: 16

His Gly Asn Phe Gly Asn Ser Tyr Val Ser Trp Phe Ala Tyr
1               5                   10

<210> SEQ ID NO 17
<211> LENGTH: 14
<212> TYPE: PRT
<213> ORGANISM: Artificial Sequence
<220> FEATURE:
<223> OTHER INFORMATION: CD3B219 LCDR1

<400> SEQUENCE: 17

Arg Ser Ser Thr Gly Ala Val Thr Thr Ser Asn Tyr Ala Asn
1               5                   10

<210> SEQ ID NO 18
<211> LENGTH: 7
<212> TYPE: PRT
<213> ORGANISM: Artificial Sequence
<220> FEATURE:
<223> OTHER INFORMATION: CD3B219 LCDR2

<400> SEQUENCE: 18

Gly Thr Asn Lys Arg Ala Pro
1               5

<210> SEQ ID NO 19
<211> LENGTH: 9
<212> TYPE: PRT
<213> ORGANISM: Artificial Sequence
<220> FEATURE:
<223> OTHER INFORMATION: CD3B219 LCDR3

<400> SEQUENCE: 19

Ala Leu Trp Tyr Ser Asn Leu Trp Val
1               5

<210> SEQ ID NO 20
<211> LENGTH: 125
<212> TYPE: PRT
<213> ORGANISM: Artificial Sequence
<220> FEATURE:
<223> OTHER INFORMATION: CD3B219 VH

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

```
Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Ala
        50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 21
<211> LENGTH: 112
<212> TYPE: PRT
<213> ORGANISM: Artificial Sequence
<220> FEATURE:
<223> OTHER INFORMATION: CD3B219 VL

<400> SEQUENCE: 21

Gln Thr Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
                20                  25                  30

Asn Tyr Ala Asn Trp Val Gln Gln Lys Pro Gly Gln Ala Pro Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

<210> SEQ ID NO 22
<211> LENGTH: 452
<212> TYPE: PRT
<213> ORGANISM: Artificial Sequence
<220> FEATURE:
<223> OTHER INFORMATION: CD3B219 HC

<400> SEQUENCE: 22

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Ala
        50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110
```

Ala Tyr Trp Gly Gln Gly Thr Leu Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
    450

<210> SEQ ID NO 23
<211> LENGTH: 215
<212> TYPE: PRT
<213> ORGANISM: Artificial Sequence
<220> FEATURE:
<223> OTHER INFORMATION: CD3B219 LC

<400> SEQUENCE: 23

Gln Thr Val Val Thr Gln Glu Pro Ser Leu Thr Val Ser Pro Gly Gly
1               5                   10                  15

```
Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
        210                 215

<210> SEQ ID NO 24
<211> LENGTH: 327
<212> TYPE: PRT
<213> ORGANISM: Artificial Sequence
<220> FEATURE:
<223> OTHER INFORMATION: wild-type IgG4

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
            245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325
```

METHODS FOR TREATING MULTIPLE MYELOMA

CROSS-REFERENCE TO RELATED APPLICATIONS

This application claims the benefit of U.S. Provisional Application Ser. No. 63/023,092, filed 11 May 2020, U.S. Provisional Application Ser. No. 63/024,209, filed 13 May 2020, and U.S. Provisional Application Ser. No. 63/159,303, filed 10 Mar. 2021. The entire content of the aforementioned applications is incorporated herein by reference in its entirety.

SEQUENCE LISTING

The instant application contains a Sequence Listing which has been submitted electronically in ASCII format and is hereby incorporated by reference in its entirety. Said ASCII copy, created on May 12, 2020, is named "PRD4087 SL.txt" and is 26,072 bytes in size.

FIELD OF THE INVENTION

Methods of treating cancers using a BCMAxCD3 bispecific antibody are disclosed.

BACKGROUND OF THE INVENTION

B-cell maturation antigen (BCMA), also known as CD269 and tumor necrosis factor (TNF) receptor superfamily member 17, is a receptor that plays a critical role in B lymphocytes (B cell) maturation and subsequent differentiation into plasma cells. BCMA binds 2 ligands: A proliferation-inducing ligand (APRIL; CD256) and BAFF. APRIL and BAFF are type II transmembrane proteins that are readily cleaved by Furin and secreted as soluble trimers by many cells (B cells [autocrine], monocytes, dendritic cells, T cells, osteoclasts, etc.) and can bind to the BCMA receptor. Different from other surface markers, BCMA is exclusively expressed in B-lineage cells and is selectively induced during plasma cell differentiation.

A human BCMA receptor is a 184 amino acid protein that neither has a secretory signal sequence nor any specific protease cleavage site in the N-terminal 54 amino acid extracellular domain. However, the N-terminal fragment is observed as a soluble protein in the serum as a result of gamma secretase activity that cleaves BCMA protein at the transmembrane domain (Laurent et al., *Nat Commun*. 2015; 6:7333). Inhibition of gamma secretase treatment results in significant increase of BCMA surface protein in human primary B-cells (Laurent et al., 2015, id.). High levels of soluble BCMA (sBCMA) were measured in multiple myeloma patient serum samples (data not shown) and correlated with the plasma cell counts (Sanchez et al., *Br J Haematol*. 2012; 158(6):727-738).

BCMA mRNA and protein were universally detected in MM cell lines and in all malignant plasma cells from multiple myeloma patients by Applicants (data not shown) and others (Carpenter et al., *Clin Cancer Res*. 2013; 19(8): 2048-2060; Novak et al., *Blood*. 2004; 103(2):689-694). Similarly, in multiple myeloma cell lines and patient samples, BCMA is more stably expressed compared with a key plasma cell marker (CD138) that is also expressed on normal fibroblasts and epithelial cells (Palaiologou et al., *Histol Histopathol*. 2014; 29(2):177-189). BCMA expression is selective for B cell lineage and was not detected in any major tissues except for infiltrating plasma cells as determined by immunohistochemistry (IHC) methods (Carpenter et al., 2014, id.). Taken together, the selective expression of BCMA on the B cell lineage makes it an appealing target for T-cell mediated therapy to treat plasma cell disorders like multiple myeloma (Frigyesi et al., *Blood*. 2014; 123(9):1336-1340; Tai et al, *Immunotherapy*. 2015; 7(11): 1187-1199).

Multiple myeloma (MM) is the second most common hematological malignancy and constitutes 2% of all cancer deaths. MM is a heterogeneous disease and caused by mostly by chromosome translocations inter alia t(11;14),t(4; 14),t(8;14),del(13),del(17) (Drach et al., *Blood*. 1998; 92(3): 802-809, Gertz et al., *Blood*. 2005;106(8).2837-2840; Facon et al., *Blood*. 2001; 97(6): 1566-1571). MM-affected patients can experience a variety of disease-related symptoms due to, bone marrow infiltration, bone destruction, renal failure, immunodeficiency, and the psychosocial burden of a cancer diagnosis. As of 2006, the 5-year relative survival rate for MM was approximately 34% highlighting that MM is a difficult-to-treat disease where there are currently no curative options.

Relapsed and refractory multiple myeloma constitutes a specific unmet medical need. Patients with relapsed and refractory disease are defined as those who achieve minor response or better then progress while on therapy or who experience progression within 60 days of their last therapy. Patients who progress after receiving both an immunomodulatory drug and proteasome inhibitor have limited options. Heavily pretreated patients often present with a compromised immune system, which can result in other disease conditions such as opportunistic infections and toxicities (eg, myelosuppression, peripheral neuropathy, deep vein thrombosis) that persist from prior treatment. Furthermore, patients with advanced multiple myeloma are often elderly and are susceptible to serious treatment-emergent adverse events (TEAEs) with continued exposure to these therapies. After standard available therapies (such as proteasome inhibitors, immunomodulatory drugs, and monoclonal antibodies) have been exhausted, there is no standard therapy. Selinexor is licensed in the United States for this highly refractory disease setting. The remaining options for these patients are either entry into a clinical trial, or they can be offered retreatment with a prior treatment regimen (if the toxicity profile for retreatment permits). But often, if no other treatment options remain, they are provided with palliative care to ameliorate disease-related symptoms only.

T cell redirected killing is a desirable mode of action in many therapeutic areas. In general T cell redirecting molecules are engineered to have at least two antigen binding sites wherein one site binds a surface antigen on a target cell and the other site binds a T cell surface antigen. Amongst T cell surface antigens, the human CD3 epsilon subunit from the TCR protein complex has been the most targeted to redirect T cell killing. Various bispecific antibody formats have been shown to mediate T cell redirection in both in pre-clinical and clinical investigations (May C et al., *Biochem Pharmacol*, 84: 1105-12, 2012; Frankel S R & Baeuerle P A, *Curr Opin Chem Biol*, 17(3): 385-92, 2013).

The use of anti-BCMA antibodies for the treatment of lymphomas and multiple myeloma is mentioned in WO2002066516 and WO2010104949. Antibodies against BCMA are described, e.g. in Gras M-P. et al. *Int Immunol*. 1997; 7:1093-1106, WO200124811, and WO200124812. Bispecific antibodies against BCMA and CD3 are described e.g. in WO2017/031104. Nevertheless, despite the fact that BCMA and other B cell receptors belonging to the TNF receptor superfamily, and their ligands BAFF and APRIL are subject to therapies in fighting against cancers, there is still a need for having available further options for the treatment of such medical conditions.

SUMMARY OF THE INVENTION

The disclosure provides a method of treating a cancer in a subject in need thereof, comprising administering a therapeutically effective amount of a BCMAxCD3 bispecific antibody to the subject to treat the cancer, wherein the subject is relapsed or refractory to treatment with a prior anti-cancer therapeutic.

The disclosure also provides a method of treating a multiple myeloma in a subject in need thereof, comprising administering a therapeutically effective amount of a BCMAxCD3 bispecific antibody to the subject to treat the multiple myeloma.

The disclosure also provides a method of treating a multiple myeloma in a subject in need thereof, comprising administering a therapeutically effective amount of a BCMAxCD3 bispecific antibody to the subject to treat the multiple myeloma, wherein the subject is relapsed or refractory to treatment with a prior multiple myeloma therapeutic.

The disclosure also provides a method of treating a multiple myeloma in a subject in need thereof, comprising administering a therapeutically effective amount of a BCMAxCD3 bispecific antibody to the subject to treat the multiple myeloma, wherein the BCMAxCD3 bispecific antibody is administered for a time sufficient to achieve stringent complete response, complete response, very good partial response, partial response, minimal response or stable disease status.

The disclosure also provides a method of treating a multiple myeloma in a subject in need thereof, comprising administering a therapeutically effective amount of a BCMAxCD3 bispecific antibody to the subject to treat the multiple myeloma, wherein the BCMAxCD3 bispecific antibody is administered for a time sufficient to achieve complete response associated with negative minimal residual disease (MRD) status.

In particular embodiments, the BCMAxCD3 bispecific antibody comprises a BCMA binding domain comprising the VH of SEQ ID NO: 10 and the VL of SEQ ID NO: 11, and a CD3 biding domain comprising the VH of SEQ ID NO: 20 and the VL of SEQ ID NO: 21.

In particular embodiments, the BCMAxCD3 bispecific antibody is teclistamab.

BRIEF DESCRIPTION OF THE DRAWINGS

FIG. 13C shows the duration of response in patients in the subcutaneous dosing cohorts at the Second Data Cutoff;

DETAILED DESCRIPTION OF THE INVENTION

Figure 1:
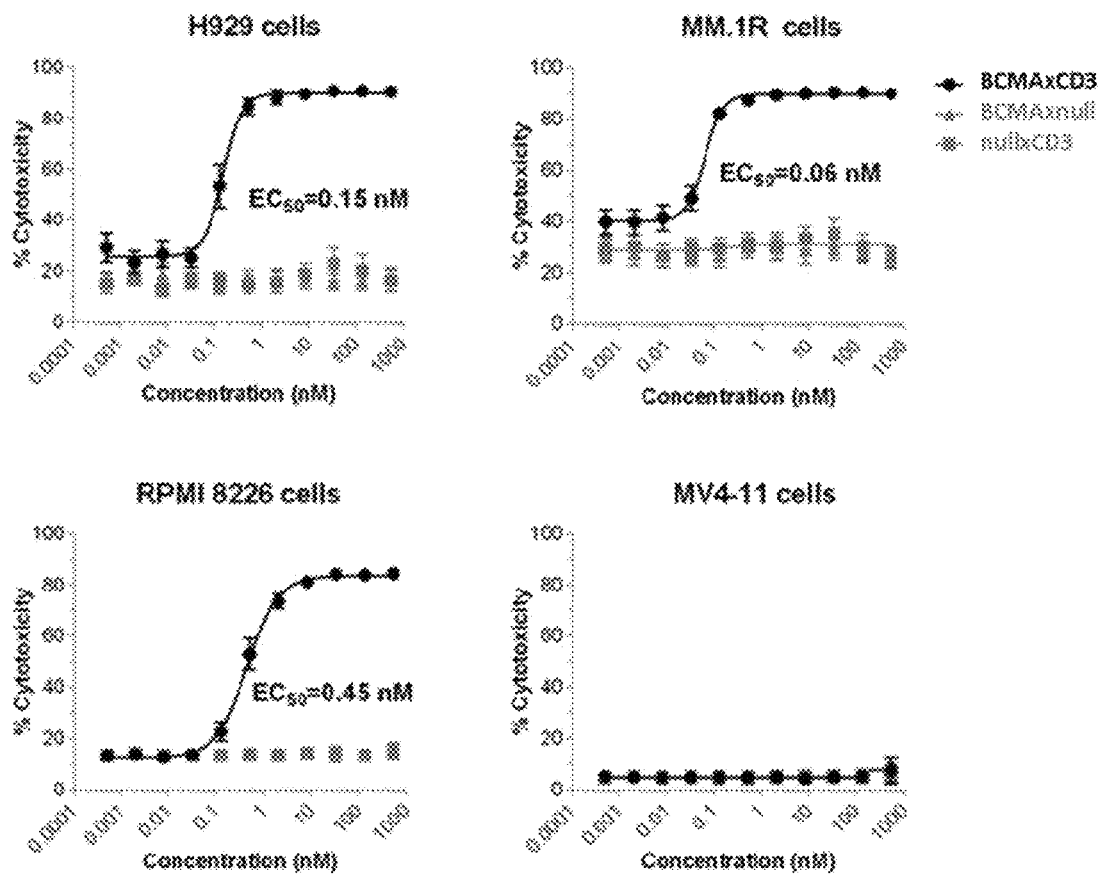
FIG. 1 shows the T cell-mediated Teclistamab-dependent cytotoxicity of multiple myeloma cell lines.

The disclosed methods can be understood more readily by reference to the following detailed description taken in connection with the accompanying figures, which form a part of this disclosure. It is to be understood that the disclosed methods are not limited to the specific methods described and/or shown herein, and that the terminology used herein is for the purpose of describing particular embodiments by way of example only and is not intended to be limiting of the claimed methods. All patents, published patent applications and publications cited herein are incorporated by reference as if set fourth fully herein.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

"About" when used in reference to numerical ranges, cutoffs, or specific values means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of an assay, result or embodiment, "about" means within one standard deviation per the practice in the art, or a range of up to 5%, whichever is larger.

"Antibodies" is meant in a broad sense and includes immunoglobulin molecules including monoclonal antibodies including murine, human, humanized and chimeric monoclonal antibodies, antigen binding fragments, multispecific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions can be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4. Immunoglobulins can be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species can be assigned to one of two clearly distinct types, namely kappa (κ) and lambda (λ), based on the amino acid sequences of their constant domains.

"Antigen binding fragment" or "antigen binding domain" refers to a portion of an immunoglobulin molecule that binds an antigen. Antigen binding fragments can be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains can be linked together via a synthetic linker to form various types of single chain antibody designs where the VH/VL domains can pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"BCMA" refers to human B-cell maturation antigen, also known as CD269 or TNFRSF17 (UniProt Q02223). The extracellular domain of BCMA encompasses residues 1-54 of Q02223. Human BCMA comprises the amino acid sequence of SEQ ID NO: 1.

```
                                          SEQ ID NO: 1
MLQMAGQCSQNEYFDSLLHACIPCQLRCSSNTPPLTCQRYCNASVTNSV

KGTNAILWTCLGLSLIISLAVFVLMFLLRKINSEPLKDEFKNTGSGLLG

MANIDLEKSRTGDEIILPRGLEYTVEECTCEDCIKSKPKVDSDHCFPLP

AMEEGATILVTTKTNDYCKSLPAALSATEIEKSISAR
```

"Bispecific" refers to an antibody that specifically binds two distinct antigens or two distinct epitopes within the same antigen. The bispecific antibody can have cross-reactivity to other related antigens, for example to the same antigen from other species (homologs), such as human or monkey, for example *Macaca cynomolgus* (cynomolgus, cyno) or *Pan troglodytes*, or can bind an epitope that is shared between two or more distinct antigens.

"BCMAxCD3 bispecific antibody" refers to a bispecific antibody that specifically binds BCMA and CD3.

"Cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. A "cancer" or "cancer tissue" can include a tumor.

"CD3" refers to a human antigen which is expressed on T cells as part of the multimolecular T cell receptor (TCR) complex and which consists of a homodimer or heterodimer formed from the association of two or four receptor chains: CD3 epsilon, CD3 delta, CD3 zeta and CD3 gamma. Human CD3 epsilon comprises the amino acid sequence of SEQ ID NO: 2. SEQ ID NO: 3 shows the extracellular domain of CD3 epsilon.

```
                                          SEQ ID NO: 2
MQSGTHWRVLGLCLLSVGVWGQDGNEEMGGITQTPYKVSISGTTVILTC

PQYPGSEILWQHNDKNIGGDEDDKNIGSDEDHLSLKEFSELEQSGYYVC

YPRGSKPEDANFYLYLRARVCENCMEMDVMSVATIVIVDICITGGLLLL

VYYWSKNRKAKAKPVTRGAGAGGRQRGQNKERPPPVPNPDYEPIRKGQR

DLYSGLNQRRI

SEQ ID NO: 3
DGNEEMGGITQTPYKVSISGTTVILTCPQYPGSEILWQHNDKNIGGDED

DKNIGSDEDHLSLKEFSELEQSGYYVCYPRGSKPEDANFYLYLRARVCE

NCMEMD
```

"CH3 region" or "CH3 domain" refers to the CH3 region of an immunoglobulin. The CH3 region of human IgG1 antibody corresponds to amino acid residues 341-446. However, the CH3 region can also be any of the other antibody isotypes as described herein.

"Combination" means that two or more therapeutics are administered to a subject together in a mixture, concurrently as single agents or sequentially as single agents in any order.

"Complementarity regions" (CDR) are antibody regions that bind an antigen. CDRs can be defined using various delineations such as Kabat (Wu et al. *J Exp Med* 132: 211-50, 1970) (Kabat et al., Sequences of Proteins of Immunological Interest, 5th Ed. Public Health Service, National Institutes of Health, Bethesda, Md., 1991), Chothia (Chothia et al. *J Mol Biol* 196: 901-17, 1987), IMGT (Lefranc et al. *Dev Comp Immunol* 27: 55-77, 2003) and AbM (Martin and Thornton *J Bmol Biol* 263: 800-15, 1996). The correspondence between the various delineations and variable region numbering are described (see e.g. Lefranc et al. *Dev Comp Immunol* 27: 55-77, 2003; Honegger and Pluckthun, *J Mol Biol* 309:657-70, 2001; International ImMunoGeneTics (IMGT) database; Web resources, http://www_imgt_org). Available programs such as abYsis by UCL Business PLC can be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification "Comprising" is intended to include examples encompassed by the terms "consisting essentially of" and "consisting of"; similarly, the term "consisting essentially of" is intended to include examples encompassed by the term "consisting of." Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

"Enhance" or "enhanced" refers to enhancement in one or more functions of a test molecule when compared to a control molecule or a combination of test molecules when compared to one or more control molecules. Exemplary functions that can be measured are tumor cell killing, T cell activation, relative or absolute T cell number, Fc-mediated effector function (e.g. ADCC, CDC and/or ADCP) or binding to an Fcγ receptor (FcγR) or FcRn. "Enhanced" can be an enhancement of about 10%, 20%, 30%, 40%, 50%, 60%, 70%, 80%, 90%, 100% or more, or a statistically significant enhancement.

"Fc gamma receptor" (FcγR) refers to well-known FcγRI, FcγRIIa, FcγRIIb or FcγRIII. Activating FcγR includes FcγRI, FcγRIIa and FcγRIII.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" can contain consensus framework sequences derived from human framework sequence analyses, for example as described in Knappik et al., (2000) J Mol Biol 296:57-86, or synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

"Humanized antibody" refers to an antibody in which at least one CDR is derived from non-human species and at least one framework is derived from human immunoglobulin sequences. Humanized antibody can include substitutions in the frameworks so that the frameworks can not be exact copies of expressed human immunoglobulin or human immunoglobulin germline gene sequences.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies can have heterogeneous glycosylation within the antibody population. Monoclonal antibody can be monospecific or multispecific such as bispecific, monovalent, bivalent or multivalent.

"Mutation" refers to an engineered or naturally occurring alteration in a polypeptide or polynucleotide sequence when compared to a reference sequence. The alteration can be a substitution, insertion or deletion of one or more amino acids or polynucleotides.

"Multispecific" refers to an antibody that specifically binds at least two distinct antigens or at least two distinct epitopes within the same antigen. Multispecific antibody can bind for example two, three, four or five distinct antigens or distinct epitopes within the same antigen.

"Negative minimal residual disease status" or "negative MRD status" or "MRD negative" refers to the PerMillionCount (i.e., a point estimate of malignant myeloma cells per million nucleated cells) in a patients on-study bone marrow sample relative to their reference bone marrow sample (i.e., Teclistamab treatment naïve bone marrow sample). Based on this PerMillionCount, each sample is determined to be positive or negative. Samples are positive if the PerMillionCount is greater than or equal to the limit of sensitivity, otherwise they are negative. Negative minimal residual disease status can be determined at a sensitivity of 0.01% ($10^{-4}$), 0.001% ($10^{-5}$) or 0.0001% ($10^{-6}$). Negative minimal residual disease status was determined using next generation sequencing (NGS).

"Pharmaceutical composition" refers to composition that comprises an active ingredient and a pharmaceutically acceptable carrier.

"Pharmaceutically acceptable carrier" or "excipient" refers to an ingredient in a pharmaceutical composition, other than the active ingredient, which is nontoxic to a subject.

"Recombinant" refers to DNA, antibodies and other proteins that are prepared, expressed, created or isolated by recombinant means when segments from different sources are joined to produce recombinant DNA, antibodies or proteins.

"Reduce" or "reduced" refers to a reduction in one or more functions of a test molecule when compared to a control molecule or a combination of test molecules when compared to one or more control molecules. Exemplary functions that can be measured are tumor cell killing, T cell activation, relative or absolute T cell number, Fc-mediated effector function (e.g. ADCC, CDC and/or ADCP) or binding to an Fcγ receptor (FcγR) or FcRn. "Reduced" can be a reduction of about 10%, 20%, 30%, 40%, 50%, 60%, 70%, 80%, 90%, 100% or more, or a statistically significant enhancement.

"Refractory" refers to a cancer that is not amendable to surgical intervention and is initially unresponsive to therapy.

"Relapsed" refers to a cancer that responded to treatment but then returns.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

"T cell redirecting therapeutic" refers to a molecule containing two or more binding regions, wherein one of the binding regions specifically binds a cell surface antigen on a target cell or tissue and wherein a second binding region of the molecule specifically binds a T cell antigen. Examples of cell surface antigen include a tumor associated antigen, such as BCMA. Examples of T cell antigen include, e.g., CD3. This dual/multi-target binding ability recruits T cells to the target cell or tissue leading to the eradication of the target cell or tissue.

"Therapeutically effective amount" refers to an amount effective, at doses and for periods of time necessary, to achieve a desired therapeutic result. A therapeutically effective amount can vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Treat" or "treatment" refers to both therapeutic treatment and prophylactic or preventative measures, wherein the object is to prevent or slow down (lessen) an undesired physiological change or disorder. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented.

"Tumor cell" or a "cancer cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation can arise from infection with a transforming virus and incorporation of new genomic nucleic acid, uptake of exogenous nucleic acid or it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo.

The numbering of amino acid residues in the antibody constant region throughout the specification is according to the EU index as described in Kabat et al., Sequences of Proteins of Immunological Interest, 5th Ed. Public Health Service, National Institutes of Health, Bethesda, Md. (1991), unless otherwise explicitly stated. Antibody constant chain numbering can be found for example at ImMunoGeneTics website, at IMGT Web resources at IMGT Scientific charts.

Conventional one and three-letter amino acid codes are used herein as shown in Table 1.

TABLE 1

| Amino acid | Three-letter code | One-letter code |
| --- | --- | --- |
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

BCMAxCD3 Bispecific Antibodies and Uses Thereof

The invention is based, at least in part, on the finding that the therapeutic agent teclistamab can be used to treat multiple myeloma in subject that are relapsed or refractory to treatment with a prior anti-cancer therapeutic.

Accordingly, in one general aspect, the invention relates to a method of treating a cancer in a subject, comprising administering a therapeutically effective amount of a BCMAxCD3 bispecific antibody to the subject to treat the cancer, wherein the subject is relapsed or refractory to treatment with a prior anti-cancer therapeutic.

B-cell maturation antigen (BCMA) is a cell membrane bound tumor necrosis factor receptor family member involved in differentiation of B-cells to plasma cells. Expression of BCMA is restricted to the B-cell lineage where it is predominantly expressed in the interfollicular region of germinal centers and on differentiated plasma cells and plasmablasts. BCMA is virtually absent on naïve and memory B cells (Tai and Anderson, Immunotherapy 7: 1187-99, 2015).

Antibodies

Any suitable BCMAxCD3 bispecific antibody known to those skilled in the art in view of the present disclosure can be used in the invention.

Various bispecific antibody formats include formats described herein and recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule, or bispecific antibodies generated by arm exchange. Exemplary bispecific formats include dual targeting molecules include Dual Targeting (DT)-Ig (GSK/Domantis), Two-in-one Antibody (Genentech) and mAb2 (F-Star), Dual Variable Domain (DVD)-Ig (Abbott), DuoBody (Genmab), Ts2Ab (MedImmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS) and Dual Affinity Retargeting Technology (Fc-DART) (MacroGenics), F(ab)2 (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech), Bispecific T Cell Engager (BITE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies. Various formats of bispecific antibodies have been described, for example in Chames and Baty (2009) Curr Opin Drug Disc Dev 12: 276 and in Nunez-Prado et al., (2015) Drug Discovery Today 20(5):588-594.

In some embodiments, the BCMAxCD3 bispecific antibody comprises any one of the BCMA binding domains described in WO2017/031104, the entire content of which is incorporated herein by reference. In some embodiments, the BCMAxCD3 bispecific antibody comprises any one of the CD3 binding domains described in WO2017/031104.

In some embodiments, the BCMAxCD3 bispecific antibody comprises any one of the BCMAxCD3 bispecific antibodies or antigen-binding fragments thereof described in WO2017/031104.

In some embodiments, the BCMAxCD3 bispecific antibody comprises a CD3 binding domain comprising a heavy chain complementarity determining region 1 (HCDR1) of SEQ ID NO: 14, a HCDR2 of SEQ ID NO: 15, a HCDR3 of SEQ ID NO: 16, a light chain complementarity determining region 1 (LCDR1) of SEQ ID NO: 17, a LCDR2 of SEQ ID NO: 18 and a LCDR3 of SEQ ID NO: 19; or a heavy chain variable region (VH) of SEQ ID NO: 20 and a light chain variable region (VL) of SEQ ID NO: 21.

In some embodiments, the BCMAxCD3 bispecific antibody comprises a BCMA binding domain comprising a heavy chain complementarity determining region 1 (HCDR1) of SEQ ID NO: 4, a HCDR2 of SEQ ID NO: 5, a HCDR3 of SEQ ID NO: 6, a LCDR1 of SEQ ID NO: 7, a LCDR2 of SEQ ID NO: 8 and a LCDR3 of SEQ ID NO: 9; or a heavy chain variable region (VH) of SEQ ID NO: 10 and a light chain variable region (VL) of SEQ ID NO: 11.

In some embodiments, the BCMAxCD3 bispecific antibody comprises a first heavy chain (HC1) of SEQ ID NO: 12, a first light chain (LC1) of SEQ ID NO: 13, a second heavy chain (HC2) of SEQ ID NO: 22, and a second light chain (LC2) of SEQ ID NO: 23.

In some embodiments, the BCMAxCD3 bispecific antibody is chimeric, humanized or human.

In some embodiments, the BCMAxCD3 bispecific antibody is an antigen binding fragment. Exemplary antigen binding fragments are Fab, F(ab')2, Fd and Fv fragments.

In some embodiments, the bispecific antibody is an IgG1, an IgG2, an IgG3 or an IgG4 isotype. In preferred embodiments, the bispecific antibody is an IgG4 isotype. An exemplary wild-type IgG4 comprises an amino acid sequence of SEQ ID NO: 24.

SEQ ID NO: 24:
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPSCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK

The bispecific antibody can be of any allotype. It is expected that allotype has no influence on properties of the bispecific antibodies, such as binding or Fc-mediated effector functions. Immunogenicity of therapeutic antibodies is associated with increased risk of infusion reactions and decreased duration of therapeutic response (Baert et al., (2003) N Engl J Med 348:602-08). The extent to which therapeutic antibodies induce an immune response in the host can be determined in part by the allotype of the antibody (Stickler et al., (2011) Genes and Immunity 12:213-21). Antibody allotype is related to amino acid sequence variations at specific locations in the constant region sequences of the antibody. Table 2 shows select IgG1, IgG2 and IgG4 allotypes.

TABLE 2

| | Amino acid residue at position of diversity (residue numbering: EU index) | | | | | | |
|---|---|---|---|---|---|---|---|
| | IgG2 | | IgG4 | | IgG1 | | |
| Allotype | 189 | 282 | 309 | 422 | 214 | 356 | 358 | 431 |
| G2m(n) | T | M | | | | | | |
| G2m(n-) | P | V | | | | | | |
| G2m(n)/(n-nG4m(a) | T | V | L | R | | | | |
| G1m(17) | | | | | K | E | M | A |
| G1m(17,1) | | | | | K | D | L | A |

In some embodiments, the bispecific antibody comprises one or more Fc substitutions that reduces binding of the bispecific antibody to a Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP). The specific substitutions can be made in comparison to the wild-type IgG4 of SEQ ID NO: 24.

Fc positions that can be substituted to reduce binding of the Fc to the activating FcγR and subsequently to reduce effector function are substitutions L234A/L235A on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4, wherein residue numbering is according to the EU index.

Fc substitutions that can be used to reduce CDC are a K322A substitution.

Well-known S228P substitution can further be made in IgG4 antibodies to enhance IgG4 stability.

In some embodiments, the bispecific antibody comprises one or more asymmetric substitutions in a first CH3 domain or in a second CH3 domain, or in both the first CH3 domain and the second CH3 domain.

In some embodiments, the one or more asymmetric substitutions is selected from the group consisting of F405L/K409R, wild-type/F405L_R409K, T366Y/F405A, T366W/F405W, F405W/Y407A, T394W/Y407T, T394S/Y407A, T366W/T394S, F405W/T394S and T366W/T366S_L368A_Y407V, L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F and T350V_L351Y_F405A_Y407V/T350V_T366L_K392L_T394W.

In some embodiments, the BCMAxCD3 bispecific antibody is an IgG4 isotype and comprises phenylalanine at position 405 and arginine at position 409 in a first heavy chain (HC1) and leucine at position 405 and lysine at position 409 in a second heavy chain (HC2), wherein residue numbering is according to the EU Index.

In some embodiments, the BCMAxCD3 bispecific antibody further comprises proline at position 228, alanine at position 234 and alanine at position 235 in both the HC1 and the HC2.

In some embodiments, the BCMAxCD3 bispecific antibody comprises the HC1 of SEQ ID NO: 31, a first light chain (LC1) of SEQ ID NO: 32, the HC2 of SEQ ID NO: 41 and a second light chain (LC2) of SEQ ID NO: 42.

In some embodiments, the BCMAxCD3 bispecific antibody is CC-93269, BI 836909, JNJ-64007957 (teclistamab), or PF-06863135. In preferred embodiments, the BCMAxCD3 bispecific antibody is teclistamab.

Cancers

In some embodiments, the cancer is a hematological malignancy or a solid tumor.

In some embodiments, the hematological malignancy is a multiple myeloma, a smoldering multiple myeloma, a monoclonal gammopathy of undetermined significance (MGUS), an acute lymphoblastic leukemia (ALL), a diffuse large B-cell lymphoma (DLBCL), a Burkitt's lymphoma (BL), a follicular lymphoma (FL), a mantle-cell lymphoma (MCL), Waldenstrom's macroglobulinema, a plasma cell leukemia, a light chain amyloidosis (AL), a precursor B-cell lymphoblastic leukemia, a precursor B-cell lymphoblastic leukemia, an acute myeloid leukemia (AML), a myelodysplastic syndrome (MDS), a chronic lymphocytic leukemia (CLL), a B cell malignancy, a chronic myeloid leukemia (CML), a hairy cell leukemia (HCL), a blastic plasmacytoid dendritic cell neoplasm, Hodgkin's lymphoma, non-Hodgkin's lymphoma, a marginal zone B-cell lymphoma (MZL), a mucosa-associated lymphatic tissue lymphoma (MALT), plasma cell leukemia, anaplastic large-cell lymphoma (ALCL), leukemia or lymphoma.

In preferred embodiments, the hematological malignancy is multiple myeloma. In some embodiments, the subject has a newly diagnosed multiple myeloma. In some embodiments, the subject is relapsed or refractory to treatment with a prior anti-cancer therapeutic, such as a therapeutic used to treat multiple myeloma or other hematological malignancies.

In some embodiments, the subject is refractory or relapsed to treatment with one or more treatments or therapies, such as THALOMID® (thalidomide), REVLIMID® (lenalidomide), POMALYST® (pomalidomide), VELCADE® (bortezomib), NINLARO (ixazomib), KYPROLIS® (carfilzomib), FARADYK® (panobinostat), AREDIA® (pamidronate), ZOMETA® (zoledronic acid), DARZALEX® (daratumumab), elotozumab or melphalan, Xpovio® (Selinexor), Venclexta® (Venetoclax), GSK 916, CAR-T therapies, other BCMA-directed therapies.

Various qualitative and/or quantitative methods can be used to determine relapse or refractory nature of the disease. Symptoms that can be associated are for example a decline or plateau of the well-being of the patient or re-establishment or worsening of various symptoms associated with solid tumors, and/or the spread of cancerous cells in the body from one location to other organs, tissues or cells.

In some embodiments, the multiple myeloma is relapsed or refractory to treatment with an anti-CD38 antibody, selinexor, venetoclax, lenalinomide, bortezomib, pomalidomide, carfilzomib, elotozumab, ixazomib, melphalan or thalidomide, or any combination thereof.

In some embodiments, the multiple myeloma is a high-risk multiple myeloma. Subjects with high-risk multiple myeloma are known to relapse early and have poor prognosis and outcome. Subjects can be classified as having high-risk multiple myeloma is they have one or more of the following cytogenetic abnormalities: t(4;14)(p16;q32), t(14;16)(q32;q23), del17p, 1qAmp, t(4;14)(p16;q32) and t(14;16)(q32;q23), t(4;14)(p16;q32) and del17p, t(14;16)(q32;q23) and del17p, or t(4;14)(p16;q32), t(14;16)(q32;q23) and del17p. In some embodiments, the subject having the high-risk multiple myeloma has one or more chromosomal abnormalities comprising: t(4;14)(p16;q32), t(14;16)(q32;q23), del17p, 1qAmp, t(4;14)(p16;q32) and t(14;16)(q32;q23), t(4;14)(p16;q32) and del17p, t(14;16)(q32;q23) and del17p; or t(4;14)(p16;q32), t(14;16)(q32;q23) and del17p, or any combination thereof.

The cytogenetic abnormalities can be detected for example by fluorescent in situ hybridization (FISH). In chromosomal translocations, an oncogene is translocated to the IgH region on chromosome 14q32, resulting in dysregulation of these genes. t(4;14)(p16;q32) involves translocation of fibroblast growth factor receptor 3 (FGFR3) and multiple myeloma SET domain containing protein (MMSET) (also called WHSC1/NSD2), and t(14;16)(q32;q23)

involves translocation of the MAF transcription factor C-MAF. Deletion of 17p (del17p) involves loss of the p53 gene locus.

Chromosomal rearrangements can be identified using well known methods, for example fluorescent in situ hybridization, karyotyping, pulsed field gel electrophoresis, or sequencing.

Compositions

The BCMAxCD3 bispecific antibody can be formulated as a pharmaceutical composition comprising about 1 mg/mL to about 200 mg/mL antibody.

In some embodiments, the pharmaceutical composition further comprises one or more excipients. In some embodiments, the one or more excipients include, but are not limited to a buffering agent, a sugar, a surfactant, a chelator, or any combination thereof.

In some embodiments, the pharmaceutical composition comprises:

about 20 mg/mL to about 120 mg/mL of the BCMAxCD3 bispecific antibody, such as about 20 mg/mL, about 25 mg/mL, about 30 mg/mL, about 35 mg/mL, about 40 mg/mL, about 45 mg/mL, about 50 mg/mL, about 60 mg/mL, about 70 mg/mL, about 80 mg/mL, about 90 mg/mL, about 100 mg/mL, about 110 mg/mL, about 120 mg/mL, or any value in between, of the BCMAxCD3 bispecific antibody;

about 5 mM to about 20 mM buffering agent, such as about 5 mM, about 10 mM, about 15 mM, about 20 mM, or any value in between, sodium phosphate, $KH_2PO_4$, sodium acetate or sodium citrate;

about 1% w/v to about 20% w/v sugar, such as about 1% w/v, about 2% w/v, about 3% w/v, about 4% w/v, about 5% w/v, about 6% w/v, about 7% w/v, about 8% w/v, about 9% w/v, about 10% w/v, about 15% w/v, about 20% w/v, or any value in between, glucose, sucrose or cellobiose;

about 0.01% w/v to about 2% w/v surfactant, such as about 0.01% w/v, about 0.02% w/v, about 0.03% w/v, about 0.04% w/v, about 0.05% w/v, about 0.06% w/v, about 0.07% w/v, about 0.08% w/v, about 0.09% w/v, about 0.1% w/v, about 0.5% w/v, about 1% w/v, about 1.5% w/v, about 2% w/v, or any value in between, polysorbate 80 (PS-80) or PS-20; and about 5 mM to about 40 mM, such as about 5 mM, about 10 mM, about 15 mM, about 20 mM, about 25 mM, about 30 mM, about 35 mM, about 40 mM, or any value in between, ethylenediaminetetraacetic acid (EDTA) or an edetate salt, at a pH of about 5-6, such as about 5, about 5.1, about 5.2, about 5.3, about 5.4, about 5.5, about 5.6, about 5.7, about 5.8, about 5.9, about 6, or any value in between.

In some embodiments, the pharmaceutical composition further comprises about 0.1 mg/mL to about 5 mg/mL amino acid, such as about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 2 mg/mL, about 3 mg/mL, about 4 mg/mL, about 5 mg/mL, or any value in between, methionine or arginine.

In one embodiment, a pharmaceutical composition useful for the invention comprises BCMAxCD3 bispecific antibody, such as teclistamab, 20 mM sodium phosphate, 10% weight/volume (w/v) sucrose, 0.06% (w/v) PS80, and 25 µg/mL EDTA at pH 5.4.

In another embodiment, a pharmaceutical composition useful for the invention comprises BCMAxCD3 bispecific antibody, such as teclistamab, 10 to 15 mM sodium acetate, 8% (w/v) sucrose, 0.04% (w/v) PS20, and 20 µg/mL EDTA at pH 5.2.

In another embodiment, a pharmaceutical composition useful for the invention comprises BCMAxCD3 bispecific antibody, such as teclistamab, 15 mM $KH_2PO_4$, 10% (w/v) cellobiose, 0.05% (w/v) PS20, and 25 µg/mL EDTA at pH 5.1.

Administration

In some embodiments, the BCMAxCD3 bispecific antibody is administered by an intravenous injection.

In some embodiments, the BCMAxCD3 bispecific antibody is administered by a subcutaneous injection.

The dose of the BCMAxCD3 bispecific antibody given to a subject having cancer, such as multiple myeloma, is sufficient to alleviate or at least partially arrest the disease being treated ("therapeutically effective amount") and includes from about 0.1 µg/kg to about 6000 µg/kg, e.g. about 0.3 µg/kg to about 5000 µg/kg, about 0.1 µg/kg to about 3000 µg/kg, about 0.2 µg/kg to about 3000 µg/kg, about 0.3 µg/kg to about 3000 µg/kg, about 0.6 µg/kg to about 3000 µg/kg, about 1.2 µg/kg to about 3000 µg/kg, about 19.2 µg/kg to about 3000 µg/kg, about 35 µg/kg to about 3000 µg/kg, about 80 µg/kg to about 3000 µg/kg, about 100 µg/kg to about 3000 µg/kg, about 270 µg/kg to about 3000 µg/kg, about 720 µg/kg to about 3000 µg/kg, about 0.1 µg/kg to about 1800 µg/kg, about 0.2 µg/kg to about 1800 µg/kg, about 0.3 µg/kg to about 1800 µg/kg, about 0.6 µg/kg to about 1800 µg/kg, about 1.2 µg/kg to about 1800 µg/kg, about 19.2 µg/kg to about 1800 µg/kg, about 35 µg/kg to about 1800 µg/kg, about 80 µg/kg to about 1800 µg/kg, about 100 µg/kg to about 1800 µg/kg, about 270 µg/kg to about 1800 µg/kg, about 720 µg/kg to about 1800 µg/kg, about 0.1 µg/kg to about 1500 µg/kg, about 0.2 µg/kg to about 1500 µg/kg, about 0.3 µg/kg to about 1500 µg/kg, about 0.6 µg/kg to about 1500 µg/kg, about 1.2 µg/kg to about 1500 µg/kg, about 19.2 µg/kg to about 1500 µg/kg, about 35 µg/kg to about 1500 µg/kg, about 80 µg/kg to about 1500 µg/kg, about 100 µg/kg to about 1500 µg/kg, about 270 µg/kg to about 1500 µg/kg, about 720 µg/kg to about 1500 µg/kg, about 0.1 µg/kg to about 850 µg/kg, about 0.2 µg/kg to about 850 µg/kg, about 0.3 µg/kg to about 850 µg/kg, about 0.6 µg/kg to about 850 µg/kg, about 1.2 µg/kg to about 850 µg/kg, about 19.2 µg/kg to about 850 µg/kg, about 35 µg/kg to about 850 µg/kg, about 80 µg/kg to about 850 µg/kg, about 100 µg/kg to about 850 µg/kg, about 270 µg/kg to about 850 µg/kg, about 720 µg/kg to about 850 µg/kg, about 0.1 µg/kg to about 720 µg/kg, about 0.2 µg/kg to about 720 µg/kg, about 0.3 µg/kg to about 720 µg/kg, about 0.6 µg/kg to about 720 µg/kg, about 720 µg/kg, about 1.2 µg/kg to about 720 µg/kg, about 19.2 µg/kg to about 720 µg/kg, about 35 µg/kg to about 720 µg/kg, about 80 µg/kg to about 720 µg/kg, about 100 µg/kg to about 720 µg/kg, about 270 µg/kg to about 720 µg/kg, about 720 µg/kg to about 720 µg/kg, about 0.1 µg/kg to about 270 µg/kg, about 0.2 µg/kg to about 270 µg/kg, about 0.3 µg/kg to about 270 µg/kg, about 0.6 µg/kg to about 270 µg/kg, about 1.2 µg/kg to about 270 µg/kg, about 19.2 µg/kg to about 270 µg/kg, about 35 µg/kg to about 270 µg/kg, about 80 µg/kg to about 270 µg/kg, about 100 µg/kg to about 270 µg/kg, about 270 µg/kg to about 270 µg/kg, about 720 µg/kg to about 270 µg/kg, about 0.1 µg/kg to about 100 µg/kg, about 0.2 µg/kg to about 100 µg/kg, about 0.3 µg/kg to about 100 µg/kg, about 0.6 µg/kg to about 100 µg/kg, about 1.2 µg/kg to about 100 µg/kg, about 19.2 µg/kg to about 100 µg/kg, about 35 µg/kg to about 100 µg/kg, about 80 µg/kg to about 100 µg/kg, about 100 µg/kg to about 100 µg/kg, about 270 µg/kg to about 100 µg/kg, about 720 µg/kg to about 100 µg/kg of the antibody. Suitable doses include, e.g., about 0.1 µg/kg, about 0.2 µg/kg, about 0.3 µg/kg, about 0.6 µg/kg, about 1.2 µg/kg, about 2.4 µg/kg, about 4.8 µg/kg, about 9.6

μg/kg, about 19.2 μg/kg, about 20 μg/kg, about 35 μg/kg, about 38.4 μg/kg, about 40 μg/kg, about 50 μg/kg, about 57.6 μg/kg, about 60 μg/kg, about 80 μg/kg, about 100 μg/kg, about 120 μg/kg, about 180 μg/kg, about 240 μg/kg, about 270 μg/kg, about 300 μg/kg, about 720 μg/kg, about 850 μg/kg, about 1000 μg/kg, about 1100 μg/kg, about 1200 μg/kg, about 1300 μg/kg, about 1400 μg/kg, about 1500 μg/kg, about 1600 μg/kg, about 1700 μg/kg, about 1800 μg/kg, about 2000 μg/kg, about 2500 μg/kg, about 3000 μg/kg, about 3500 μg/kg, about 4000 μg/kg, about 4500 μg/kg, about 5000 μg/kg, about 5500 μg/kg, about 6000 μg/kg, or any dose in between.

A fixed unit dose of the BCMAxCD3 bispecific antibody can also be given, for example, 50, 100, 200, 500, or 1000 mg, or any value in between, or the dose can be based on the patient's surface area, e.g., 500, 400, 300, 250, 200, or 100 mg/m$^2$, or any value in between. Usually 1 to 8 doses, (e.g., 1, 2, 3, 4, 5, 6, 7, or 8) can be administered to treat a cancer, such as a multiple myeloma, but 9, 10, 11, 12, 13, 14, 15, 16, 17, 18, 19, 20, or more doses can be given.

The administration of the BCMAxCD3 bispecific antibody can be repeated after one day, two days, three days, four days, five days, six days, one week, two weeks, three weeks, one month, five weeks, six weeks, seven weeks, two months, three months, four months, five months, six months, or longer. Repeated courses of treatment are also possible, as is chronic administration. The repeated administration can be at the same dose or at a different dose. For example, the BCMAxCD3 bispecific antibody can be administered at a first dose at weekly intervals for a certain number of weeks, followed by administration at a second dose every two weeks for an additional certain number of weeks, followed by administration at a third dose every week for an additional certain number of weeks.

The BCMAxCD3 bispecific antibody can be administered by maintenance therapy, such as, e.g., once a week for a period of 6 months or more. For example, the BCMAxCD3 bispecific antibody can be provided as a daily dosage in an amount of about 0.1 μg/kg to about 6000 μg/kg, e.g. about 0.2 μg/kg to about 3000 μg/kg, about 0.2 μg/kg to about 2000 μg/kg, about 0.2 μg/kg to about 1500 μg/kg, about 0.3 μg/kg to about 1500 μg/kg, about 0.6 μg/kg to about 720 μg/kg, about 1.2 μg/kg to about 270 μg/kg, about 19.2 μg/kg to about 720 μg/kg, about 35 μg/kg to about 850 μg/kg, about 270 μg/kg to about 720 μg/kg, of the antibody per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19, or 20 after initiation of treatment, or any combination thereof, using single or divided doses of every 24, 12, 8, 6, 4, or 2 hours, or any combination thereof.

In one embodiment, the BCMAxCD3 bispecific antibody is administered intraveneously once a week at a single dose. For example, the BCMAxCD3 bispecific antibody can be administered intravenously once a week in an amount of about 0.1 μg/kg, about 0.2 μg/kg, about 0.3 μg/kg, about 0.6 μg/kg, about 1.2 μg/kg, about 2.4 μg/kg, about 4.8 μg/kg, about 9.6 μg/kg, about 19.2 μg/kg, about 20 μg/kg, about 35 μg/kg, about 38.4 μg/kg, about 40 μg/kg, about 50 μg/kg, about 57.6 μg/kg, about 60 μg/kg, about 80 μg/kg, about 100 μg/kg, about 120 μg/kg, about 180 μg/kg, about 240 μg/kg, about 270 μg/kg, about 300 μg/kg, about 720 μg/kg, about 850 μg/kg, about 1000 μg/kg, about 1100 μg/kg, about 1200 μg/kg, about 1300 μg/kg, about 1400 μg/kg, about 1500 μg/kg, about 1500 μg/kg, about 1600 μg/kg, about 1700 μg/kg, about 1800 μg/kg, or any dose in between.

In one embodiment, the BCMAxCD3 bispecific antibody is administered intraveneously twice a week at a single dose. For example, the BCMAxCD3 bispecific antibody can be administered intravenously twice a week in an amount of about 0.1 μg/kg, about 0.2 μg/kg, about 0.3 μg/kg, about 0.6 μg/kg, about 1.2 μg/kg, about 2.4 μg/kg, about 4.8 μg/kg, about 9.6 μg/kg, about 19.2 μg/kg, about 20 μg/kg, about 35 μg/kg, about 38.4 μg/kg, about 40 μg/kg, about 50 μg/kg, about 57.6 μg/kg, about 60 μg/kg, about 80 μg/kg, about 100 μg/kg, about 120 μg/kg, about 180 μg/kg, about 240 μg/kg, about 270 μg/kg, about 300 μg/kg, about 720 μg/kg, about 850 μg/kg, about 1000 μg/kg, about 1100 μg/kg, about 1200 μg/kg, about 1300 μg/kg, about 1400 μg/kg, about 1500 μg/kg, about 1500 μg/kg, about 1600 μg/kg, about 1700 μg/kg, about 1800 μg/kg, or any dose in between.

In one embodiment, the BCMAxCD3 bispecific antibody is administered intraveneously at a step-up (or "priming") dose, followed by weekly administration at a higher dose. For example, the BCMAxCD3 bispecific antibody can be administered intravenously at a step-up dose of about 0.1 μg/kg, about 0.2 μg/kg, about 0.3 μg/kg, about 0.6 μg/kg, about 1.2 μg/kg, about 2.4 μg/kg, about 4.8 μg/kg, about 9.6 μg/kg, about 10 μg/kg, about 19.2 μg/kg, about 20 μg/kg, or any dose in between, followed by weekly intravenous administration at a dose of about 35 μg/kg, about 38.4 μg/kg, about 40 μg/kg, about 50 μg/kg, about 57.6 μg/kg, about 60 μg/kg, about 80 μg/kg, or any dose in between.

In one embodiment, the BCMAxCD3 bispecific antibody is administered intraveneously at a step-up dose, followed by administration at a higher step-up dose, followed by weekly administration at a third, higher dose. For example, the BCMAxCD3 bispecific antibody can be administered intravenously at a step-up dose of about 0.1 μg/kg, about 0.2 μg/kg, about 0.3 μg/kg, about 0.6 μg/kg, about 1.2 μg/kg, about 2.4 μg/kg, about 4.8 μg/kg, about 9.6 μg/kg, about 10 μg/kg, about 19.2 μg/kg, about 20 μg/kg, or any dose in between, followed by intravenous administration at a step-up dose of about 35 μg/kg, about 38.4 μg/kg, about 40 μg/kg, about 50 μg/kg, about 57.6 μg/kg, about 60 μg/kg, about 80 μg/kg, or any dose in between, followed by weekly intravenous administration at a dose of about 80 μg/kg, about 100 μg/kg, about 120 μg/kg, about 180 μg/kg, about 240 μg/kg, about 270 μg/kg, or any dose in between.

In one embodiment, the BCMAxCD3 bispecific antibody is administered intraveneously at a step-up dose, followed by administration at a higher step-up dose, followed by administration at a third, higher step-up dose, followed by weekly administration at a fourth, higher dose. For example, the BCMAxCD3 bispecific antibody can be administered intravenously at a step-up dose of about 0.1 μg/kg, about 0.2 μg/kg, about 0.3 μg/kg, about 0.6 μg/kg, about 1.2 μg/kg, about 2.4 μg/kg, about 4.8 μg/kg, about 9.6 μg/kg, about 10 μg/kg, about 19.2 μg/kg, about 20 μg/kg, or any dose in between, followed by intravenous administration at a step-up dose of about 35 μg/kg, about 38.4 μg/kg, about 40 μg/kg, about 50 μg/kg, about 57.6 μg/kg, about 60 μg/kg, about 80 μg/kg, or any dose in between, followed by intravenous administration at a step-up dose of about 80 μg/kg, about 100 μg/kg, about 120 μg/kg, about 180 μg/kg, about 240 μg/kg, about 270 μg/kg, or any dose in between, followed by weekly intravenous administration at a dose of about 300 μg/kg, about 720 μg/kg, about 850 μg/kg, about 1000 μg/kg, about 1100 μg/kg, about 1200 μg/kg, about 1300 μg/kg, about 1400 μg/kg, about 1500 μg/kg, about 1600 μg/kg, about 1700 μg/kg, about 1800 μg/kg, or any dose in between.

In one embodiment, the BCMAxCD3 bispecific antibody is administered subcutaneously once a week at a single dose.

For example, the BCMAxCD3 bispecific antibody can be administered subcutaneously once a week in an amount of about 0.1 µg/kg, about 0.2 µg/kg, about 0.3 µg/kg, about 0.6 µg/kg, about 1.2 µg/kg, about 2.4 µg/kg, about 4.8 µg/kg, about 9.6 µg/kg, about 19.2 µg/kg, about 20 µg/kg, about 35 µg/kg, about 38.4 µg/kg, about 40 µg/kg, about 50 µg/kg, about 57.6 µg/kg, about 60 µg/kg, about 80 µg/kg, about 100 µg/kg, about 120 µg/kg, about 180 µg/kg, about 240 µg/kg, about 270 µg/kg, about 300 µg/kg, about 720 µg/kg, about 850 µg/kg, about 1000 µg/kg, about 1100 µg/kg, about 1200 µg/kg, about 1300 µg/kg, about 1400 µg/kg, about 1500 µg/kg, about 1500 µg/kg, about 1600 µg/kg, about 1700 µg/kg, about 1800 µg/kg, about 2000 µg/kg, about 2500 µg/kg, about 3000 µg/kg, about 3500 µg/kg, about 4000 µg/kg, about 4500 µg/kg, about 5000 µg/kg, or any dose in between.

In one embodiment, the BCMAxCD3 bispecific antibody is administered subcutaneously at a step-up dose, followed by weekly administration at a higher dose. For example, the BCMAxCD3 bispecific antibody can be administered subcutaneously at a step-up dose of about 10 µg/kg, about 20 µg/kg, about 35 µg/kg, about 40 µg/kg, about 50 µg/kg, about 60 µg/kg, or any dose in between, followed by weekly subcutaneously administration at a dose of about 80 µg/kg, about 100 µg/kg, about 240 µg/kg, about 300 µg/kg, or any dose in between.

In one embodiment, the BCMAxCD3 bispecific antibody is administered subcutaneously at a step-up dose, followed by administration at a higher step-up dose, followed by weekly administration at a third, higher dose. For example, the BCMAxCD3 bispecific antibody can be administered subcutaneously at a step-up dose of about 10 µg/kg, about 20 µg/kg, about 35 µg/kg, about 40 µg/kg, about 50 µg/kg, about 60 µg/kg, or any dose in between, followed by subcutaneously administration at a step-up dose of about 80 µg/kg, about 100 µg/kg, about 240 µg/kg, about 300 µg/kg, or any dose in between, followed by weekly subcutaneously administration at a dose of about 240 µg/kg, about 720 µg/kg, about 1100 µg/kg, about 1200 µg/kg, about 1300 µg/kg, about 1400 µg/kg, about 1500 µg/kg, about 1600 µg/kg, about 1700 µg/kg, about 1800 µg/kg, about 2000 µg/kg, about 2500 µg/kg, about 3000 µg/kg, or any dose in between.

In some embodiments, the BCMAxCD3 bispecific antibody is administered for a time sufficient to achieve complete response, stringent complete response, very good partial response, partial response, minimal response or stable disease status, and can be continued until disease progression or lack of patient benefit. The disease status can be determined by any method suitable method known to those skilled in the art in view of the present disclosure, including, e.g., analysis of serum and urine monocolonal protein concentrations, M-protein levels, BCMA levels.

In some embodiments, the BCMAxCD3 bispecific antibody is administered for a time sufficient to achieve complete response that is characterized by negative minimal residual disease (MRD) status. Negative MRD status can be determined by any method suitable method known to those skilled in the art in view of the present disclosure. In some embodiments, negative MRD status is determined using next generation sequencing (NGS). In some embodiments, negative MRD status is determined at $10^{-4}$ cells, $10^{-5}$ cells, or $10^{-6}$ cells.

The BCMAxCD3 bispecific antibody can also be administered prophylactically in order to reduce the risk of developing cancer, such as multiple myeloma, delay the onset of the occurrence of an event in cancer progression, and/or reduce the risk of recurrence when the cancer is in remission.

In some embodiments, the method further comprises administering to the subject one or more anti-cancer therapies.

In some embodiments, the one or more anti-cancer therapies is selected from the group consisting of an autologous stem cell transplant (ASCT), radiation, surgery, a chemotherapeutic agent, an immunomodulatory agent and a targeted cancer therapy.

In some embodiments, the one or more anti-cancer therapies is selected from the group consisting of selinexor, venetoclax, lenalidomide, thalidomide, pomalidomide, bortezomib, carfilzomib, elotozumab, ixazomib, melphalan, dexamethasone, vincristine, cyclophosphamide, hydroxydaunorubicin, prednisone, rituximab, imatinib, dasatinib, nilotinib, bosutinib, ponatinib, bafetinib, saracatinib, selinexor, venetoclax, tozasertib or danusertib, cytarabine, daunorubicin, idarubicin, mitoxantrone, hydroxyurea, decitabine, cladribine, fludarabine, topotecan, etoposide 6-thioguanine, corticosteroid, methotrexate, 6-mercaptopurine, azacitidine, arsenic trioxide and all-trans retinoic acid, or any combination thereof.

While having described the invention in general terms, the embodiments of the invention will be further disclosed in the following examples that should not be construed as limiting the scope of the claims.

EMBODIMENTS

1) A method of treating a cancer in a subject in need thereof, comprising administering a therapeutically effective amount of a BCMAxCD3 bispecific antibody or antigen binding fragment thereof, to the subject to treat the cancer, wherein the subject is relapsed or refractory to treatment with a prior anti-cancer treatment.
2) The method of embodiment 1, wherein the BCMAxCD3 bispecific antibody or antigen binding fragment thereof comprises a BCMA binding domain comprising the HCDR1 of SEQ ID NO: 4, the HCDR2 of SEQ ID NO: 5, the HCDR3 of SEQ ID NO: 6, the LCDR1 of SEQ ID NO: 7, the LCDR2 of SEQ ID NO: 8 and the LCDR3 of SEQ ID NO: 9, and a CD3 binding domain comprising the HCDR1 of SEQ ID NO: 14, the HCDR2 of SEQ ID NO: 15, the HCDR3 of SEQ ID NO: 16, the LCDR1 of SEQ ID NO: 17, the LCDR2 of SEQ ID NO: 18 and the LCDR3 of SEQ ID NO: 19.
3) The method of embodiment 1 or 2, wherein the BCMA binding domain comprises a heavy chain variable region (VH) having the amino acid sequence of SEQ ID NO: 10 and a light chain variable region (VL) having the amino acid sequence of SEQ ID NO: 11, and the CD3 biding domain comprises a heavy chain variable region (VH) 15 having the amino acid sequence of SEQ ID NO: 20 and a light chain variable region (VL) having the amino acid sequence of SEQ ID NO: 21.
4) The method of any one of embodiments 1 to 3, wherein the BCMA×CD3 bispecific antibody is an IgG4 isotype and comprises phenylalanine at position 405 and arginine at position 409 in the HC1 and leucine at position 405 and lysine at position 409 in the HC2, wherein residue numbering is according to the EU Index.
5) The method of any one of embodiments 1 to 4, wherein the BCMAxCD3 bispecific antibody further comprises proline at position 228, alanine at position 234 and alanine at position 235 in both the HC1 and the HC2.

6) The method of any one of embodiments 1 to 5, wherein the BCMAxCD3 bispecific antibody comprises a first heavy chain (HC1) having the amino acid sequence of SEQ ID NO: 12, the a first light chain (LC1) having the amino acid sequence of SEQ ID NO: 13, a second heavy chain (HC2) having the amino acid sequence of SEQ ID NO: 22 and a second light chain (LC2) having the amino acid sequence of SEQ ID NO: 23.
7) The method of any one of embodiments 1 to 6, wherein the BCMAxCD3 bispecific antibody is teclistamab.
8) The method of any one of embodiments 1 to 7, wherein the BCMAxCD3 bispecific antibody is administered intravenously or subcutaneously.
9) The method of embodiment 8, wherein the BCMAxCD3 bispecific antibody is administered intravenously at a dose of about 0.2 µg/kg weekly to about 1500 µg/kg weekly, such as about 35 µg/kg weekly to about 850 µg/kg weekly, 270 µg/kg to about 720 µg/kg weekly, or 19.2-720 µg/kg weekly; or about 0.1 to 100 µg/kg biweekly, such as about 0.2 to 50 µg/kg biweekly, or 0.3-19.2 µg/kg biweekly.
10) The method of embodiment 8, wherein the BCMAxCD3 bispecific antibody is administered subcutaneously at a dose of about 0.2 µg/kg weekly to about 3000 µg/kg weekly, such as about 80-3000 µg/kg weekly, about 100 µg/kg weekly to about 1800 µg/kg weekly, about 720 µg/kg to 1500 µg/kg weekly, such as about 1000, 1100, 1200, 1300, 1400, 1500, 1600, 1700 or 1800 µg/kg weekly.
11) The method of any one of embodiments 1 to 10, wherein the BCMAxCD3 bispecific antibody is administered for a time sufficient to achieve complete response, stringent complete response, very good partial response, partial response, minimal response or stable disease status, and can be continued until disease progression or lack of patient benefit.
12) The method of embodiment 11, wherein the BCMAxCD3 bispecific antibody is administered for a time sufficient to achieve complete response that is characterized by negative minimal residual disease (MRD) status, preferably negative MRD status at $10^{-6}$ cells, as determined by next generation sequencing (NGS).
13) The method of any one of embodiments 1 to 12, wherein the cancer is a hematological malignancy.
14) The method of embodiment 13, wherein the hematological malignancy is a multiple myeloma.
15) The method of any one of embodiments 1 to 14, wherein the subject is refractory or relapsed to treatment with an anti-CD38 antibody, selinexor, venetoclax, lenalinomide, bortezomib, pomalidomide, carfilzomib, elotozumab, ixazomib, melphalan or thalidomide, or any combination thereof
16) The method of any one of embodiments 1 to 15, wherein the subject is a human subject, preferably the prior anti-cancer treatment comprises administering to the human subject at least one of a proteasome inhibitor and immunomodulatory drug, such as bortezomib, carfilzomib, lenalidomide, or pomalidomide.
17) The method of any one of embodiments 1-16, further comprising administering to the subject one or more additional anti-cancer therapies.
18) The method of embodiment 17, wherein the one or more additional anti-cancer therapies are selected from the group consisting of an autologous stem cell transplant (ASCT), radiation, surgery, a chemotherapeutic agent, a CAR-T therapy, an immunomodulatory agent and a targeted cancer therapy.
19) The method of embodiment 18, wherein the one or more anti-cancer therapies are selected from the group consisting of selinexor, venetoclax, lenalidomide, thalidomide, pomalidomide, bortezomib, carfilzomib, elotozumab, ixazomib, melphalan, prednisone or dexamethasone, or any combination thereof
20) The method of any one of embodiments 1-19, wherein the treatment achieves an overall response rate of at least 60%, such as 60%, 65%, 70%, 75%, 80%, 85%, 90%, 95% or more in the treated subjects.
21) The method of any one of embodiments 1-20, wherein the treatment achieves 15% or more, such as 15%, 16%, 17%, 18%, 19%, 20%, 21%, 22%, 23%, 24%, 25% or more complete response in the treated subjects.

EXAMPLES

The following examples are provided to further describe some of the embodiments disclosed herein. The examples are intended to illustrate, not to limit, the disclosed embodiments.

Antibodies and Reagents

Anti-BCMA/anti-CD3 antibody teclistamab (also called JNJ-64007957, JNJ-957 or JNJ-7957) (described in WO2017031104A1) was made by Janssen Pharmaceuticals. Teclistamab comprises a BCMA binding arm BCMB69 and a CD3 binding arm CD3B219, the amino acid sequences of which are shown in Table 3 and Table 4, respectively.

TABLE 3

Sequences of BCMA binding arm of Teclistamab

| | Region | Sequence | SEQ ID NO: |
|---|---|---|---|
| BCMB69 | HCDR1 | SGSYFWG | 4 |
| | HCDR2 | SIYYSGITYYNPSLKS | 5 |
| | HCDR3 | HDGAVAGLFDY | 6 |
| | LCDR1 | GGNNIGSKSVH | 7 |
| | LCDR2 | DDSDRPS | 8 |
| | LCDR3 | QVWDSSSDHVV | 9 |
| | VH | QLQLQESGPGLVKPSETLSLTCTVSGGSISSGSYFWGWIRQPPGKGLEWIGSIYYSGITYYNPSLKSRVTISVDTSKNQFSLKLSSVTAADTAVYYCARHDGAVAGLFDYWGQGTLVTVSS | 10 |
| | VL | SYVLTQPPSVSVAPGQTARITCGGNNIGSKSVHWYQQPPGQAPVVVVYDDSDRPSGIPERFSGSNSGNTATLTISRVEAGDEAVYYCQVWDSSSDHVVFGGGTKLTVLGQP | 11 |

TABLE 3-continued

Sequences of BCMA binding arm of Teclistamab

| Region | Sequence | SEQ ID NO: |
|---|---|---|
| HC | QLQLQESGPGLVKPSETLSLTCTVSGGSISSGSY FWGWIRQPPGKGLEWIGSIYYSGITYYNPSLKS RVTISVDTSKNQFSLKLSSVTAADTAVYYCAR HDGAVAGLFDYWGQGTLVTVSSASTKGPSVFP LAPCSRSTSESTAALGCLVKDYFPEPVTVSWNS GALTSGVHTFPAVLQSSGLYSLSSVVTVPSSSL GTKTYTCNVDHKPSNTKVDKRVESKYGPPCPP CPAPEAAGGPSVFLFPPKPKDTLMISRTPEVTCV VVDVSQEDPEVQFNWYVDGVEVHNAKTKPRE EQFNSTYRVVSVLTVLHQDWLNGKEYKCKVS NKGLPSSIEKTISKAKGQPREPQVYTLPPSQEEM TKNQVSLTCLVKGFYPSDIAVEWESNGQPENN YKTTPPVLDSDGSFFLYSRLTVDKSRWQEGNV FSCSVMHEALHNHYTQKSLSLSLGK | 12 |
| LC | SYVLTQPPSVSVAPGQTARITCGGNNIGSKSVH WYQQPPGQAPVVVVYDDSDRPSGIPERFSGSN SGNTATLTISRVEAGDEAVYYCQVWDSSSDHV VFGGGTKLTVLGQPKAAPSVTLFPPSSEELQAN KATLVCLISDFYPGAVTVAWKGDSSPVKAGVE TTTPSKQSNNKYAASSYLSLTPEQWKSHRSYSC QVTHEGSTVEKTVAPTECS | 13 |

TABLE 4

Sequences of CD3 binding arm of Teclistamab

| | Region | Sequence | SEQ ID NO: |
|---|---|---|---|
| CD3B219 | HCDR1 | TYAMN | 14 |
| | HCDR2 | RIRSKYNNYATYYAASVKG | 15 |
| | HCDR3 | HGNFGNSYVSWFAY | 16 |
| | LCDR1 | RSSTGAVTTSNYAN | 17 |
| | LCDR2 | GTNKRAP | 18 |
| | LCDR3 | ALWYSNLWV | 19 |
| | VH | EVQLVESGGGLVQPGGSLRLSCAASGFTFNT YAMNWVRQAPGKGLEWVARIRSKYNNYAT YYAASVKGRFTISRDDSKNSLYLQMNSLKTE DTAVYYCARHGNFGNSYVSWFAYVVGQGTL VTVSS | 20 |
| | VL | QTVVTQEPSLTVSPGGTVTLTCRSSTGAVTT SNYANWVQQKPGQAPRGLIGGTNKRAPGTP ARFSGSLLGGKAALTLSGVQPEDEAEYYCAL WYSNLWVFGGGTKLTVLGQP | 21 |
| | HC | EVQLVESGGGLVQPGGSLRLSCAASGFTFNT YAMNWVRQAPGKGLEWVARIRSKYNNYAT YYAASVKGRFTISRDDSKNSLYLQMNSLKTE DTAVYYCARHGNFGNSYVSWFAYVVGQGTL VTVSSASTKGPSVFPLAPCSRSTSESTAALGC LVKDYFPEPVTVSWNSGALTSGVHTFPAVL QSSGLYSLSSVVTVPSSSLGTKTYTCNVDHK PSNTKVDKRVESKYGPPCPPCPAPEAAGGPS VFLFPPKPKDTLMISRTPEVTCVVVDVSQED PEVQFNWYVDGVEVHNAKTKPREEQFNSTY RVVSVLTVLHQDWLNGKEYKCKVSNKGLPS SIEKTISKAKGQPREPQVYTLPPSQEEMTKNQ VSLTCLVKGFYPSDIAVEWESNGQPENNYKT TPPVLDSDGSFLLYSKLTVDKSRWQEGNVFS CSVMHEALHNHYTQKSLSLSLGK | 22 |
| | LC | QTVVTQEPSLTVSPGGTVTLTCRSSTGAVTT SNYANWVQQKPGQAPRGLIGGTNKRAPGTP ARFSGSLLGGKAALTLSGVQPEDEAEYYCAL WYSNLWVFGGGTKLTVLGQPKAAPSVTLFP PSSEELQANKATLVCLISDFYPGAVTVAWKA DSSPVKAGVETTTPSKQSNNKYAASSYLSLT PEQWKSHRSYSCQVTHEGSTVEKTVAPTECS | 23 |

Example 1: Nonclinical Pharmacology Studies of Teclistamab

Teclistamab is being developed for the treatment of multiple myeloma (MM). It is a humanized antibody that specifically recognizes the BCMA receptor, which is expressed at a high level in multiple myeloma cells, and the cluster of differentiation 3 (CD3) receptor complex expressed on T lymphocytes (T cells) (Laabi et al., *Nucleic Acids Res.* 1994; 22(7):1147-54).

A. Effect on BCMA Signaling and Ligand Binding

BCMA mediates downstream signaling such as NF-κB and p38 through its ligands APRIL and BAFF. Treatment with teclistamab led to no agonistic activation of BCMA-mediated signaling with no signs of increased phosphorylation on p38 (data not shown). Similarly, treatment with teclistamab in the presence of recombinant APRIL or BAFF protein showed up to 50% inhibition of p38 phosphorylation at 1 μg/mL of teclistamab and ligands (data not shown).

B. Teclistamab-Mediated T Cell Dependent Cytotoxicity of Multiple Myeloma Cell Lines Treatment with teclistamab led to T cell-mediated cytotoxicity after 48 hours of incubation with BCMA+ multiple myeloma cell lines (H929, MM.1R, and RPMI8226) and T cells from 6 different healthy donors (average $EC_{50}$ [$EC_{20}$] values for H929, MM.1R, RPMI8226 were 0.58 [0.34], 0.07 [0.04], and 0.70 [0.25] nM respectively); importantly, there was no lysis of the BCMA-negative cell line MV4-11 or with control bispecific antibodies (unrelated arm×CD3 or BCMA×unrelated arm; see FIG. 1). For FIG. 1, Teclistamab and negative control molecules were incubated at increasing concentrations with multiple myeloma cell lines and healthy donor pan T cells at an E:T ratio of 5:1 in the presence of fragment crystallizable blocker. After 48 hours of incubation the percentage cytotoxicity was then assessed by flow cytometry and $EC_{50}$s calculated using GraphPad Prism software. The data shown in FIG. 1 represents the average of 6 different T cell donors.

BCMA was also found as a shedded, soluble protein in the blood of multiple myeloma patients at a concentration of 15.27 nM sBCMA; data not shown). To assess the impact of sBCMA on the ability of teclistamab to induce cell death in multiple myeloma cells, recombinant sBCMA protein was spiked in the cytotoxicity assay, and no impact on cell killing up to 56 nM of sBCMA was observed, whereas a 3× higher concentration of sBCMA (167 nM) had a moderate reduction in potency (2×) suggesting that shed BCMA in the blood is unlikely to impact the efficacy of teclistamab (data not shown).

C. Teclistamab-Mediated T Cell Activation in the Presence of BCMA+ Cell Lines In Vitro Teclistamab-induced expression of the T cell activation marker, CD25, on T cells from different healthy donors in the cytotoxicity assays described above. Teclistamab (but not negative control null molecules) induced potent T cell activation when incubated with BCMA+ multiple myeloma cells and healthy donor pan T cells at the $EC_{50}$ for T cell activation (average $EC^{50}$ [$EC^{20}$] values for H929, MM.1R, and RPMI8226 were 0.50 [0.30], 0.15 [0.06], and 0.36 [0.15] nM, respectively), while this was not the case in the negative control cells (MV4 11), except at the top concentration of 532 nM with a marginal up-regulation of CD25 expression (data not shown). Furthermore, teclistamab did not cause activation of T cells in the absence of target BCMA+ cells, demonstrating the specificity of T cell activation except at concentrations >100 nM (data not shown). Cytokine concentrations for interferon (IFN)-γ, TNF-α, interleukin (IL)-2, IL-6, IL-8, and IL-10 were determined from RPMI8226 and H929 assays, and respective values were calculated for each donor (average $EC_{50}$ and $EC_{20}$ values for RPMI8226 cells were IFN γ: 1.61 [0.97], TNF-α: 18.17 [0.80], IL-2: 2.00 [1.07], IL-6: 1.33 [0.71], IL-8: 0.50 [0.26], and IL-10: 0.78 [0.50]; and average $EC_{50}$ and $EC_{20}$ values for H929 cells were IFN-γ: 2.82 [1.94], TNF-α: 3.75 [2.04], IL-2: 4.09 [3.29], IL-6: 1.44 [0.82], IL-8: 2.19 [1.52], and IL-10: 1.91 [1.56]) (data not shown).

Figure 2:
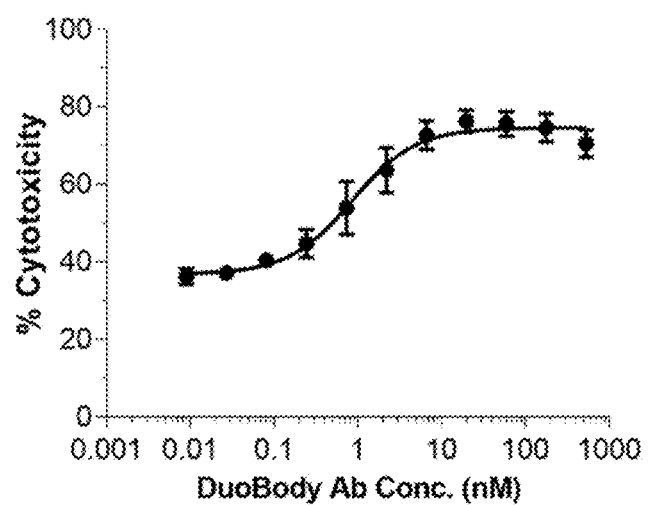
FIG. 2 shows a dose response curve of H929 cell cytotoxicity in whole blood after 48-hour incubation with Teclistamab.

D. Teclistamab-Mediated T Cell Dependent Cytotoxicity of Multiple Myeloma Cell Line in Healthy Whole Blood Assay For a more clinically relevant model, an in vitro whole blood model system was developed to evaluate the efficacy of teclistamab. BCMA positive MM H929 cells were spiked into the blood of 6 healthy donors, at an effector:target (E:T) ratio of 5:1, along with increasing concentrations of teclistamab for 48 hours to test target cell cytotoxicity, T cell activation, and cytokine release. Treatment with teclistamab (0.009 to 532 nM) resulted in dose-dependent H929 cytotoxicity as high as 88.5% as shown in FIG. 2. Cytotoxicity was measured by flow cytometry. The graph shown in FIG. 2 depicts the means of 6 individual donors ±SEM produced with GraphPad Prism software.

Individual cytotoxicity $EC_{50}$ ($EC_{20}$) values from the 6 donors ranged from 0.305-3.422 nM (0.052-1.917 nM) producing a mean of 1.262 nM (0.630 nM).

Figure 3:
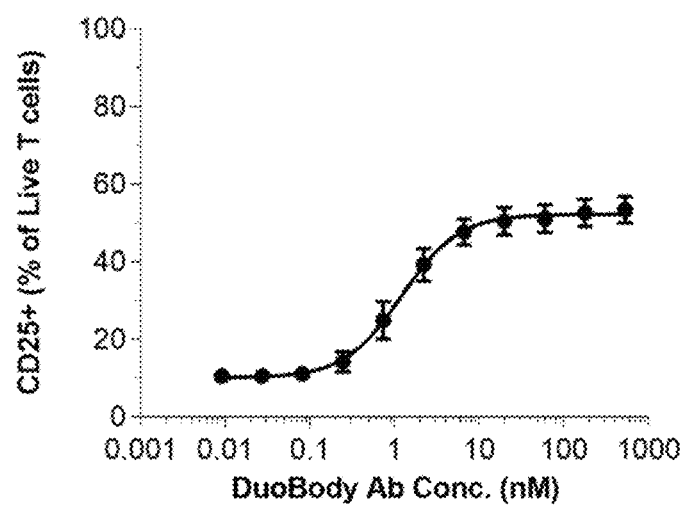
FIG. 3 shows a dose response curve of T cell activation with H929 cells in whole blood after 48-hour incubation with Teclistamab.

E. Teclistamab-Mediated T Cell Activation in the Presence of BCMA+ Cell Line in Whole Blood Assay Using the clinically relevant in vitro H929 whole blood model system described in Section D above, T cell activation was investigated. Activation was measured as the percentage of T cells (CD3+) that were also positive for activation marker CD25. Treatment with teclistamab (0.009 to 532 nM) resulted in dose-dependent T cell activation as high as 63.1% (FIG. 3). T cell activation was measured by flow cytometry. The graph shown in FIG. 3 depicts the means of 6 individual donors ±SEM produced with GraphPad Prism software.

Individual T cell activation $EC_{50}$ ($EC_{20}$) from the 6 donors ranged from 0.486-2.200 nM (0.191-0.940 nM) producing a mean of 1.406 nM (0.542 nM).

Figure 4:
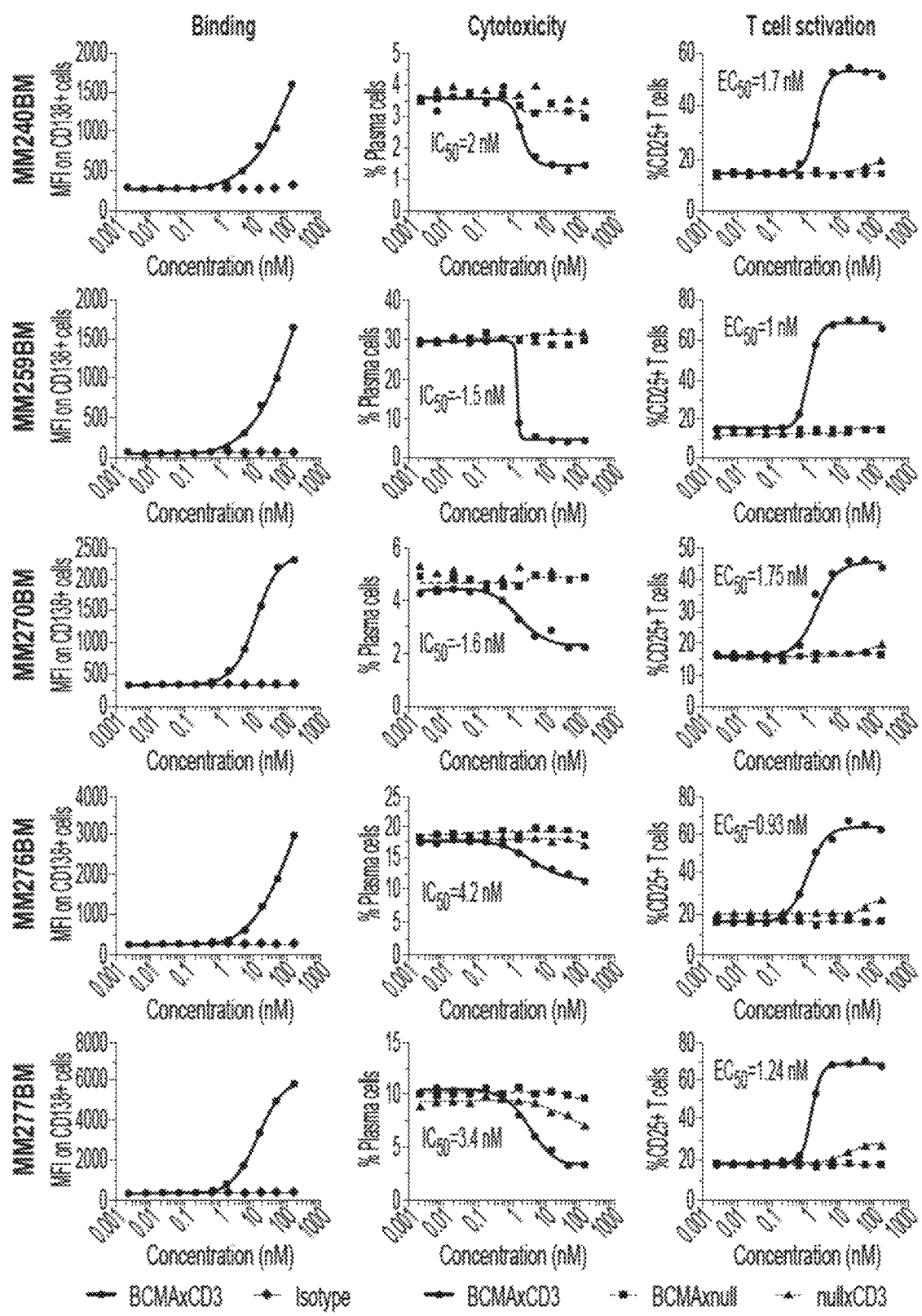
FIG. 4 shows cytotoxic potency of Teclistamab against human primary multiple myeloma plasma cells.

F. Teclistamab Binding, Cytotoxicity and T Cell Activation Assays Using Patient-Derived CD138+ Multiple Myeloma Bone Marrow Cells The ability of teclistamab to induce killing using primary multiple myeloma samples (n=5) in co-culture with T cells from healthy donors was assessed. Antibody binding and T cell activation potential were also measured. Teclistamab bound to and induced killing of all patient samples in a dose-dependent manner after 48 hours as measured by loss of CD138+ plasma cells (average $EC_{50}$ [$EC_{20}$] values were 2.53 [1.03] nM, FIG. 4). Frozen bone marrow-derived mononuclear cells from 5 different patients (multiple myeloma numbers on the Y axes) were used to assess teclistamab binding, compared with IgG4 isotype control (left panel), plasma cell cytotoxicity (middle) and T cell activation (right). Teclistamab binds to plasma cells in a dose dependent manner in all donor samples and the mean fluorescence intensities were recorded on the Y-axis. For the cytotoxicity assay, T cells from normal healthy donor (#M7077) were exogenously added to patient BMMNC samples and incubated with teclistamab, BCMA×null or CD3×null for 48 hours. A total of 100,000 T cells were added to each BM sample, leading to the following E:T ratios: A=14:1, B=1.7:1, C=13:1, D=2.9:1, E=5:1. Note the loss of live plasma cells (CD138+) and the concomitant up-regulation of CD25 on T cells in response to teclistamab treatment. The donor-specific IC50 values for cytotoxicity and EC50 values for T cell activation are indicated on the graphs of FIG. 4.

T cell activation data (average $EC_{50}$ [$EC_{20}$] values were 1.33 (0.70) nM) correlated with the results obtained from cell killing assays, as expected. Control null antibodies did not lead to significant killing or T cell activation except in 1 out of 5 patients who had minimal killing at concentrations >67 nM. These data show that teclistamab is able to induce cell killing in primary multiple myeloma bone marrow cells ex vivo.

G. Teclistamab Cytotoxicity Assays Using Autologous CD138+ Multiple Myeloma Bone Marrow Cells Multiple myeloma cell lysis by teclistamab was analyzed in an autologous setting with bone marrow mononuclear cell samples from multiple myeloma patients (Frerichs et al., *Clin Cancer Res*. published online ahead of print, 2020 Jan. 22). Serial dilutions of teclistamab (0.0064 to 4 µg/mL) were incubated with the samples for 48 hours. Lysis of $CD138^{high}$/$CD38^+$ multiple myeloma cells was assessed by flow cytometry.

Figure 5:
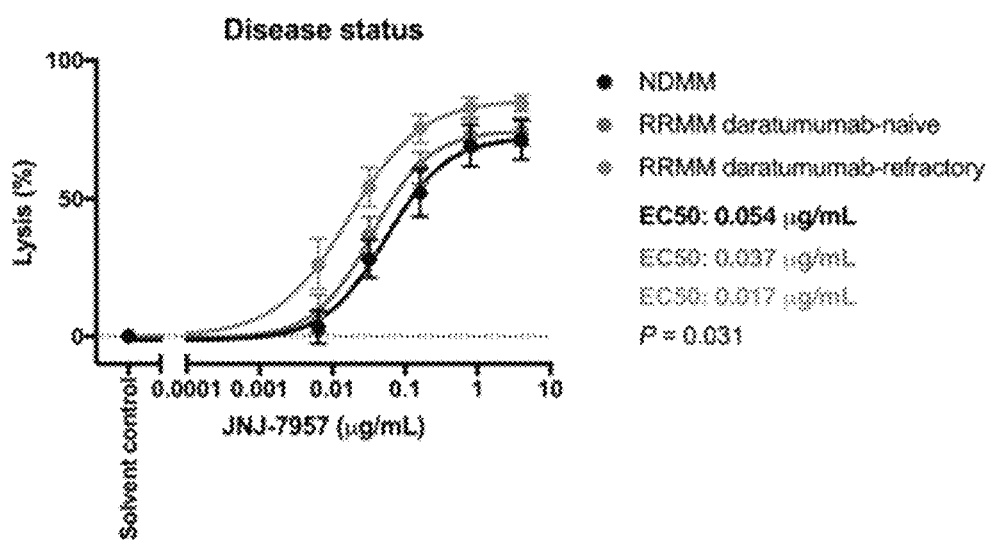
FIG. 5 shows autologous bone marrow CD138+ multiple myeloma lysis following incubation with Teclistamab.

Mean lysis of multiple myeloma cells was assessed in samples from patients with newly diagnosed multiple myeloma (n=11), daratumumab-naïve relapsed/refractory multiple myeloma (n=21), and daratumumab-refractory multiple myeloma (n=17; FIG. 5). Significantly higher lysis (p=0.031) was observed in daratumumab-refractory patients. Teclistamab-mediated multiple myeloma cell lysis was associated with activation (CD25) and degranulation (CD107a) of $CD4^+$ and $CD8^+$ T cells (Frerichs et al., 2020, id.).

Figure 6:
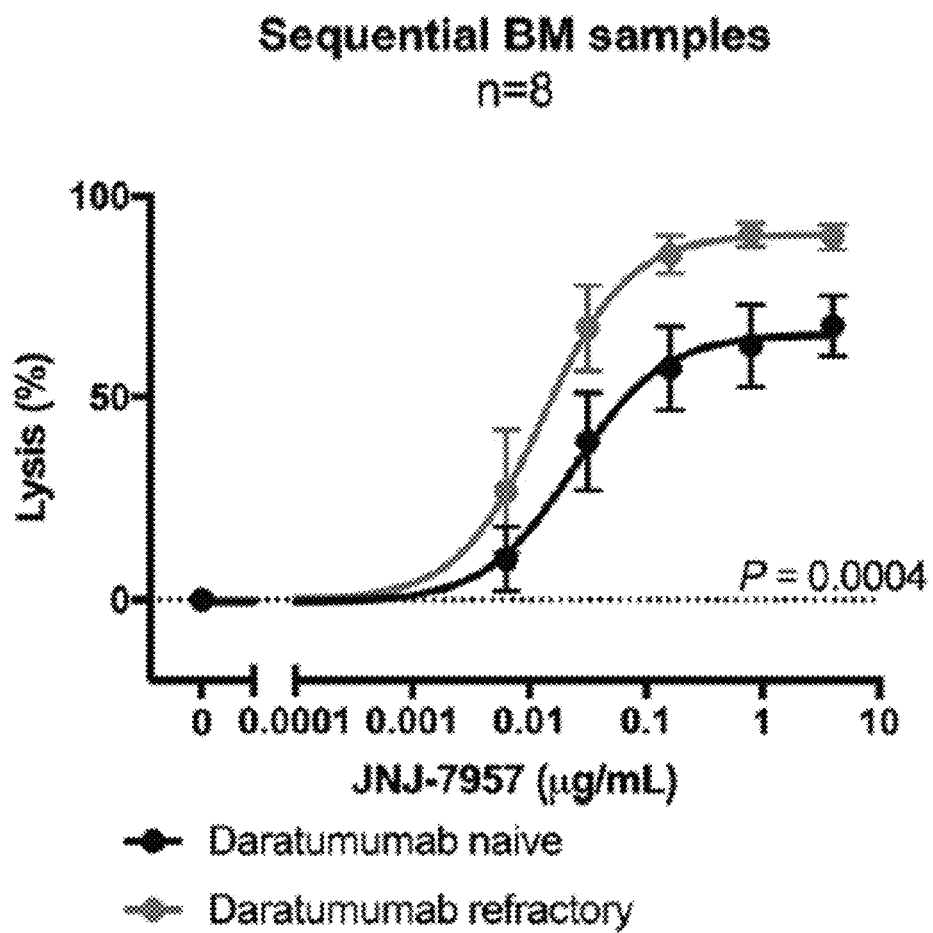
FIG. 6 shows in vivo Daratumumab pretreatment effects on in vitro autologous CD138+ relapsed/refractory multiple myeloma efficacy of Teclistamab.

Improvement in tumor reduction may be aided by the immune-stimulatory effects of daratumumab; therefore, the study also analyzed sequential bone marrow aspirates from multiple myeloma patients before and after daratumumab treatment (n=8). Significantly improved (p=0.0004) multiple myeloma cell lysis by teclistamab was observed in samples obtained after disease progression during daratumumab treatment compared with samples collected before daratumumab initiation (FIG. 6; Frerichs et al., 2020, id.).

H. Effect of Teclistamab in Murine T Cell Redirection Tumor Models

Efficacy of teclistamab was evaluated in 2 $BCMA^+$ human multiple myeloma models in peripheral blood mononuclear cell (PBMC)-humanized NOD/scidγc−/− (NSG) mice; either in a prophylactic model where treatment was initiated at the time of tumor cell implantation, or as an established model where treatment was initiated after palpable tumors were formed. In the prophylactic H929 model, teclistamab had antitumor efficacy with significant reduction of tumor formation and growth compared with phosphate-buffered saline (PBS)-treated control mice, at dose levels of either 0.5 or 1 µg/animal (0.025 or 0.05 mg/kg), whereas CD3×null or BCMA×null bispecific antibodies failed to suppress tumorigenesis in the model (FIG. 7).

Figure 7:
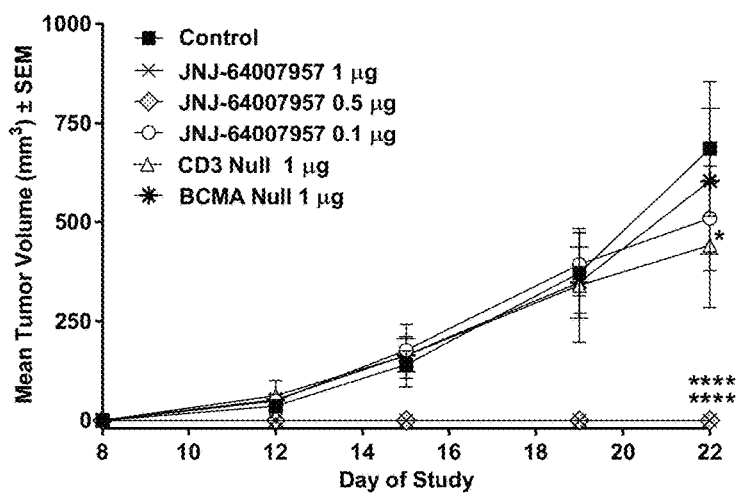
FIG. 7 shows Teclistamab-mediated cytotoxicity of BCMA+ multiple myeloma tumors in murine models.

FIG. 7 shows the H929 prophylactic model. NSG mice were IV engrafted with human PBMCs on Day −7. One week later on Day 1, mice were SC inoculated with H929 multiple myeloma cells, and then IV dosed with BCMA× CD3 bispecific teclistamab at 0.1, 0.5, or 1 µg/mouse (equivalent to 0.005, 0.025, or 0.05 mg/kg for a 20 g mouse) or corresponding control bispecific antibodies (BCMA×null or CD3×null). Subsequent dosing occurred on Days 4, 6, 8, and 11. Subcutaneous tumors were calipered twice weekly and the results presented as average tumor volume, expressed in mm3±SEM of each group. Only data through Day 22 is graphically represented, as this was the last day when the PBS-treated control tumor volumes remained below maximal tumor size limits.

Figure 8:
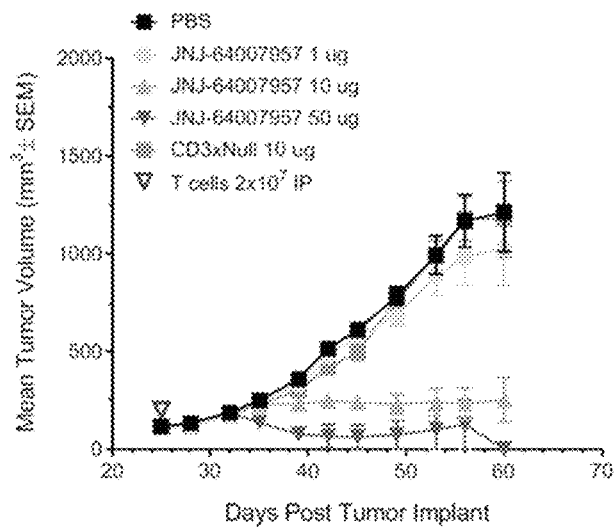
FIG. 8 shows Teclistamab-mediated cytotoxicity of BCMA+ multiple myeloma tumors in murine models.

In the established RPMI8226 model, 0.1 µg dose level/animal of teclistamab-inhibited tumor growth by 53% as compared with PBS-treated controls (p<0.05) on Day 28 (FIG. 8). The higher 1 µg dose level/animal of teclistamab showed limited efficacy and may represent a dose level where the bispecific antibody has oversaturated target binding, creating steric hindrance that blocks simultaneous dual-target binding. This effect has been observed previously at high dose levels with other CD3-redirection molecules (data not shown).

In FIG. 8, NSG mice were SC inoculated with RPMI8226 cells, and then IV engrafted with human PBMCs when tumors were established (mean tumor volume ~75 mm3). Mice were then IV dosed with control bispecific antibodies (BCMA×null or CD3×null on Days 1, 4, 6, 8, 11, 15, and 25 post PBMC implantation, or teclistamab at 0.1, or 1 µg/mouse (equivalent to 0.005 or 0.05 mg/kg for a 20 g mouse) on Days 8, 11, 13, 15, 18, and 25 post PBMC implantation. Only data through Day 28 is graphically represented, as this was the last day when at least n=7 mice remained in each group.

Example 2: Nonclinical Toxicology Studies of Teclistamab

A repeat-dose toxicity study was carried out in Cynomolgus monkeys. Cynomolgus monkeys were considered to be a pharmacologically relevant animal model to evaluate the potential toxicity of teclistamab. The anti-CD3 Fab bound to cynomolgus CD3 with similar affinity to human CD3. Cynomolgus BCMA has a >90% sequence similarity with human BCMA, and teclistamab demonstrated positive evidence of in vitro binding and functional activity (measured by cytotoxicity or T cell activation assays) in transfected cell-lines that over-expressed cynomolgus monkey BCMA (Table 5). Although the cynomolgus monkey was considered to be a pharmacologically relevant animal model for teclistamab, the binding affinity for cynomolgus monkey BCMA and the in vitro $EC_{50}$ for cytotoxicity and T-cell activation in cynomolgus monkey were 2- to 36-fold lower compared to the human values.

TABLE 5

Range of Binding Affinity and Activities of Antibodies to BCMA

| Antibody | Binding Affinity to BCMA (nM)[a] | | Cytotoxicity EC$_{50}$ (nM)[b] | | T-cell Activation EC$_{50}$ (nM)[b] | |
|---|---|---|---|---|---|---|
| | Human | Cyno | Human | Cyno | Human | Cyno |
| Teclistamab | (0.15-0.20) | (5.36-7.27) | 0.31-0.86 | 0.64-3.3 | 0.2-0.32 | 1.38-3.9 |

[a]Measured by SPR
[b]Human indicated the use of human BCMA and human T cells; cyno indicates the use of cynomolgus monkey BCMA and human T-cells. E:T ratio = 5:1;
Note:
Cytotoxicity and T-cell activation were measured at 48 h after treatment.
EC$_{50}$ = half-maximal effective concentration; SPR = surface plasma resonance The toxicological profile of teclistamab was evaluated in cynomolgus monkeys in a pivotal good laboratory practice (GLP), 5-week IV repeat dose toxicity study with an 8-week recovery period. In this study, teclistamab was administered by IV bolus injection to cynomolgus monkeys (5/sex/group) at dosages of 1, 10, and 30 mg/kg/week for 5 weeks. Teclistamab exposure (maximum concentration [$C_{max}$] and area under the curve [AUC]) increased in an approximately dose proportional manner (Table 6). Twenty-one out of 30 (70%) teclistamab-treated animals were anti-drug antibody (ADA)-positive in the 1 mg/kg (8 of 10), 10 mg/kg (8 of 10), and 30 mg/kg (5 of 10) dose groups. Of these 21 ADA-positive animals, 7 animals (2 animals in the 1 mg/kg/week group, 3 animals in the 10 mg/kg/week group, and 2 animals in the 30 mg/kg/week group) exhibited lower drug exposures compared with the ADA-negative animals in the same dose group at Day 22 and/or Day 29 (Table 6). The other 14 ADA-positive animals exhibited similar drug exposures when compared with those of the ADA-negative animals in the same dose group. Immunogenicity in monkeys toward human proteins is typically not expected to be predictive of human immunogenicity. When tested in vitro, the binding and cytotoxicity of teclistamab was lower in monkeys than in humans. Differences in BCMA expression in cynomolgus monkeys and multiple myeloma patients further limited the translation of the results. Typical hallmarks of activity associated with CD3 bispecific antibodies following administration to cynomolgus monkeys were not observed. Therefore, the results from the monkey studies should be interpreted with caution.

TABLE 6

Mean Serum Teclistamab Toxicokinetics Parameter Estimates

| Dose (mg/kg) | Following Dose on Day 1 | | Following Dose on Day 22 | | | ADA Positive (n+/total n) |
|---|---|---|---|---|---|---|
| | $C_{max}$[a] (μg/mL) | AUC$_{Day1-8}$[a] (μg · day/mL) | $C_{max}$[a] (μg/mL) | AUC$_{Day22-29}$[a] (μg · day/mL) | R[b] | |
| 1 | 26.77 | 63.36 | 38.58 | 128.93 | 2.04 | 8/10 |
| 10 | 300.30 | 719.86 | 417.75 | 1181.22 | 1.65 | 8/10 |
| 30 | 785.45 | 2032.35 | 1084.01 | 3549.19 | 1.75 | 5/10 |

[a]n = 5/sex/group.
[b]Mean of individual ratios are presented.
AUC$_{Day1-8}$ = area under the serum concentration versus time curve from Day 1 to Day 8; AUC$_{Day22-29}$ = area under the serum concentration versus time curve from Day 22 to Day 29; $C_{max}$ = maximum observed serum concentration; n = number; R = accumulation ratio calculated from AUC$_{Day22-29}$ and AUC$_{Day1-8}$ In this study, teclistamab was well tolerated with no effects on survival, clinical observations (including feeding behavior), body weight, ophthalmic examinations, physiologic parameters (blood pressure, heart rate, respiratory rate, and body temperature), clinical pathology (hematology, chemistry, and coagulation), immunology parameters (whole blood immunophenotyping and cytokines), gross necropsy findings, organ weights, or microscopic findings (including injection sites). Based on these findings, the no observed effect level (NOEL) for 5 weekly IV doses of teclistamab was 30 mg/kg in male and female monkeys.

The lack of pharmacodynamic (eg, cytokine release or transient lymphocyte decreases) or toxicological response to teclistamab was attributed to a combination of lower number of plasma cells (and consequently low expression of BCMA) in a healthy cynomolgus monkey and limited cross-reactivity of teclistamab to cynomolgus monkey relative to humans.

In addition to the 5-week GLP toxicity study with teclistamab described above, a 5-week non-GLP toxicity study in cynomolgus monkeys, a tissue cross-reactivity study, cytokine release assays, serum compatibility, and hemolytic potential assays were performed (data not shown).

Example 3: Phase 1/2 Study of Teclistamab Administered as Monotherapy for Relapsed or Refractory Multiple Myeloma A. Study Design A first-in-human Phase 1/2, open-label, multicenter study of teclistamab administered as monotherapy to adult subjects with multiple myeloma (MM) who were relapsed or refractory (RR) or intolerant to established therapies was carried out. The study encompasses 3 parts: Part 1 (dose escalation), Part 2 (dose expansion at proposed recommended phase 2 dose(s) (RP2D[s])), and Part 3 (Phase 2 dose expansion at RP2D in cohorts of subjects with relapsed or refractory multiple myeloma with unmet medical need).

Teclistamab is a humanized IgG4 proline, alanine, alanine (PAA)-based bispecific antibody directed against BCMA and the CD3 receptors, produced by cultivation of recombinant Chinese hamster ovary cells, followed by isolation, chromatographic purification, and formulation.

Teclistamab has a molecular mass of 146.261 kD for the GOF/GOF glycoform and isoelectric points ranging from pI 6.5 to 7.3. Its absorptivity constant at 280 nm was determined to be 1.58 (mg/mL)$^{-1}$ cm$^{-1}$.

The drug product is supplied in a vial for intravenous (IV) or subcutaneous (SC) administration following appropriate instructions for preparation that can require a diluting agent.

Teclistamab was administered intravenously (range, 0.3-19.2 μg/kg [biweekly]; 19.2-720 μg/kg [weekly]) or subcutaneously (80.0-3000 μg/kg weekly) in different cohorts; step-up dosing was employed for ≥38.4 μg/kg doses.

Figure 9:
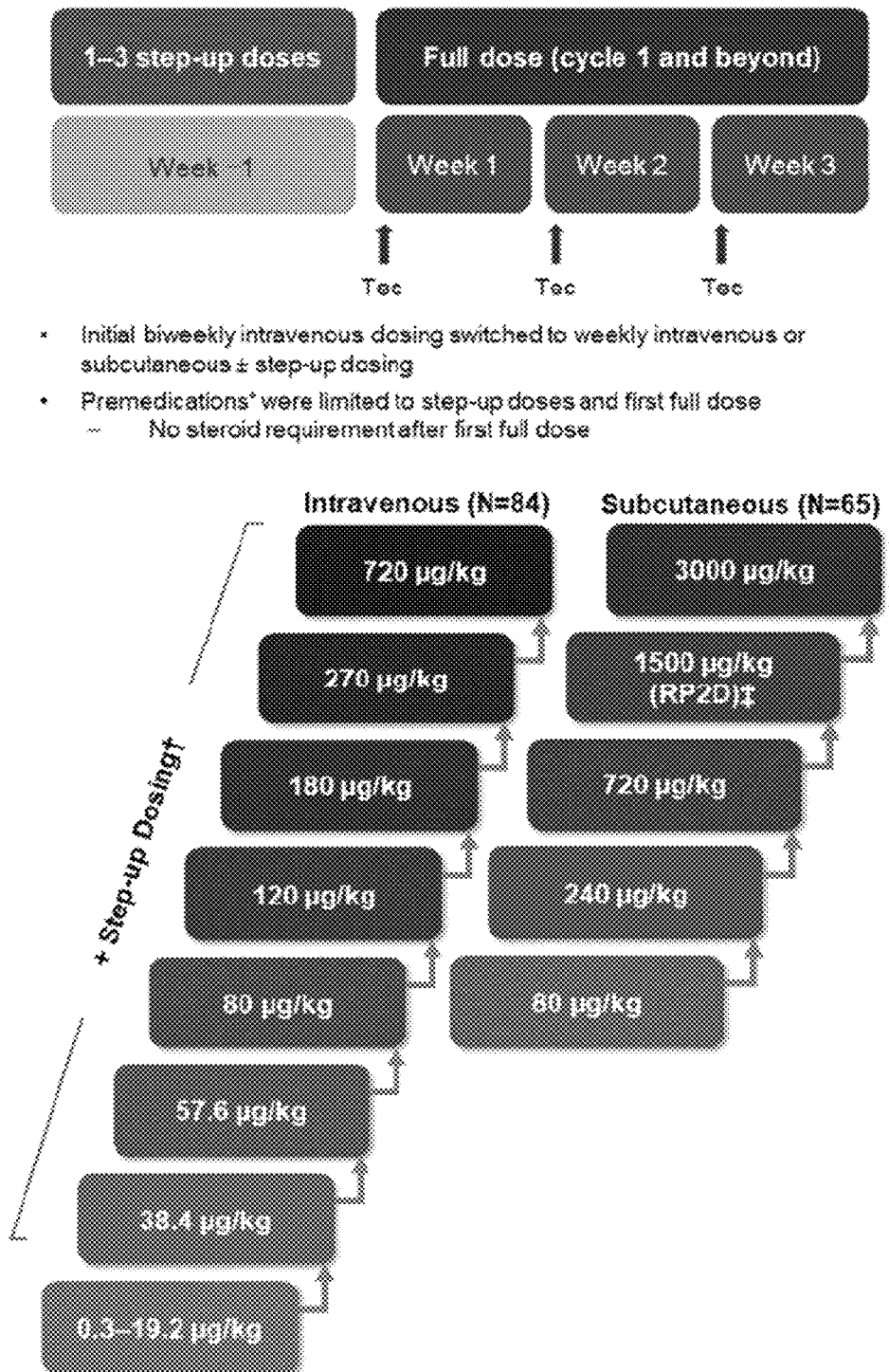
FIG. 9 shows a summary of the design of the study described in Example 3 herein.

A step-up dosing schedule (1-3 doses administered in separate cohorts for each dose level during the week prior to Cycle 1 Day 1) was implemented (FIG. 9). Subsequent intravenous and subcutaneous dose levels were selected using a modified continual reassessment method.

Patients were required to receive glucocorticoid, antihistamine, and antipyretic medications prior to step-up doses and the first full dose of teclistamab to mitigate cytokine release syndrome (CRS) and infusion-related reactions. Pretreatment administration of an H2-antagonist and an antiemetic was optional.

Patients continued to receive treatment until disease progression, unacceptable toxicity, withdrawal of consent, death, or end of study (defined as 2 years after the last patient's first dose).

Part 1 (Dose-Escalation)

The primary objective for part 1 was to identify a recommended phase 2 dose(s) by exploring multiple intravenous ±step-up doses, with a primary endpoint of the frequency and type of dose-limiting toxicities (DLTs).

Part 2 (Dose Expansion)

The primary objective for part 2 was to characterize teclistamab safety and tolerability at the potential RP2D. The primary endpoint of part 2 was the incidence and severity of AEs, serious AEs, and laboratory values. Other endpoints included overall response rate (ORR), duration of response, time to response, minimal residual disease (MRD) negativity rates, pharmacokinetic parameters, pharmacodynamic markers, and anti-teclistamab antibodies.

The following key cohorts were included in the study:

IV Cohort 16: 10 and 60 µg/kg step-up doses, followed by 270 µg/kg weekly treatment dose IV Cohort 17, 18: 10, 60, and 240 µg/kg step-up doses, followed by 720 µg/kg weekly treatment dose IV Cohort 19: 10, 60, and 300 µg/kg step-up doses, followed by 1500 µg/kg weekly treatment dose SC Cohort 3: 60 and 240 µg/kg step-up doses on Day −7 and Day −4, respectively, followed by 720 µg/kg weekly treatment dose starting on Cycle 1 Day 1

SC Cohort 4: 60 and 240 µg/kg step-up doses on Day −5 and Day −3/Day −2, respectively, followed by 720 µg/kg weekly treatment dose starting on Cycle 1 Day 1

SC Cohort 5, 6: 60 and 300 µg/kg step-up doses on Day −7 and Day −4, respectively, followed by 1500 µg/kg weekly treatment dose starting on Cycle 1 Day 1

SC Cohort 7: 60, 300, and 1500 µg/kg step-up doses on Day −7, Day −5 and Day −3, respectively, followed by 3000 µg/kg weekly treatment dose starting on Cycle 1 Day 1 Inclusion Criteria was as follows:

Each potential subject had to satisfy all of the following criteria to be enrolled in the study:

1. ≥18 years of age
2. Documented diagnosis of multiple myeloma according to IMWG diagnostic criteria.
3. Part 1 and Part 2: Measurable multiple myeloma that was relapsed or refractory to established therapies with known clinical benefit in relapsed/refractory multiple myeloma or be intolerant of those established multiple myeloma therapies, and a candidate for teclistamab treatment in the opinion of the treating physician. Prior lines of therapy must have included a proteasome inhibitor (PI) and an immunomodulatory drug (IMiD) in any order during the course of treatment. Subjects who could not tolerate a proteasome inhibitor or immunomodulatory drugs were allowed.

In Part 2 (dose expansion), in addition to the above criteria, multiple myeloma had to be measurable per current IMWG published guidelines by central lab assessment. If central lab assessment was not available, relevant local lab measurement had to exceed the minimum required level by at least 25%. A local bone marrow plasma cell percentage ≥30% could be used as measurable disease if no measurable disease was observed by serum or urine evaluation.

Part 3: Cohorts A, B and C: Multiple myeloma had to be measurable per current IMWG published guidelines by central lab assessment:

Serum monoclonal paraprotein (M-protein) level ≥1.0 g/dL or urine M-protein level ≥200 mg/24 hours; or Light chain multiple myeloma without measurable disease in the serum or the urine: Serum immunoglobulin free light chain (FLC) ≥10 mg/dL and abnormal serum immunoglobulin kappa lambda FLC ratio.

If central lab assessments were not available, relevant local lab measurements had to exceed the minimum required level by at least 25%.

Prior treatment (Part 3):

Cohort A: Subjects must have 1) received at least 3 prior treatment lines or be double refractory to a PI and IMiD and 2) previously received a PI, an IMiD, and an anti-CD38 antibody (refractory multiple myeloma as defined by IMWG consensus criteria). Note: Induction with or without hematopoietic stem cell transplant and with or without maintenance therapy was considered a single line of therapy.

Undergone at least 1 complete cycle of treatment for each line of therapy, unless progressive disease was the best response to the line of therapy.

Subject must have had documented evidence of progressive disease based on investigator's determination of response by the IMWG criteria on or within 12 months of their last line of therapy.

Cohort B: received at least 4 prior multiple myeloma treatment lines of therapies and whose disease was penta-refractory to at least 2 PIs, at least 2 IMiDs, and an anti-CD38 monoclonal antibody (refractory multiple myeloma as defined by IMWG consensus criteria). Note: Induction with or without hematopoietic stem cell transplant and with or without maintenance therapy was considered a single line of therapy.

Undergone at least 1 complete cycle of treatment for each line of therapy, unless progressive disease was the best response to the line of therapy.

Subject must have had documented evidence of progressive disease based on investigator's determination of response by the IMWG criteria on or within 12 months of their last line of therapy.

Cohort C: refractory to or progressed after treatment with CAR-T therapy directed against BCMA or an ADC directed against BCMA.

Subject must have documented evidence of progressive disease based on investigator's determination of response by the IMWG criteria within 12 months of the BCMA directed-therapy.

4. Eastern Cooperative Oncology Group (ECOG) Performance Status score of 0 or 1.

5. Pretreatment clinical laboratory values meeting the following criteria during the Screening Phase:

| Hematology | |
|---|---|
| Hemoglobin | ≥8 g/dL (≥5 mmol/L) (without prior red blood cell [RBC] transfusion within 7 days before the laboratory test; recombinant human erythropoietin use was permitted) |
| Platelets | ≥75 × 10$^9$/L for subjects in whom <50% of bone marrow nucleated cells were plasma cells; otherwise platelet count ≥50 × 10$^9$/L (without transfusion support in the 7 days prior to the laboratory test) |
| Absolute Neutrophil Count (ANC) | ≥1.0 × 10$^9$/L (prior growth factor support was permitted but must have been without support in the 7 days prior to the laboratory test) |
| Chemistry | |
| AST and ALT | ≤3.0 × upper limit of normal (ULN) |
| Creatinine or | Serum creatinine: ≤1.5 mg/dL or |
| Creatinine clearance | Creatinine clearance: ≥40 mL/min/1.73 m$^2$ based upon Modified Diet in Renal Disease formula calculation |
| Total bilirubin | ≤2.0× ULN; except in subjects with congenital bilirubinemia, such as Gilbert syndrome (in which case direct bilirubin ≤1.5 × ULN was required) |
| Corrected serum calcium | ≤14 mg/dL (≤3.5 mmol/L) or free ionized calcium <6.5 mg/dL (<1.6 mmol/L) |

6. Women of childbearing potential must have had a negative pregnancy test at screening and prior to the first dose of study drug using a highly sensitive pregnancy test either serum (β human chorionic gonadotropin [β-hCG]) or urine.
7. Women of childbearing potential and fertile men who were sexually active must have agreed to use a highly effective method of contraception (<1%/year failure rate) from the time of signing the ICF,) during the study and for 90 days after the last dose of study drug. Contraception must have been consistent with local regulations regarding the use of birth control methods for subjects participating in clinical trials. When a woman was of childbearing potential, subject must have agreed to practice a highly effective method of contraception (failure rate of <1% per year when used consistently and correctly.
   In addition to the highly effective method of contraception, a man who was sexually active with a woman of childbearing potential must have agreed to use a barrier method of contraception, and must have used a condom
   Women and men must have agreed not to donate eggs (ova, oocytes) or sperm, respectively, during the study and for 90 days after the last dose of study drug. Note: If the childbearing potential changed after start of the study or the risk of pregnancy changed, a woman must have begun a highly effective method of contraception, as described throughout the inclusion criteria. If reproductive status was questionable, additional evaluation was considered. It should be noted that interaction between hormonal contraception and teclistamab have not been studied. Therefore, it is unknown whether teclistamab may reduce the efficacy of the contraceptive method.
8. Subject must have signed an informed consent form (ICF) indicating that he or she understood the purpose of and procedures required for the study and was willing to participate in the study. Consent was to be obtained prior to the initiation of any study-related tests or procedures that were not part of standard-of-care for the subject's disease.
9. Willing and able to adhere to the prohibitions and restrictions specified in this protocol.

Exclusion Criteria was as follows:
Any potential subject who met any of the following criteria was excluded from participating in the study:
1. Prior treatment with any BCMA-targeted therapy, with the exception of Cohort C.
2. Prior antitumor therapy as follows, before the first dose of study drug:
   Targeted therapy, epigenetic therapy, or treatment with an investigational drug or used an invasive investigational medical device within 21 days or at least 5 half-lives, whichever is less.
   Monoclonal antibody treatment for multiple myeloma within 21 days.
   Cytotoxic therapy within 21 days.
   Proteasome inhibitor therapy within 14 days.
   Immunomodulatory agent therapy within 7 days.
   Radiotherapy within 21 days. However, if the radiation portal covered ≤5% of the bone marrow reserve, the subject was eligible irrespective of the end date of radiotherapy.
3. Toxicities from previous anticancer therapies that had not resolved to baseline levels or to Grade 1 or less except for alopecia or peripheral neuropathy.
4. Received a cumulative dose of corticosteroids equivalent to ≥140 mg of prednisone within the 14-day period before the first dose of study drug (did not include pretreatment medication).
5. Stem cell transplantation:
   An allogeneic stem cell transplant within 6 months. Subjects who received an allogeneic transplant must have been off all immunosuppressive medications for 6 weeks without signs of graft-versus-host disease.
   Received an autologous stem cell transplant ≤12 weeks before the first dose of study drug.
6. Known active CNS involvement or exhibited clinical signs of meningeal involvement of multiple myeloma.
7. Plasma cell leukemia (>2.0×10$^9$/L plasma cells by standard differential), Waldenstrom's macroglobulinemia, POEMS syndrome (polyneuropathy, organomegaly, endocrinopathy, monoclonal protein, and skin changes), or primary amyloid light-chain amyloidosis.

8. Known to be seropositive for human immunodeficiency virus or acquired immune deficiency syndrome.
9. Hepatitis B infection or at risk for hepatitis B virus reactivation as defined according to the American Society of Clinical Oncology guidelines. Eligibility was determined by the investigator. In the event the infection status was unclear, quantitative levels were necessary to determine the infection status. Active Hepatitis C infection as measured by positive hepatitis C virus (HCV)-RNA testing. Subjects with a history of HCV antibody positivity had to undergo HCV-RNA testing.
10. Pulmonary compromise requiring supplemental oxygen use to maintain adequate oxygenation.
11. Known allergies, hypersensitivity, or intolerance to teclistamab or its excipients.
12. Any serious underlying medical condition, such as:
    Evidence of serious active viral, bacterial, or uncontrolled systemic fungal infection
    Active autoimmune disease or a documented history of autoimmune disease
    Psychiatric conditions (e.g., alcohol or drug abuse), dementia, or altered mental status
    Any other issue that would impair the ability of the subject to receive or tolerate the planned treatment at the investigational site, to understand informed consent or any condition for which, in the opinion of the investigator, participation would not be in the best interest of the subject (e.g., compromise the well-being) or that could prevent, limit, or confound the protocol-specified assessments.
13. Pregnant or breast-feeding, or planning to become pregnant while enrolled in the study or within 90 days after receiving the last dose of study drug.
14. Planned to father a child while enrolled in the study or within 90 days after receiving the last dose of study drug.
15. Major surgery within 2 weeks of the first dose, or would not have fully recovered from surgery, or had surgery planned during the time the subject was expected to participate in the study or within 2 weeks after the last dose of study drug administration (note: subjects with planned surgical procedures to be conducted under local anesthesia could participate).
16. Stroke or seizure within 6 months of signing informed consent form.
17. The following cardiac conditions:
    New York Heart Association (NYHA) stage III or IV congestive heart failure
    Myocardial infarction or coronary artery bypass graft (CABG)≤6 months prior to enrollment
    History of clinically significant ventricular arrhythmia or unexplained syncope, not believed to be vasovagal in nature or due to dehydration
    History of severe non-ischemic cardiomyopathy
    Impaired cardiac function (LVEF <45%) as assessed by echocardiogram or multiple-gated acquisition (MUGA) scan (performed ≤8 weeks prior to enrollment)
18. Diagnosed or treated for invasive malignancy other than multiple myeloma, except:
    Malignancy treated with curative intent and with no known active disease present for >2 years before enrollment; or
    Adequately treated non-melanoma skin cancer without evidence of disease
    B. Methods
    Adverse events (AEs) were graded per National Cancer Institute Common Terminology Criteria for Adverse Events v4.03m, and cytokine release syndrome (CRS) was graded by Lee et al., *Blood* 2014; 124:188. Blood samples were collected for clinical laboratory tests prior to each dose of teclistamab and at additional timepoints during the first treatment cycle. Response was assessed by the investigator using International Myeloma Working Group criteria on Day 1 of each cycle until disease progression, death, start of a new anticancer treatment, withdrawal of consent for study participation, or end of the study, whichever occurred first, and minimal residual disease (MRD) in bone marrow was assessed by next generastion sequencing (NGS).

Blood samples and bone marrow aspirate were collected for pharmacokinetic, pharmacodynamic, and immunogenicity analyses at prespecified intervals. Serum samples were analyzed for teclistamab concentrations, cytokine profiles, and antibodies to teclistamab using validated assays. Immune cell populations were analyzed by flow cytometry.

Treatment with teclistamab in the study started with intravenous (IV) dosing at the minimum anticipated biologic effect level-based dose of 0.3 µg/kg every 2 weeks (Q2W) on Days 1 and 15 of 28-day cycles; however, dosing frequency was switched to weekly dosing on Days 1, 8, and 15 of 21-day cycles after review of initial pharmacokinetics (PK) data (see below). After review of safety and efficacy data and with the expectation cytokine release syndrome (CRS) might be mitigated with subcutaneous (SC) administration, SC dosing was also evaluated.

Statistical Analysis

Teclistamab dose escalation and RP2D identification were guided using a modified continual reassessment method, which was based on the probability of DLTs by a two-parameter Bayesian logistic regression model (Neuenschwander B, Branson M, Gsponer T. Critical aspects of the Bayesian approach to phase I cancer trials. Stat Med 2008; 27:2420-39) and escalation with overdose control principle (Babb J, Rogatko A, Zacks S. Cancer phase I clinical trials: efficient dose escalation with overdose control. Stat Med 1998; 17:1103-20).

Safety was assessed in all patients treated with ≥1 dose of teclistamab. Efficacy was analyzed in response-evaluable patients, which included all those who received ≥1 dose of teclistamab and had ≥1 post-baseline response evaluation. Pharmacokinetics, pharmacodynamics, and immunogenicity were analyzed in patients who received ≥1 dose of teclistamab and had ≥1 evaluable measurement of teclistamab plasma concentration, ≥1 biomarker measurement, and ≥1 post-dose immunogenicity sample, respectively.

Minimum Anticipated Biologic Effect Level (MABEL)-Based Starting Dose

Determination for the MABEL-based starting dose for teclistamab was guided by nonclinical data derived from in vitro studies evaluating both efficacy (T-cell activation and T-cell redirected killing of BCMA-positive multiple myeloma cells) and safety (cytokine release) endpoints. Two in vitro assay systems (whole blood and purified T cells) were used for independent validation leading to an estimated MABEL of 0.04 nM-based starting dose of 0.3 µg/kg teclistamab administered as an approximately 4-hour infusion once every 2 weeks. This was based on a conservative approach using the lowest mean EC20 from the most sensitive assay among T-cell activation, cytotoxicity, and cytokine release.

Modified Continual Reassessment Method for Teclistamab Administration and Dose Escalation Teclistamab was administered under the supervision of site staff. The first intravenous dose was administered over ≥2 hours, and patients were clinically monitored every 15-20 minutes during the infusion, at the end of infusion, and at 0.5, 1, 2, and 3 hours post-infusion. For all subsequent infusions, patients were monitored immediately before infusion, every 30 minutes during infusion, at the end of infusion, and as clinically indicated. In the absence of any grade ≥2 CRS or infusion-related reactions during cycle 1, subsequent doses could be administered over a duration of approximately 1 hour, with sponsor approval. Once a dose level was considered safe by the safety evaluation team (SET), the intravenous administration at that dose could be administered over 1 hour.

For intravenous administration, the modified continual reassessment method was implemented in two titration phases (accelerated and standard); for subcutaneous administration, only the standard titration phase was used. In the accelerated titration phase, dose escalation began with one to three patients receiving treatment in a staggered manner to allow ≥72 hours between the first dose of consecutive patients (if ≥1 patient); ≥1 patient was required to be evaluated for DLTs before the dose could be considered safe and patients were enrolled in the next dose level cohort. The dose for the next dose level cohort was determined based on all available data, including recommended dose by Bayesian logistic regression model and escalation with overdose control principle at the time of review; the next dose was not permitted to be more than twice the previous dose. The accelerated titration was to be terminated and standard titration started if a DLT or a grade ≥2 toxicity occurred.

In the standard titration phase, ≥3 patients were enrolled in each dose level cohort using a staggered approach similar to that in the accelerated titration phase; ≥3 patients were required to complete one treatment cycle before the dose could be considered safe and patients were enrolled in the next dose level cohort. If only two patients were available for assessment (i.e., if other patients discontinued treatment) and neither patient experienced a grade ≥2 toxicity, two patients were considered sufficient for decision making. Patients who did not complete DLT evaluation for reasons other than DLT could be replaced. If one patient experienced a DLT during cycle 1, the SET could either allow enrollment of ≤6 additional patients or reassess all available data and the updated probability of DLT to determine the next dose level cohort according to Bayesian logistic regression model and escalation with overdose control principle. If two patients experienced a DLT, further enrollment in that dose level cohort was to stop and the SET was to reassess all available data to determine whether additional patients should be enrolled at the current or a lower dose level that would meet the escalation with overdose control principle. Up to 12 patients could be enrolled in a cohort at or below a dose level determined by the SET to be safe. If no DLTs were observed, the dose escalation continued to next dose level with the designated step-up dose(s). To be considered a step-up dose, it must have been tested in ≥3 patients who completed DLT evaluation at that dose. The step-up dose(s) or schedule could be eliminated or adjusted by the SET to obtain the desired T cell adaptation effect to reduce cytokine levels, and thus decrease symptomatic CRS in a majority of treated patients. The step-up dose could also be adjusted to mitigate drug-related toxicities other than CRS.

Dose-Limiting Toxicity Criteria

Dose-limiting nonhematologic toxicities were grade ≥3 general nonhematologic toxicity (excluding alopecia; grade 3 neurotoxicity that fails to resolve to baseline or grade ≤1 in <72 hours; grade 3 asthenia, fever, or constipation; grade 3 nausea, vomiting, or diarrhea [unless it requires tube feeding, total parenteral nutrition, or hospitalization]; infection, bleeding, or other expected direct complications of cytopenias due to active disease; and first occurrence of limited grade 3 CRS [i.e., recovers to baseline or grade ≤1 in <72 hours]), grade 3 general chemistry abnormality (if persisting for >7 days or associated with clinical complications despite best supportive care [including electrolyte and hormone supplementation where clinically applicable according to institutional standards]), grade 4 general chemistry abnormality (unless resolved within 5 days to grade ≤1 or baseline and related to CRS or infusion-related event), grade 5 general chemistry abnormalities, grade 3 elevated aspartate aminotransferase (AST) or alanine aminotransferase (ALT) that has not returned to grade ≤1 or baseline within 7 days or meeting Hy's law criteria (i.e., AST or ALT ≥3×upper limit of normal [ULN], total bilirubin ≥2×ULN, and alkaline phosphatase ≤2×ULN; with no alternative etiology), or grade 3 elevated lipase and/or amylase associated with clinical or radiological evidence of pancreatitis.

Dose-limiting hematologic toxicities were grade 4 neutropenia for >7 days, grade 3 febrile neutropenia not recovering to grade ≤1 within 7 days, grade 4 febrile neutropenia, grade 3 thrombocytopenia with clinically significant bleeding, grade 4 thrombocytopenia, or grade 5 neutropenia, febrile neutropenia, or thrombocytopenia. For hematologic toxicities, laboratory monitoring including complete and differential blood counts were performed frequently to document their start and resolution.

Dose Modifications

In the case of a DLT, treatment was required to be withheld and supportive therapy administered. For other grade ≥3 clinically significant toxicities, treatment could be withheld as clinically indicated and supportive therapy administered; treatment could be restarted if grade ≥3 toxicity resolved to grade ≤1 or baseline If treatment was resumed, a lower dose could be administered if deemed clinically appropriate, with the sponsor's approval. The first dose reduction was one dose level below the current dose or lower, and the second dose reduction was two dose levels below the current dose or lower, with lower dose levels defined as those assessed during the dose escalation portion (part 1) and declared safe. In the case of any-grade CRS, treatment was required to be withheld until its resolution.

Teclistamab was to be discontinued for grade 4 infusion-related reaction; grade ≥3 injection-site reaction; grade 3 or 4 CRS, except for the first occurrence of limited grade 3 CRS (i.e., recovery to grade ≤1 or baseline in ≤48 hours); recurrent grade 3 or any grade 4 neurotoxicity; grade 4 nonhematologic toxicity meeting DLT criteria, except for transient grade 4 laboratory abnormalities related to tumor lysis syndrome, grade 4 lipase or amylase elevation without clinical symptoms or radiological findings of pancreatitis, symptoms of grade ½ CRS or first occurrence of limited grade 3 CRS (i.e., recovery to grade ≤1 or baseline in <5 days), or related to first occurrent of grade 3 CRS; grade 4 hematologic toxicity meeting DLT criteria; pregnancy; concurrent (non-protocol) systemic anticancer treatment; intercurrent illness that prevents further administration of treatment; refusal of further treatment; noncompliance with teclistamab or procedure requirements; confirmed disease progression per IMWG criteria, unless judged by investigator to be in patient's best interest to continue treatment and after sponsor's approval; or any safety or tolerability reason at the investigator's discretion.

In the overall population and recommended phase 2 dose cohort, respectively, adverse events led to cycle delays in 51 (32.5%) and 16 (40.0%) patients, to dose delays in 20

(12.7%) and four (10.0%) patients, and to dose reductions in five (3.2%) and zero patients.

Minimal Residual Disease (MRD)

MRD was assessed to determine the ability of monotherapy Teclistamab to drive deep quantitative responses in this challenging patient population.

Evaluation of MRD was performed by ClonoSEQ™ assay (Adaptive Biotechnologies, Seattle, Wash., USA) using bone marrow aspirates (BMA) from all subjects with suspected complete response (CR). Additional MRD evaluations were performed post suspected CR for subjects who who remained on study, if feasible. The ClonoSEQ™ MRD assay utilizes next generation sequencing (NGS) to determine the frequency of myeloma clonotypes identified at baseline, using a set of multiplexed, locus-specific primer sets for the immunoglobulin heavy-chains (IgH, IgK, IgL).

The MRD status was determined at sensitivity of $10^{-4}$ (0.01%, 1 cancer cell per 10,000 white blood cells, [WBC]), $10^{-5}$ (0.001%, 1 cancer cell per 100,000 WBC), and $10^{-6}$ (0.0001%, 1 cancer cell per 1,000,000 WBC). Patients were deemed evaluable if they had a bone marrow screening (treatment naïve) sample that identified a dominant myeloma clonotype to track and a suspected CR sample to trace said clone. The threshold for sensitivity to define MRD negativity can depend on the assay being used and the number of cells or cellular equivalents evaluated. The ClonoSEQ™ assay was utilized which can reach a limit of sensitivity of 10'. However, the myeloma community, including the International Myeloma Working Group (IMWG), recently released guidelines for MRD evaluation and recommended $10^{-5}$ as the threshold for MRD evaluation regardless of assay being used. Therefore, MRD negativity was evaluated at the $10^{-5}$ IMWG proposed threshold and at the $10^{-6}$ sensitivity threshold of the ClonoSEQ™ assay. At suspected CR, 6/7 evaluable patients were deemed negative at both the $10^{-5}$ IMWG proposed threshold as well as at the highest sensitivity threshold of $10^{-6}$. Of these patients, 5 received IV dosing and 4/5 patients were MRD negative, while the remaining 2 patients received SC dosing and both were confirmed as MRD negative.

C. Study Population and Duration of Treatment, First Data Cutoff

A first data cutoff took place in March 2020.

A total of 74 subjects were treated with IV teclistamab in at doses of up to 19.2 µg/kg every two weeks (Q2W) (Cohorts 1-7) and up to 720 µg/kg weekly (Cohorts 8-17). A total of 24 subjects were treated with SC teclistamab at doses up to 720 µg/kg weekly (Cohorts 1-4). A variety of step-up dose strategies were employed for each route of administration. Key eligibility requirements included:

Measurable MM

RR or intolerant to established MM therapies

Hb ≥8 g/dL, platelets$^a$≥75×10$^9$/L, ANC ≥1.0× 10$^9$/L ($^a$≥50×10$^9$/L for patients with ≥50% bone marrow plasma cells)

IV Administration

Among subjects treated IV, the median age was 63.0 years (24 to 82 years). The median number of prior therapeutic regimens was 6 (range 2 to 14). Per protocol, subjects in Part 1 or Part 2 must have had prior therapy with a proteasome inhibitor (PI) and an immunomodulatory agent (IMiD) (or known intolerance). 87.8% of these subjects were refractory to PI+IMiD, 82.4% of subjects were triple refractory (PI/IMiD/anti-CD38), and 40.5% of subjects were penta-refractory (2 PI, 2 IMiD, anti-CD38).

The median duration of IV teclistamab treatment for all subjects was 2.1 months (range 0.03 to 17.2 months). The median duration of treatment for confirmed responders (n=19) was 6.4 months (range 2.1 to 17.2 months).

In IV Cohort 16 (270 µg/kg weekly treatment dose; n=11), the median duration of treatment was 2.8 months (range 0.03 to 6.3 months) at the time of the data cutoff, with a median of 4.5 months for confirmed responders (n=6) in this cohort.

In IV Cohort 17 (720 µg/kg weekly treatment dose; n=6), the median duration of treatment for all subjects was 0.4 months (range 0.3 to 1 month) at the time of the data cutoff.

SC Administration

Among subjects treated SC, the median age was 67.0 years (41 to 76 years). The median number of prior therapeutic regimens was 6.0 (range 3 to 14). 83.3% of subjects were refractory to PI+IMiD, 70.8% of subjects were triple refractory (PI/IMiD/anti-CD38), and 37.5% of subjects were penta-refractory (2 PI, 2 IMiD, anti-CD38).

The median duration of SC teclistamab treatment for all subjects was 2.1 months (range 0.7 to 6.7 months). The median duration of treatment for confirmed responders (n=10) was 4.4 months (range 2.1 to 6.2 months).

In SC Cohort 3 and SC Cohort 4 (720 µg/kg weekly treatment dose; n=11), the median duration of treatment was 1.9 months (range 0.7 to 3.7 months) at the time of the data cutoff, with a median of 2.8 months for responders (n=5) in these cohorts.

D. Safety, First Data Cutoff

In the analyses and text presented herein, Day 1 of the study refers to the first day that study drug (step-up dose or full treatment dose [Cohorts 1-9]) was administered.

1. Dose-Limiting Toxicities

Two dose-limiting toxicities (DLTs) were observed in subjects treated with IV teclistamab. No DLTs have been reported in subjects treated with SC teclistamab.

2. Treatment-Emergent Adverse Events (TEAEs)

An AE was considered treatment emergent if it occurred at or after the initial administration of study drug through the day of last dose plus 100 days (Part 1 and Part 2) or plus 30 days (Part 3) or the day prior to start of subsequent anticancer therapy, whichever was earlier. Any AE that was considered very likely, probably, or possibly related to study drug by the investigator was also considered treatment-emergent, regardless of the start date of the event.

IV Administration

Among subjects treated with IV teclistamab, 72 (97.3%) had ≥1 TEAE. Twenty-six subjects (35.1%) had any TEAE with maximum severity of Grade 3; 33 subjects (44.6%) had any TEAE with maximum severity of Grade 4. One subject experienced a Grade 5 TEAE and 1 additional subject experienced a Grade 5 AE that was not considered treatment emergent. Thirty-six subjects (48.6%) experienced a total of 87 serious TEAEs.

Forty-three subjects (58.1%) experienced ≥1 infection-related TEAE. A TEAE was identified as infection-related by the investigator in the electronic case report form (eCRF). Five subjects (6.8%) experienced ≥1 infusion-related TEAE. Neurotoxicity events related to teclistamab are presented below. CRS was reported in 40 subjects (54.1%). Of these subjects, 27 (36.5%) had maximum Grade 1 CRS and 13 (17.6%) had maximum Grade 2 CRS. Grade 3 or higher CRS was not reported.

The most frequently reported TEAEs (≥20% of subjects) were anemia (44 subjects [59.5%]), CRS (39 subjects [52.7%; see note below), neutropenia (37 subjects [50.0%]), thrombocytopenia (31 subjects [41.9%]), leukopenia (22 subjects [29.7%], pyrexia (22 subjects [29.7%]), diarrhea (18 subjects [24.3%]), cough (18 subjects [24.3%]), upper respiratory tract infection (16 subjects [21.6%]), back pain (15 subjects [20.3%]), and headache (15 subjects [20.3]).

SC Administration

Among subjects treated with SC teclistamab, 24 (100.0%) had ≥1 TEAE. Ten subjects (41.7%) had any TEAE with maximum severity of Grade 3; 6 subjects (25.0%) had any TEAE with maximum severity of Grade 4. No subject had Grade 5 TEAEs or AEs. Six subjects (25.0%) experienced a total of 9 serious TEAEs.

Eleven subjects (45.8%) experienced ≥1 infection-related TEAE. Four subjects (16.7%) experienced ≥1 injection-related TEAE. No neurotoxicity events related to SC teclistamab were reported. CRS was reported in 11 subjects (45.8%). Of these subjects, 10 (41.7%) had maximum Grade 1 CRS and 1 (4.2%) had maximum Grade 2 CRS.

The most frequently reported TEAEs (≥20% of subjects) were anemia (12 subjects [50.0%]), CRS (11 subjects [45.8%]), neutropenia (11 subjects [45.8%]), thrombocytopenia (7 subjects [29.2%]), pyrexia (6 subjects [25.0%]), cough (6 subjects [25.0%]), upper respiratory tract infection (5 subjects [20.8%]), and nausea (5 subjects [20.8%].

3. Grade 3 and Grade 4 TEAEs

IV Administration

Grade 3 or 4 TEAEs were experienced by 60 subjects (81.1%) treated with IV teclistamab. The most frequently reported events (≥5% of subjects) included neutropenia (31 subjects [41.9%]), anemia (27 subjects [36.5%]), thrombocytopenia (18 subjects [24.3%]), leukopenia (11 subjects [14.9%]), lymphopenia (11 subjects [14.9%]), hyperphosphatemia (6 subjects [8.1%]), pneumonia (5 subjects [6.8%]), sepsis (5 subjects [6.8%]), hypercalcemia (4 subjects [5.4%]), hypertension (4 subjects [5.4%]), and acute kidney injury (4 subjects [5.4%]).

SC Administration

Grade 3 or 4 TEAEs were experienced by 16 subjects (66.7%) treated with SC teclistamab. The most frequently reported events (≥5% of subjects) included neutropenia (8 subjects [33.3%]), anemia (6 subjects [25.0%]), thrombocytopenia (5 subjects [20.8%]), lymphopenia (3 subjects [12.5%]), and hyperphosphatemia (2 subjects [8.3%]).

4. Serious TEAEs

IV Administration

Serious TEAEs were reported for 36 subjects (48.6%) treated with IV teclistamab. The following serious TEAEs were reported at ≥3 subjects: CRS (7 subjects); pneumonia (6 subjects); sepsis (5 subjects); pyrexia (4 subjects); and hypercalemia, pain in extremity, and acute kidney injury (3 subjects each).

SC Administration

Serious TEAEs were reported for 6 subjects (25.0%) treated with SC teclistamab. No preferred term was reported as serious in more than 1 subject.

5. Deaths

IV Administration

Twenty-two subjects treated with IV teclistamab died. Seventeen deaths were due to progressive disease, 2 deaths were due to AE, and 3 deaths were listed as due to "other" in the clinical database (1 subject due to glioblastoma and 2 subjects due to sepsis, 1 of which also had unconfirmed disease progression at the time of death). Three deaths occurred within the 30 days of the last dose of study drug, including 2 subjects with progressive disease and the subject noted above who died due to sepsis and unconfirmed disease progression.

SC Administration

Three subjects treated with SC teclistamab died. Death was due to progressive disease in 2 subjects and listed as due to "other" in the clinical database (worsening of health status). Two deaths, including that due to worsening status, occurred within 30 days of the last dose of study drug.

6. Adverse Events of Special Interest

CRS—IV Administration

Treatment-emergent symptoms of CRS were reported for 40 subjects (54.1%) treated with IV teclistamab. The following treatment-emergent symptoms of CRS were reported at ≥3 subjects: pyrexia (38 subjects); chills, hypotension, and sinus tachycardia (9 subjects each), headache (5 subjects), hypoxia (4 subjects), and aspartate aminotransferase increased (3 subjects).

The median onset time of CRS was 1 day from the most recent dose of study drug (range of 1 to 3 days), with median duration of 3 days (range of 1 to 6 days). Events of CRS resolved for all subjects. Thirty-seven subjects (50.0%) received supportive measures as treatment for CRS (18 subjects [24.3%] received tocilizumab, 13 subjects [17.6%] received corticosteroids, 1 subject [1.4%] received vasopressors, and 5 subjects [6.8%] received oxygen).

In IV Cohort 16 (270 µg/kg weekly treatment dose; n=11), 2 subjects (18.2%) had CRS with maximum severity of Grade 1 and 4 subjects (36.4%) had CRS with maximum severity of Grade 2. The median duration was 1 day (range 1 to 6 days). Three subjects had multiple events of CRS. Of the 3 other events of CRS reported in this cohort, 1 occurred following the first step-up dose, 1 occurred following the second step-up dose, and 1 occurred following the first treatment dose. Each of these subjects (all at the same site) were treated with tocilizumab.

In IV Cohort 17 (720 µg/kg weekly treatment dose; n=6), 2 subjects (33.3%) had CRS with maximum severity of Grade 1 and 1 subject (16.7%) had CRS with maximum severity of Grade 2. The median duration was 2 days (range 1 to 2 days). One subject had 4 events of CRS (second and third step-up doses and first and second treatment doses). One subject experienced CRS after the first step-up dose. These 2 subjects were treated with tocilizumab. A third subject was reported to have experienced CRS after the second treatment dose and did not receive tocilizumab.

CRS—SC Administration

Treatment-emergent symptoms of CRS were reported for 11 subjects (45.8%) treated with SC teclistamab. Pyrexia was reported 10 subjects, and no other treatment-emergent symptoms of CRS were reported in ≥3 subjects.

The median onset time of CRS was 2.0 days from the most recent dose of study drug (range of 2 to 3 days), with median duration of 1 day (range of 1 to 4 days). Events of CRS resolved for all subjects. Ten subjects (41.7%) received supportive measures as treatment for CRS (2 subjects [8.3%] received tocilizumab, 2 subjects [8.3%] received corticosteroids, no subjects received vasopressors, and 1 subject [4.2%] received oxygen).

In SC Cohort 3 and SC Cohort 4 (720 µg/kg weekly treatment dose; n=11), 7 subjects (63.6%) had CRS with maximum severity of Grade 1. More severe CRS was not reported in these cohorts to date. The median duration was 1 day (range 1 to 4 days). Four subjects had multiple events of CRS; only one of which was treated with tocilizumab. Of the 3 other events of CRS reported in these cohorts, 1 occurred following the first step-up dose, 1 occurred following the second step-up dose, and 1 occurred following the first treatment dose (1 of which was treated with tocilizumab).

Teclistamab-related Neurotoxicity—IV Administration

Six subjects (8.1%) treated with IV teclistamab experienced events of neurotoxicity that were at least possibly related to teclistamab. In 3 of the 6 subjects, the neurotoxicity resolved within 2 days. In the 4 subjects that continued treatment, none had additional teclistamab-related neurotoxicity.

Note that a Grade 5 AE of depressed level of consciousness reported in a subject treated with IV teclistamab who died (see above) was considered by the investigator not to be related to study drug, did not occur in the context of CRS, began after disease progression had occurred and worsened in grade after starting subsequent anticancer therapy.

Teclistamab-Related Neurotoxicity—SC Administration

No subjects treated with SC teclistamab experienced events of neurotoxicity that were at least possibly related to teclistamab.

E. Efficacy, First Data Cutoff

IV Administration

Figure 10:
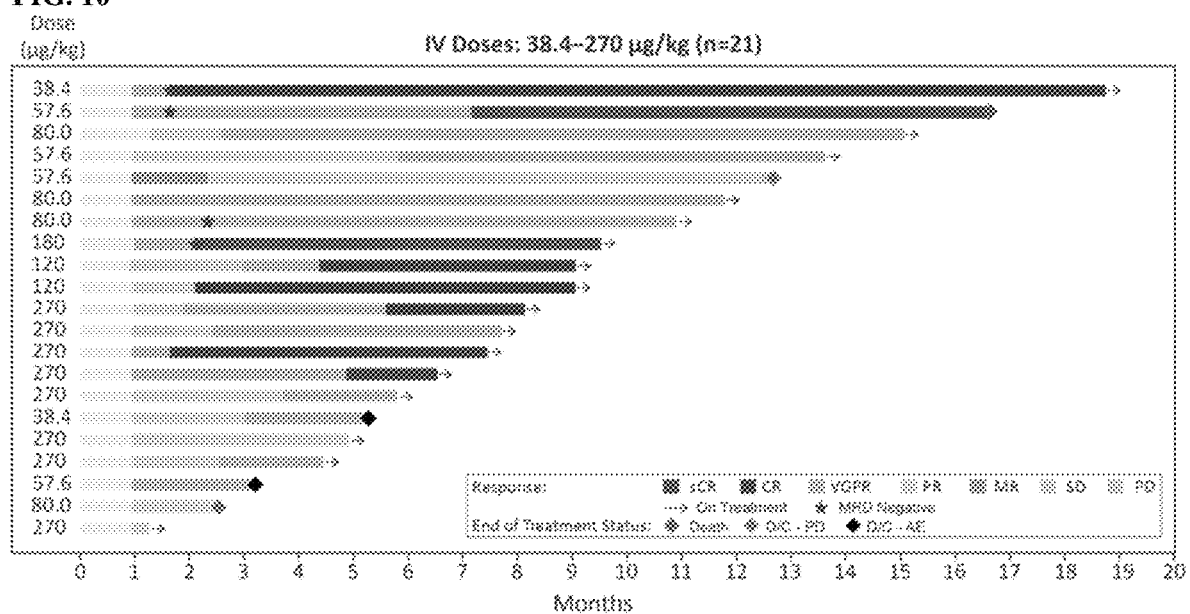
FIG. 10 shows the response and time on treatment in responders in intravenous dosing cohorts at the First Data Cutoff.

Sixty-seven subjects treated with IV teclistamab had ≥1 postdose disease evaluation as of the data cutoff (i.e., were evaluable for efficacy). The overall response rate (ORR; stringent complete response [sCR]+complete response [CR]+very good partial response [VGPR]+partial response [PR]) for all subjects treated with IV teclistamab was 28.4%, with 15 subjects having VGPR or better and 7 subjects having CR or better (Table 7; FIG. 10). The duration of treatment for responders was longer than those who did not respond. Twenty-eight subjects (41.8%) had stable disease and 19 subjects (28.4%) had progressive disease. Note that the data cutoff date for FIG. 10 was earlier than that for the text.

Responses occurred rapidly, with a median time to confirmed first response (PR or better) of 1 month (range of 1 to 3 months). The median times to confirmed CR or better and confirmed VGPR or better were 2.1 months (range of 1.6 to 7.2 months) and 1 month (1.0 to 5.8 months), respectively.

The median duration of follow-up for all subjects treated IV as of the data cutoff was 7.4 months (range of 0.3 to 27.0 months).

The first response in the dose escalation study was observed in a subject in IV Cohort 10 (treatment dose of weekly 38.4 µg/kg). For subjects treated in IV Cohort 10 and beyond (n=54), ORR was 35.2%, with specific responses noted above. The responses were observed to deepen over time in some subjects with ongoing response in 16/21 patients with response.

In IV Cohort 16 (270 µg/kg weekly treatment dose; n=9 evaluable subjects), ORR was 66.7%, with 2 subjects each (22.2%) having CR, VGPR, and PR (Table 7; FIG. 10). Median time to first confirmed response (PR or better) in this cohort was 0.95 months (range of 1.0 to 1.7 months). The median duration of follow-up for all subjects in IV Cohort 16 as of the data cutoff was 3.9 months (range of 0.3 to 6.3 months). These preliminary data suggest compelling efficacy in this population of heavily pretreated subjects.

TABLE 7

Summary of Overall Best Confirmed Response based on Investigator Assessment; mITT Analysis Set

|  | IV Total | 10/60 then 270 µg/kg (IV16) | 10/60/240, then 720 µg/kg weekly (IV17) | SC Total | 60/240 then 720 µg/kg weekly (SC3 and SC4) | Total |
|---|---|---|---|---|---|---|
| Analysis set: Modified intent-to-treat | 67 | 9 | 2 | 24 | 11 | 91 |
| Response category |  |  |  |  |  |  |
| Stringent complete response (sCR) | 2 (3.0%) | 0 | 0 | 0 | 0 | 2 (2.2%) |
| Complete response (CR) | 5 (7.5%) | 2 (22.2%) | 0 | 2 (8.3%) | 0 | 7 (7.7%) |
| Very good partial response (VGPR) | 8 (11.9%) | 2 (22.2%) | 0 | 4 (16.7%) | 2 (18.2%) | 12 (13.2%) |
| Partial response (PR) | 4 (6.0%) | 2 (22.2%) | 0 | 3 (12.5%) | 2 (18.2%) | 7 (7.7%) |
| Minimal response (MR) | 0 | 0 | 0 | 0 | 0 | 0 |
| Stable disease (SD) | 28 (41.8%) | 2 (22.2%) | 1 (50.0%) | 11 (45.8%) | 5 (45.5%) | 39 (42.9%) |
| Progressive disease (PD) | 19 (28.4%) | 1 (11.1%) | 0 | 4 (16.7%) | 2 (18.2%) | 23 (25.3%) |
| Not evaluable (NE) | 1 (1.5%) | 0 | 1 (50.0%) | 0 | 0 | 1 (1.1%) |
| Overall response (sCR + CR + VGPR + PR) | 19 (28.4%) | 6 (66.7%) | 0 | 9 (37.5%) | 4 (36.4%) | 28 (30.8%) |
| Clinical benefit (Overall response + MR) | 19 (28.4%) | 6 (66.7%) | 0 | 9 (37.5%) | 4 (36.4%) | 28 (30.8%) |
| VGPR or better (sCR + CR + VGPR) | 15 (22.4%) | 4 (44.4%) | 0 | 6 (25.0%) | 2 (18.2%) | 21 (23.1%) | mITT (Modified intent-to-treat): Subjects received at least one study treatment and were followed up for at least 1-month or had at least one response evaluation by investigator.
Note:
Response was assessed by investigators, based on IMWG Criteria.
Percentages were calculated with the number of subjects in each group as denominator SC Administration Twenty-four subjects treated with SC teclistamab had ≥1 postdose disease evaluation as of the data cutoff (ie, were evaluable for efficacy). The ORR was 37.5%, with 6 subjects having VGPR or better and 2 subjects having CR or better (Table 7).

Responses occurred rapidly, with a median time to first response (PR or better) of 1.6 months (range of 0.9 to 1.9 months). The duration of treatment for responders was longer than those who did not respond. Ten subjects (41.7%) had stable disease and 4 subjects (16.7%) had progressive disease.

Median time to first confirmed response (PR or better) was 1.6 months (range of 1 to 2 months). The median time to confirmed CR or better or confirmed VGPR or better was 2.7 months (range of 2.3 to 3.0 months) and 1.76 months (0.9 to 3.1 months), respectively.

The median duration of follow-up for all subjects treated SC as of the data cutoff was 3 months (range of 0.9 to 6.8 months).

In SC Cohort 3 and SC Cohort 4 (720 µg/kg weekly treatment dose; n=11 evaluable subjects), ORR was 36.4%, with 2 subjects each (18.2%) having VGPR and PR (Table 7). The median duration of responders in this cohort is discussed above. Median time to first confirmed response (PR or better) in these cohorts was 1.3 months (range of 0.9 to 1.6 months). The median duration of follow-up for all subjects in SC Cohort 3 and SC Cohort 4 as of the data cutoff was 1.9 months (range of 0.9 to 3.7 months).

MRD

Furthermore, two IV patients had durable MRD samples available for evaluation. Both patients exhibited durable MRD negativity at approximately 5 and 14 mos post their first MRD negative sample. Both patients were deemed negative at $10^{-5}$ and one patient was also deemed negative at $10^{-6}$. For the one patient not deemed MRD negative at the upper threshold of $10^{-6}$, this was a consequence of having insufficient cellular material to properly evaluate MRD negativity at $10^{-6}$.

In conclusion, Teclistamab treated patients in the study with evaluable samples displayed an 85.7% MRD negativity rate, achieved MRD negativity with both IV and SC administration routes and exhibited durable MRD negativity up to 14 mos post the first MRD negativity sample.

F. Clinical Pharmacokinetics, First Data Cutoff

IV Administration

At the time of the datacutoff, preliminary PK data was available from 65 subjects treated with IV teclistamab who were evaluable for PK at doses ranging from 0.3 to 19.2 µg/kg Q2W (Cohorts 1-7) or doses ranging from 19.2 to 720 µg/kg weekly (Cohorts 8-17).

Figure 11A:
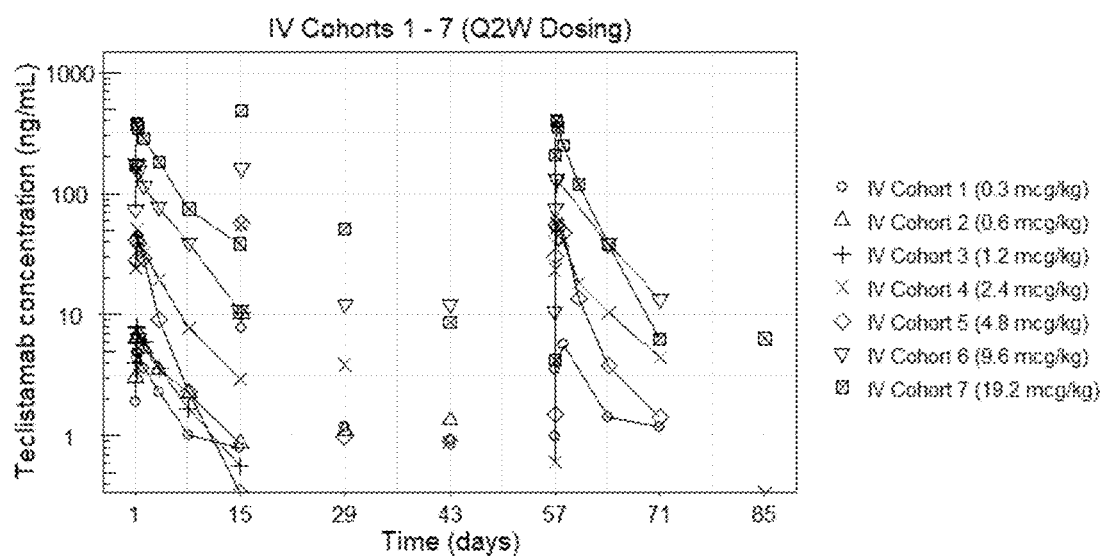
FIG. 11A shows a serum concentration-time profile of Teclistamab following IV infusion with Q2W or weekly dosing in subjects with multiple myeloma for Cohorts 1-7 at the First Data Cutoff.
Figure 11B:
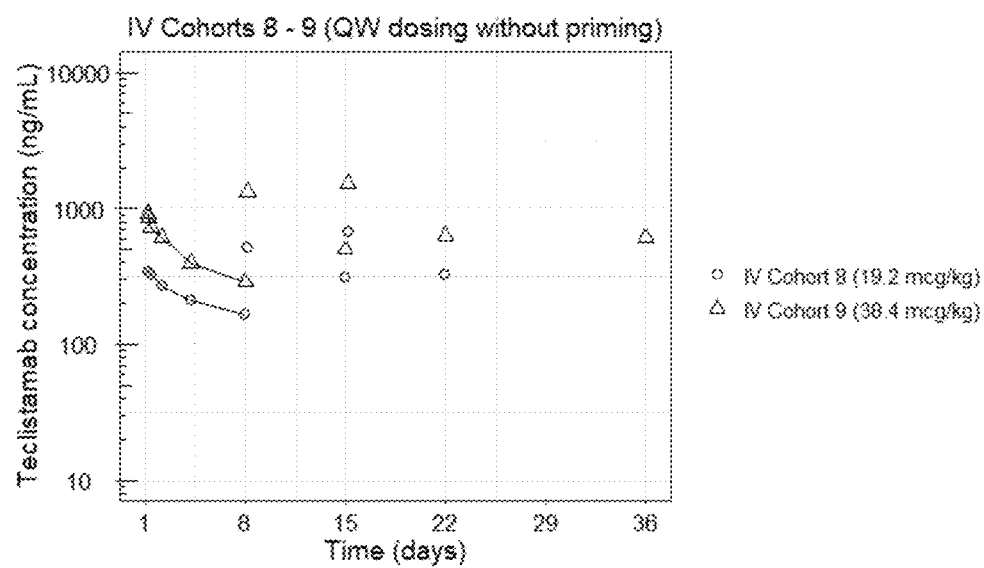
FIG. 11B shows a serum concentration-time profile of Teclistamab following IV infusion with Q2W or weekly dosing in subjects with multiple myeloma for Cohorts 8-9 at the First Data Cutoff.
Figure 11C:
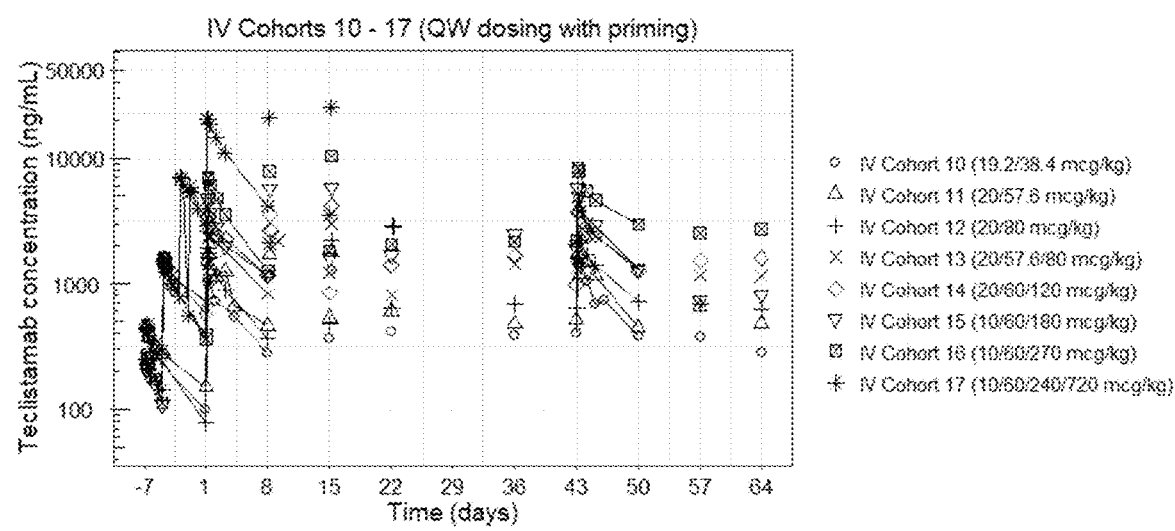
FIG. 11C shows a serum concentration-time profile of Teclistamab following IV infusion with Q2W or weekly dosing in subjects with multiple myeloma for Cohorts 10-17 at the First Data Cutoff.

Preliminary PK results following multiple IV infusions of teclistamab in Cycle 3 showed that weekly dosing had no to minimum drug accumulation with mean accumulation ratio (based on $AUC_{tau}$) ranging from 0.61 to 1.57-fold. Steady state exposure increased in an approximately dose-proportional manner across the range of 38.4 to 270 µg/kg weekly (Cohorts 10-16). Teclistamab concentration-time profiles following IV administration are presented in FIG. 11.

G. Clinical Pharmacodynamics, First Data Cutoff

Flow cytometry and soluble cytokine factors were assessed to determine the ability of monotherapy Teclistamab to show anticipated pharmacodynamic (PD) mechanisms of action inclusive of cytokine induction, transient drops in T cells (T cell redistribution) and T cell activation. Exploratory biomarker flow cytometry testing was performed by Navigate BioPharma Services (Carlsbad, Calif., USA) and cytokine assessments by ARUP laboratories (Salt Lake City, Utah, USA) using whole blood samples from all evaluable (a baseline sample and at least one post treatment sample) subjects.

IV Administration

Data were available for 74 IV subjects evaluable for pharmacodynamics in the study. Data for IV teclistamab doses given Q2W (treatment doses ranging from 0.3 to 19.2 µg/kg) and weekly (treatment doses ranging from 19.2 to 270 µg/kg) were included. Following step-up dose(s) and treatment doses in the first cycle, subjects exhibited pharmacodynamic changes that were characteristic of the mechanism of action for teclistamab at all doses ≥9.6 µg/kg teclistamab. These included total T cell activation as evidenced by increased CD25 expression on CD3$^+$ T cells (median maximum fold change 1.71 [range of 0.21 to 8.86]) and observations of T cell redistribution and infrequent expansion as indicated by total T cell absolute counts (0.32; 0.01-19.07). Consistent increases in several cytokines occurred during administration of step-up dose(s) and the first cycle; in particular, these included IL-10 (19.22; 0.17-1124.00), IL-6 (3.50; 1.00-204.00) and IL-2Rα (2.32; 0.51-27.72).

SC Administration

Data were available for 24 SC subjects evaluable for pharmacodynamics in the study. Data for SC teclistamab doses given weekly (treatment doses ranging from 19.2 to 270 µg/kg) were included. Following step-up dose(s) and treatment doses in the first cycle, subjects exhibited pharmacodynamic changes that were characteristic of the mechanism of action for teclistamab at all doses. These included total T cell activation as evidenced by increased CD25 expression on CD3$^+$ T cells (median maximum fold change 1.98 [range of 0.22 to 7.70]) and observations of T cell redistribution and infrequent expansion as indicated by total T cell absolute counts (0.11; 0.01-1.92). Consistent increases in several cytokines occurred during administration of step-up dose(s) and the first cycle; in particular, these included IL-10 (4.65; 1.60-65.60), IL-6 (3.00; 0.26-41.60) and IL-2Rα (1.95; 1.95-9.48). Of note, the cytokine production observed was attenuated compared with IV administration.

The most pronounced cytokine inductions occurred with analytes IL-10, IL-6 and IL-2Rα. These cytokines showed longitudinal induction patterns that frequently resolved before the next administered dose. T cell activation soluble factor IL-2Rα (soluble CD25) showed an increase post step up and full dosing (FIG. 12B). Cytokine monitoring demonstrated that step up dosing regimens allowed a manageable cytokine induction profile in support of lower grade cytokine release syndrome, T cell activation, and efficacious dosing of Teclistamab.

Figure 12A:
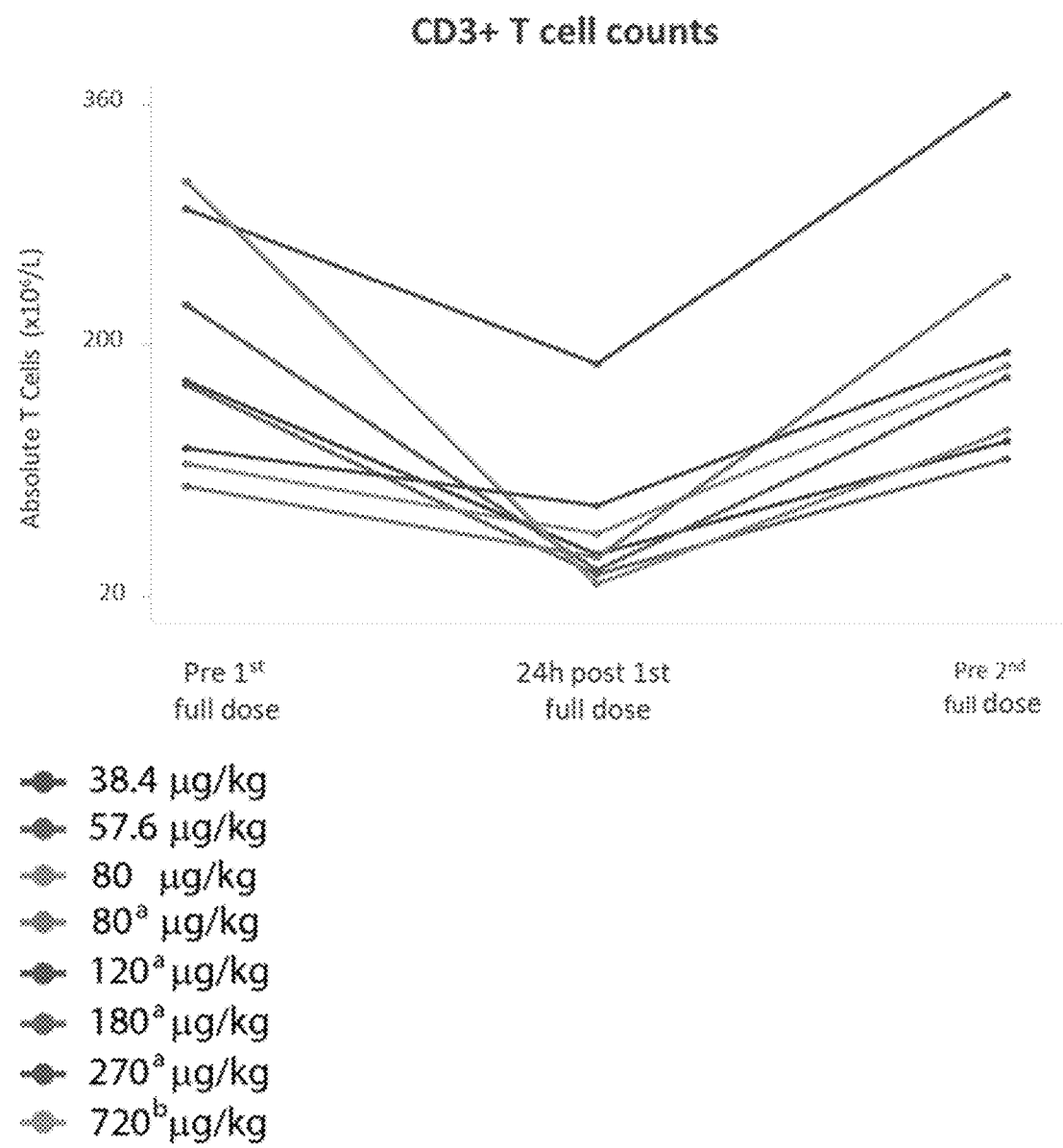
FIG. 12A shows levels of CD3+ T cells in response to teclistamab treatments at the First Data Cutoff.
Figure 12B:
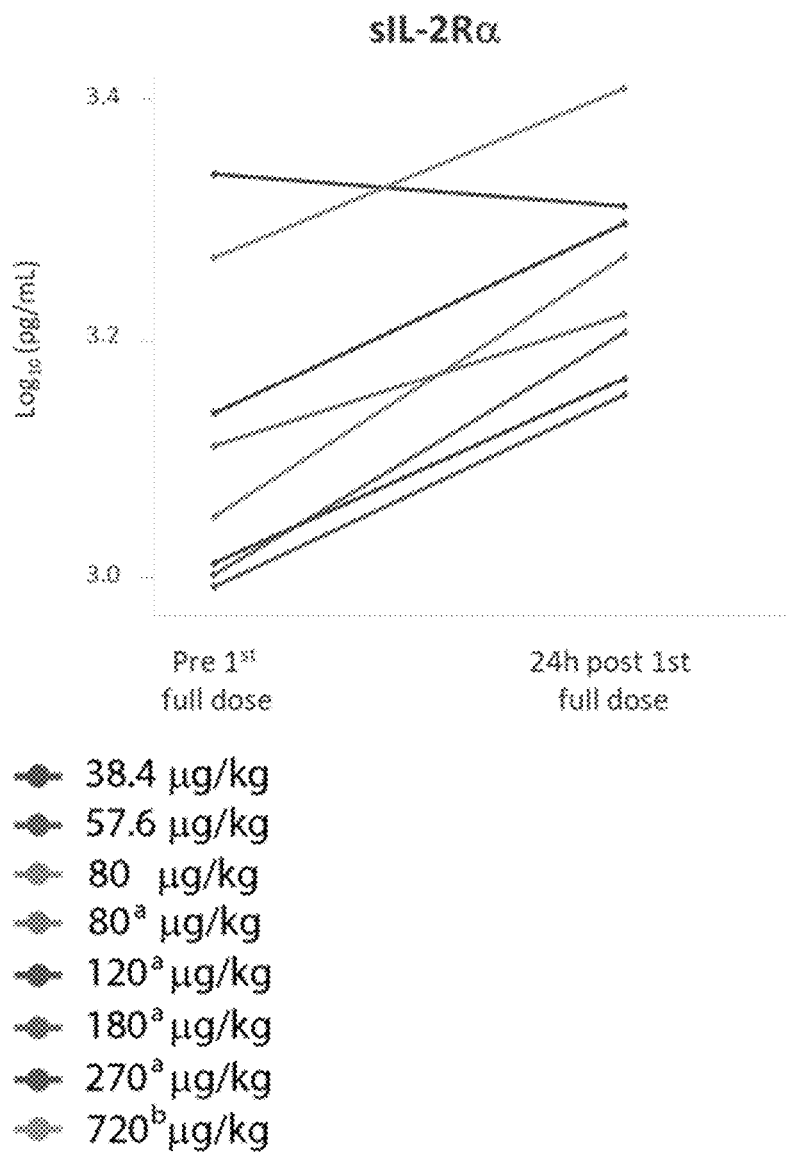
FIG. 12B shows levels of T cell activation soluble factor IL-2Rα in response to teclistamab treatments at the First Data Cutoff.

Flow cytometry assessments of peripheral blood absolute T cell counts pre-dose, 24 hrs post dose and pre-dose of the subsequent treatment revealed a transient drop in T cells (FIG. 12A). This drop was hypothesized to facilitate trafficking of the effector cells to the site of action. However, currently available assays do not have the capability to track every T cell in a patient, yet this PD phenomenon has been observed in other redirector therapeutics that have obtained efficacious treatment in myeloma and other hematological malignancies (i.e. blinatumomab).

In conclusion, Teclistamab treated patients with evaluable samples displayed a transient increase in cytokines, an increase in soluble IL-2Rα and a transient drop in peripheral blood T cell counts that were consistent with the anticipated mechanism of action.

H. Conclusions, First Data Cutoff

Teclistamab had a manageable safety profile across all doses assessed: all CRS events (56%) were grade 1-2 and generally confined to first step-up and full doses; step-up dosing mitigated high-grade CRS; there was a low incidence of neurotoxic events which were predominantly grade 1-2.

Greater responses were reached at higher doses: in advanced patient population at the 270 µg/kg IV dose, ORR was 64% with 55%≥VGPR; early responses were also observed at the 720 µg/kg IV dose with shorter follow-up; durable responses of up to 18 months were observed; 16/20 patients had ongoing response at time of data cut-off; 4/5 patient were MRD-negative at $10^{-6}$, and 2/2 evaluable patients had durable MRD negativity.

I. Study Population and Duration of Treatment, Second Data Cutoff

A second data cutoff took place in February 2021.

Figure 15A:
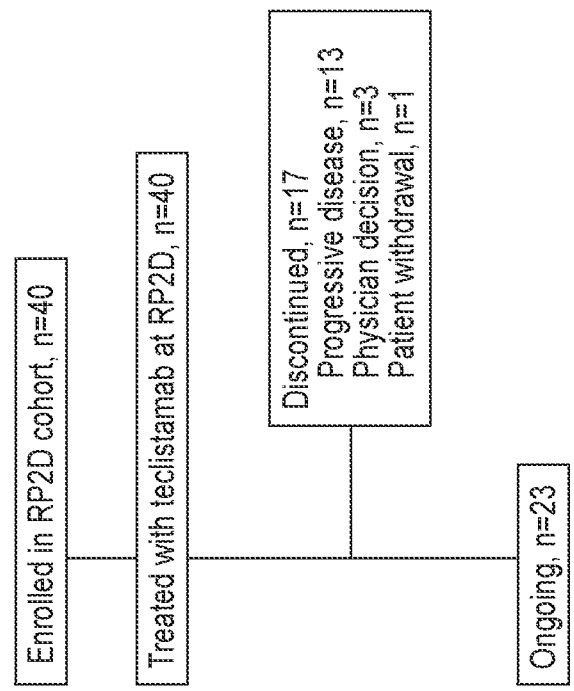
FIG. 15A shows a CONSORT (Consolidated Standards of Reporting Trials) diagram for the total population.
Figure 15B:
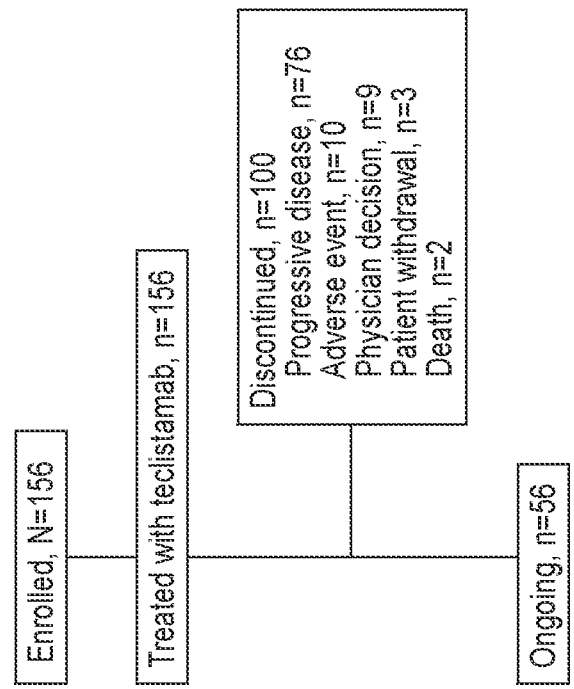
FIG. 15B shows a CONSORT diagram for the RP2D cohort.

Between Jun. 8, 2017 and Feb. 4, 2021, 155 patients were enrolled and received ≥1 dose of teclistamab; 153 patients with ≥1 post-baseline response evaluation were included in efficacy analyses. A total of 100 patients (64.1%) discontinued treatment due to progressive disease (48.7%), physician decision (5.8%), adverse event (6.4%), patient withdrawal (1.9%), and death (0.6%) (FIG. 15). In the overall population, median age was 63.0 years (range, 24-84), 54.5% of patients were male, and 32.5% had a high-risk cytogenetic profile (Table 8). Patients had received a median of six prior lines of therapies (range, 2-14); 81.4% were triple-class refractory, 38.5% were penta-drug refractory, and 90.4% were refractory to their last line of therapy. Baseline characteristics of patients in the dose cohort identified as the RP2D (n=40) were generally consistent with those in the overall population (Table 8).

Teclistamab was administered intravenously to 84 patients (biweekly, n=12 and weekly n=72) and subcutaneously to 72 patients. The dose range was 0.3-19.2 µg/kg for biweekly intravenous dosing, 19.2-720 µg/kg for weekly intravenous dosing, and 80.0-3000 µg/kg for subcutaneous dosing, with step-up dosing employed for full doses ≥38.4 µg/kg. There were two DLTs in weekly intravenous cohorts (grade 4 delirium [at 20.0 µg/kg step-up dose in a patient assigned to 120 µg/kg cohort] and grade 4 thrombocytopenia, in the context of CRS and disseminated intravascular coagulation [180 µg/kg full dose]), and none with subcutaneous dosing. The MTD of teclistamab was not reached. However, collective safety, efficacy, pharmacokinetic, and pharmacodynamic data (described in detail below) supported a weekly subcutaneous dose of 1500 µg/kg teclistamab as the RP2D.

TABLE 8

Detailed Baseline Characteristics

| Characteristic | Total (N = 156)* | Weekly 1500 µg/kg Subcutaneous Cohort† (n = 40) |
|---|---|---|
| Median age (range) - yr | 63.0 (24-84) | 62.5 (39-84) |
| Aged ≥70 yr - No. (%) | 34 (21.8) | 9 (22.5) |
| Sex - No. (%) | | |
| Male | 85 (54.5) | 26 (65.0) |
| Female | 71 (45.5) | 14 (35.0) |
| Race - no. (%) | | |
| White | 128 (82.1) | 31 (77.5) |
| Black | 7 (4.5) | 1 (2.5) |
| Asian | 2 (1.3) | 0 |
| Other | 3 (1.9) | 1 (2.5) |
| Unknown | 3 (1.9) | 0 |
| Not reported | 13 (8.3) | 7 (17.5) |
| Median time since diagnosis (range) - yr | 6.7 (0.5-26.2) | 5.7 (0.8-17.4) |
| Extramedullary plasmacytomas ≥1 - No. (%) | 18 (11.5) | 8 (20.0) |
| Bone marro plasma cells ≥60% - No. (%) | 34 (23.6) | 3 (8.6) |
| ECOG performance-status score - No. (%) | | |
| 0 | 61 (39.1) | 17 (42.5) |
| 1 | 95 (60.9) | 23 (57.5) |
| ISS stage - No. (%)‡ | | |
| I | 75 (48.4) | 24 (61.5) |
| II | 48 (31.0) | 11 (28.2) |
| III | 32 (20.6) | 4 (10.3) |
| High-risk cytogenetic profile, - No. (%)§ | 38 (32.5) | 10 (37.0) |
| del(17p) | 24 (20.5) | 7 (25.9) |
| t(4:14) | 17 (14.5) | 4 (14.8) |
| t(14;16) | 6 (5.1) | 1 (3.7) |
| Median no. of lines of prior therapies for multiple myeloma (range) | 6.0 (2-14) | 5.0 (2-11) |
| Previous autologous stem-cell transplantation - No. (%) | 133 (85.3) | 34 (85.0) |
| Prior proteasome inhibitor - No. (%) | | |
| Any proteasome inhibitor ‖ | | |
| Exposed | 156 (100) | 40 (100) |
| Refractory | 139 (89.1) | 35 (87.5) |
| Bortezomib | | |
| Exposed | 150 (96.2) | 39 (97.5) |
| Refractory | 97 (62.2) | 22 (55.0) |
| Carfilzomib | | |
| Exposed | 123 (78.8) | 32 (80.0) |
| Refractory | 104 (66.7) | 27 (67.5) |
| Ixazomib | | |
| Exposed | 30 (19.2) | 9 (22.5) |
| Refractory | 19 (12.2) | 5 (12.5) |

TABLE 8-continued

Detailed Baseline Characteristics

| Characteristic | Total (N = 156)* | Weekly 1500 μg/kg Subcutaneous Cohort† (n = 40) |
|---|---|---|
| Prior immunomodulatory drug - No. (%) | | |
| Any immunomodulatory drug ¶ | | |
| Exposed | 156 (100) | 40 (100) |
| Refractory | 151 (96.8) | 38 (95.0) |
| Lenalidomide | | |
| Exposed | 153 (98.1) | 39 (97.5) |
| Refractory | 138 (88.5) | 34 (85.0) |
| Pomalidomide | | |
| Exposed | 129 (82.7) | 31 (77.5) |
| Refractory | 119 (76.3) | 28 (70.0) |
| Thalidomide | | |
| Exposed | 50 (32.1) | 12 (30.0) |
| Refractory | 21 (13.5) | 5 (12.5) |
| Prior anti-CD38 antibody - No. (%) | | |
| Any anti-CD38 antibody ** | | |
| Exposed | 150 (96.2) | 40 (100) |
| Refractory | 145 (92.9) | 39 (97.5) |
| Daratumumab | | |
| Exposed | 147 (94.2) | 40 (100) |
| Refractory | 142 (91.0) | 39 (97.5) |
| Isatuximab | | |
| Exposed | 4 (2.6) | 0 |
| Refractory | 4 (2.6) | 0 |
| Triple-class exposed - No. (%)†† | 150 (96.2) | 40 (100) |
| Triple-class refractory - No. (%)†† | 127 (81.4) | 33 (82.5) |
| Penta-drug exposed - No. (%)‡‡ | 107 (68.6) | 26 (65.0) |
| Penta-drug refractory - No. (%)‡‡ | 60 (38.5) | 14 (35.0) |
| Refractory to last line of therapy - No. (%) | 141 (90.4) | 34 (85.0) |

ECOG, Eastern Cooperative Oncology Group; ISS, International Staging System
*Biweekly intravenous, n = 12; weekly intravenous, n = 72; weekly subcutaneous, n = 72.
†Step-up doses of 60.0 and 300 μg/kg.
‡Denominator is evaluable patients, n = 144 in total population and n = 35 in weekly 1500 μg/kg subcutaneous cohort.
§Derived based on the combination of serum β2-microglobulin and albumin; missing for one patient.
|| Denominator is evaluable patients, n = 117 in total population and n = 27 in weekly 1500 μg/kg subcutaneous cohort.
¶ Bortezomib, carfilzomib, and/or ixazomib.
** Thalidomide, lenalidomide, and/or pomalidomide.
††Daratumumab and/or isatuximab.
‡‡At least one proteasome inhibitor, at least one immunomodulatory drug, and one anti-CD38 antibody.
§§ At least two proteasome inhibitors, at least two immunomodulatory drugs, and one anti-CD38 antibody.

J. Safety, Second Data Cutoff

In the overall population, 155 patients (99.4%) had AEs, and 130 (83.3%) had grade 3/4 AEs; in the cohort treated at the RP2D, 39 patients (97.5%) had AEs, and 28 (70.0%) had grade 3/4 AEs (Tables 9 and 10). Grade 3/4 AEs were considered treatment-related in 76 patients (48.7%) across all cohorts and in 21 (52.5%) in the RP2D cohort. Ten (6.4%) patients discontinued teclistamab due to AEs, with one (delirium) considered-treatment-related; no AEs led to treatment discontinuation in the RP2D cohort.

TABLE 9

Adverse Events Reported in ≥15% of patients in the overall population

| | Total (N = 156) | | Weekly 1500 μg/kg Subcutaneous Cohort† (n = 40) | |
|---|---|---|---|---|
| Variable - No. (%) | Any Grade | Grade 3/4 | Any Grade | Grade 3/4 |
| Any adverse event | 155 (99.4) | 130 (83.3) | 39 (97.5) | 28 (70.0) |
| Hematologic | | | | |
| Neutropenia | 94 (60.3) | 76 (48.7) | 24 (60.0) | 16 (40.0) |
| Anemia | 90 (57.7) | 52 (33.3) | 19 (47.5) | 11 (27.4) |
| Thrombocytopenia | 67 (42.9) | 36 (23.1) | 18 (45.0) | 8 (20.0) |
| Leukopenia | 44 (28.2) | 23 (14.7) | 13 (32.5) | 7 (17.5) |
| Nonhematologic | | | | |
| Cytokine release syndrome | 89 (57.1) | 0 | 28 (70.0) | 0 |
| Pyrexia | 47 (30.1) | 0 | 7 (17.5) | 0 |
| Diarrhea | 41 (26.3) | 2 (1.3) | 8 (20.0) | 1 (2.5) |
| Fatigue | 39 (25.0) | 2 (1.3) | 12 (30.0) | 1 (2.5) |
| Nausea | 39 (25.0) | 1 (0.6) | 10 (25.0) | 0 |
| Headache | 37 (23.7) | 0 | 8 (20.0) | 0 |
| Cough | 36 (23.1) | 3 (1.9) | 4 (10.0) | 0 |
| Back pain | 29 (18.6) | 3 (1.9) | 2 (5.0) | 1 (2.5) |
| Upper respiratory tract infection | 29 (18.6) | 0 | 2 (5.0) | 0 |

TABLE 9-continued

Adverse Events Reported in ≥15% of patients in the overall population

| | Total (N = 156) | | Weekly 1500 µg/kg Subcutaneous Cohort† (n = 40) | |
|---|---|---|---|---|
| Variable - No. (%) | Any Grade | Grade 3/4 | Any Grade | Grade 3/4 |
| Arthralgia | 26 (16.7) | 3 (1.9) | 4 (10.0) | 1 (2.5) |
| Vomiting | 24 (15.4) | 1 (0.6) | 8 (20.0) | 0 |

†Step-up doses of 60.0 and 300 µg/kg.

with first onset of grade 3/4 hematologic Aes during step-dosing or cycle 1/2 was 51.3% for neutropenia, 90.4% for anemia, and 83.3% for thrombocytopenia.

The most common nonhematologic AE was CRS, which occurred in 89 (57.1%) patients overall and 28 (70.0%) treated at the RP2D; all CRS events were grade 1/2. Median time to CRS onset relative to the most recent teclistamab dose was 1.0 day (range, 1-3) with intravenous dosing (i.e., the day of intravenous infusion) and 2.0 days (range, 1-5) with subcutaneous dosing (i.e., the day after subcutaneous injection); median duration was 1.0 (range, 1-7) and 2.0 days (range, 1-31), respectively (Table 11). CRS was generally confined to the step-up and first full doses (data not shown). In all, 23.7% of patients (32.5% in RP2D cohort) received

TABLE 10

Adverse Events Reported in ≥10% of Patients in the Overall Population

| | Total (N = 156) | | Intravenous Cohorts (n = 84) | | Subcutaneous Cohorts (n = 72) | |
|---|---|---|---|---|---|---|
| Variable - No. (%) | Any grade | Grade 3/4 | Any grade | Grade 3/4 | Any grade | Grade 3/4 |
| Any adverse event | 155 (99.4) | 130 (83.3) | 84 (100) | 76 (90.5) | 71 (98.6) | 54 (75.0) |
| Hematologic disorders | 133 (85.3) | 117 (75.0) | 74 (88.1) | 68 (81.0) | 59 (81.9) | 49 (68.1) |
| Neutropenia | 94 (60.3) | 76 (48.7) | 50 (59.5) | 44 (52.4) | 44 (61.1) | 32 (44.4) |
| Anemia | 90 (57.7) | 52 (33.3) | 54 (64.3) | 33 (39.3) | 36 (50.0) | 19 (26.4) |
| Thrombocytopenia | 67 (42.9) | 36 (23.1) | 37 (44.0) | 21 (25.0) | 30 (41.7) | 15 (20.8) |
| Leukopenia | 44 (28.2) | 23 (14.7) | 25 (29.8) | 14 (16.7) | 19 (26.4) | 9 (12.5) |
| Lymphopenia | 22 (14.1) | 21 (13.5) | 15 (17.9) | 14 (16.7) | 7 (9.7) | 7 (9.7) |
| General disorders and administration site conditions | 106 (67.9) | 8 (5.1) | 53 (63.1) | 4 (4.8) | 53 (73.6) | 4 (5.6) |
| Pyrexia | 47 (30.1) | 0 | 30 (35.7) | 0 | 17 (23.6) | 0 |
| Fatigue | 39 (25.0) | 2 (1.3) | 21 (25.0) | 1 (1.2) | 18 (25.0) | 1 (1.4) |
| Injection site erythema | 20 (12.8) | 0 | 0 | 0 | 20 (27.8) | 0 |
| Peripheral edema | 19 (12.2) | 2 (1.3) | 10 (11.9) | 0 | 9 (12.5) | 2 (2.8) |
| Infections and infestations | 91 (58.3) | 25 (16.0) | 57 (67.9) | 19 (22.6) | 34 (47.2) | 6 (8.3) |
| Upper respiratory tract infection | 29 (18.6) | 0 | 21 (25.0) | 0 | 8 (11.1) | 0 |
| Pneumonia | 16 (10.3) | 8 (5.1) | 11 (13.1) | 7 (8.3) | 5 (6.9) | 1 (1.4) |
| Respiratory tract infection | 16 (10.3) | 3 (1.9) | 12 (14.3) | 2 (2.4) | 4 (5.6) | 1 (1.4) |
| Musculoskeletal And Connective Tissue Disorders | 85 (54.5) | 16 (10.3) | 48 (57.1) | 8 (9.5) | 37 (51.4) | 8 (11.1) |
| Back Pain | 29 (18.6) | 3 (1.9) | 21 (25.0) | 1 (1.2) | 8 (11.1) | 2 (2.8) |
| Arthralgia | 26 (16.7) | 3 (1.9) | 13 (15.5) | 2 (2.4) | 13 (18.1) | 1 (1.4) |
| Myalgia | 17 (10.9) | 0 | 10 (11.9) | 0 | 7 (9.7) | 0 |
| Pain in extremity | 16 (10.3) | 3 (1.9) | 10 (11.9) | 3 (3.6) | 6 (8.3) | 0 |
| Gastrointestinal disorders | 81 (51.9) | 4 (2.6) | 43 (51.2) | 2 (2.4) | 38 (52.8) | 2 (2.8) |
| Diarrhea | 41 (26.3) | 2 (1.3) | 25 (29.8) | 1 (1.2) | 16 (22.2) | 1 (1.4) |
| Nausea | 39 (25.0) | 1 (0.6) | 19 (22.6) | 1 (1.2) | 20 (27.8) | 0 |
| Vomiting | 24 (15.4) | 1 (0.6) | 12 (14.3) | 1(1.2) | 12 (16.7) | 0 |
| Constipation | 17 (10.9) | 0 | 10 (11.9) | 0 | 7 (9.7) | 0 |
| Metabolism and nutrition disorders | 77 (49.4) | 25 (16.0) | 44 (52.4) | 14 (16.7) | 33 (45.8) | 11 (15.3) |
| Hypocalcemia | 22 (14.1) | 0 | 16 (19.0) | 0 | 6 (8.3) | 0 |
| Hypomagnesemia | 21 (13.5) | 0 | 12 (14.3) | 0 | 9 (12.5) | 0 |
| Hypokalemia | 21 (13.5) | 4 (2.6) | 11 (13.1) | 1 (1.2) | 10 (13.9) | 3 (4.2) |
| Hypophosphatemia | 20 (12.8) | 11 (7.1) | 10 (11.9) | 6 (7.1) | 10 (13.9) | 5 (6.9) |
| Decreased appetite | 19 (12.2) | 2 (1.3) | 9 (10.7) | 1 (1.2) | 10 (13.9) | 1 (1.4) |
| Other* | | | | | | |
| Cytokine release syndrome | 89 (57.1) | 0 | 45 (53.6) | 0 | 44 (61.1) | 0 |
| Headache | 37 (23.7) | 0 | 20 (23.8) | 0 | 17 (23.6) | 0 |
| Cough | 36 (23.1) | 3 (1.9) | 23 (27.4) | 2 (2.4) | 13 (18.1) | 1 (1.4) |
| Aspartate aminotransferase increased | 22 (14.1) | 1 (0.6) | 14 (16.7) | 1 (1.2) | 8 (11.1) | 0 |
| Dizziness | 20 (12.8) | 0 | 12 (14.3) | 0 | 8 (11.1) | 0 |
| Alanine aminotransferase increased | 18 (11.5) | 1 (0.6) | 11 (13.1) | 1 (1.2) | 7 (9.7) | 0 |

*Two or fewer preferred terms in system organ class.

Hematologic AEs were commonly reported (Table 9); the most frequent grade 3/4 hematologic AEs in the overall population and RP2D cohort were neutropenia (48.7% and 40.0%, respectively), anemia (33.3% and 27.4%, respectively), and thrombocytopenia (23.1% and 20.0%, respectively). In the overall population, the proportion of patients tocilizumab and 14.7% (12.5% in RP2D cohort) received steroids as supportive measures for CRS. CRS resolved in all 89 patients. Other nonhematologic AEs reported in ≥25% of patients were pyrexia (not associated with CRS; 30.1%; 17.5% at RP2D), diarrhea (26.3%; 20.0% at RP2D), fatigue (25.0%; 30.0% at RP2D), and nausea (25.0%; 25.0% at RP2D); common nonhematologic AEs were generally grade 1/2 and similar with intravenous and subcutaneous dosing (Table 10).

TABLE 11

Characteristics and Management of CRS

| Variable | Intravenous Dosing Cohorts (n = 84) | Subcutaneous Dosing Cohorts (n = 72) | Total (N = 156) |
|---|---|---|---|
| Patients with a CRS event - No. (%) | 45 (53.6) | 44 (61.1) | 89 (57.1) |
| Maximum toxicity grade - No. (%) | | | |
| Grade 1 | 32 (38.1) | 32 (44.4) | 64 (41.0) |
| Grade 2 | 13 (15.5) | 12 (16.7) | 25 (16.0) |
| Median time to onset relative to most recent dose (range), days | 1.0 (1-3) | 2.0 (1-5) | 2.0 (1-5) |
| Median duration (range), days | 1.0 (1-7) | 2.0 (1-31) | 2.0 (1-31) |
| Supportive measures - No. (%)* | 43 (51.2) | 41 (56.9) | 84 (53.8) |
| Tocilizumab | 22 (26.2) | 15 (20.8) | 37 (23.7) |
| Steroids | 16 (19.0) | 7 (9.7) | 23 (14.7) |
| Oxygen | 6 (7.1) | 4 (5.6) | 10 (6.4) |
| Vasopressor | 1 (1.2) | 0 | 1 (0.6) |
| Other | 42 (50.0) | 39 (54.2) | 81 (51.9) |

CRS, cytokine release syndrome.
*Patients may have received more than one supportive measure for CRS.

Infections were reported in 85 patients (54.5%; grade 3/4, 15.4%), including 14 (35.0%; grade 3/4, 7.5%) treated at the RP2D. Neurotoxicity (all-grade) occurred in seven patients (4.5%), with one grade 1 event (2.5%) in the RP2D cohort; two patients had grade 3/4 neurotoxicity events with intravenous dosing and none with subcutaneous dosing (Table 12). Infusion reactions were reported in four patients across intravenous cohorts (4.8%), and injection-site reactions were reported in 29 patients across subcutaneous cohorts (40.3%), including 20 (50.0%) treated at the RP2D; all events were grade 1/2.

Serious AEs occurred in 73 patients (46.8%) overall and in 14 (35.0%) treated at the RP2D (Table 13). Serious AEs reported in ≥5% of patients were CRS (8.3% overall; 5.0% at RP2D), pneumonia (6.4%; 0 at RP2D), and sepsis (5.8%; 2.5% at RP2D). Twenty-six patients (16.7%) had serious AEs considered related to teclistamab, including three (7.5%) in the RP2D cohort.

TABLE 12

Neurotoxicities Related to Teclistamab as Assessed by the Investigator

| Variable - No. (%) | Total (N = 156) | Weekly 1500 μg/kg Subcutaneous Cohort* (n = 40) |
|---|---|---|
| Any neurotoxicity | 7 (4.5) | 1 (2.5) |
| Nervous system disorders | 4 (2.6) | 1 (2.5) |
| Aphasia | 1 (0.6) | 0 |
| Dysgraphia | 1 (0.6) | 0 |
| Paresthesia | 1 (0.6) | 0 |
| Speech Disorder | 1 (0.6) | 0 |
| Tremor | 1 (0.6) | 1 (2.5) |
| Psychiatric Disorders | 4 (2.6) | 0 |
| Confusional State | 2 (1.3) | 0 |
| Bradyphrenia | 1 (0.6) | 0 |
| Delirium | 1 (0.6) | 0 |
| Mental Status Changes | 1 (0.6) | 0 |

*Step-up doses of 60.0 and 300 μg/kg.

TABLE 13

Serious Adverse Events Reported in ≥2% of Patients in the Overall Population

| Variable - No. (%) | Total (N = 156) | Weekly 1500 μg/kg Subcutaneous Cohort* (n = 40) |
|---|---|---|
| Any serious adverse event | 73 (46.8) | 14 (35.0) |
| Cytokine release syndrome | 13 (8.3) | 2 (5.0) |
| Pneumonia | 9 (5.8) | 1 (2.5) |
| Sepsis | 9 (5.8) | 1 (2.5) |
| Pyrexia | 6 (3.8) | 1 (2.5) |
| Acute kidney injury | 5 (3.2) | 1 (2.5) |

*Step-up doses of 60.0 and 300 μg/kg.

There were 49 deaths during the study, with 33 due to disease progression, six due to AEs that occurred ≤100 days after the last teclistamab dose or before start of subsequent systemic anticancer therapy, and ten for other reasons (Table 14). One AE leading to death (pneumonia in a patient in the 80.0 μg/kg weekly intravenous dosing cohort) was considered treatment-related by the investigator; the remaining AEs leading to death (COVID-19 [n=2] and depressed level of consciousness in the context of ongoing pneumonia, respiratory failure, and sepsis [n=1 each]) were considered unrelated to teclistamab.

TABLE 14

Summary of Deaths During the Study

| Primary Cause - No. (%) | Total (N = 156) |
|---|---|
| Disease progression | 33 (21.2) |
| Adverse event | 6 (3.8) |
| Related to treatment | 1 (0.6) |
| Pneumonia | n = 1 |
| Unrelated to treatment | 5 (3.2) |
| COVID-19 | n = 2 |
| Depressed level of consciousness | n = 1 |
| Respiratory failure | n = 1 |
| Sepsis | n = 1 |
| Other* | 10 (6.4) |
| Brain cancer (glioblastoma) | n = 1 |
| Sepsis | n = 1 |
| Sepsis/multiple myeloma | n = 1 |
| Bilateral pneumonia with respiratory failure | n = 1 |
| COVID-19 infection | n = 1 |
| Worsening of health status | n = 1 |
| Pathology report of autopsy not in yet | n = 1 |
| Respiratory failure | n = 1 |
| Graft failure after allogeneic hematopoietic cell transplantation | n = 1 |
| Unknown | n = 1 |

*All causes except worsening of health status and unknown occurred after start of subsequent therapy.

K. Efficacy, Second Data Cutoff

Median duration of follow-up was 14.1 months (range, 0.6-38.3+) across intravenous dosing cohorts and 7.1 months (1.1-17.6+) across subcutaneous dosing cohorts. Responses to teclistamab in evaluable patients in all cohorts are shown in Tables 15-17. Similar efficacy was seen at the RP2D compared with weekly intravenous doses ≥270 µg/kg and subcutaneous doses ≥720 µg/kg (Table 18). Across these five dose levels, ORR was 67.4% and 62.8% of patients achieved a very good partial response or better (≥VGPR); median duration of response was not reached.

TABLE 15

Response to Teclistamab in Evaluable Patients in Biweekly Intravenous Dosing Cohorts*

| Variable | 0.3 µg/kg (n = 1) | 0.6 µg/kg (n = 1) | 1.2 µg/kg (n = 1) | 2.4 µg/kg (n = 3) | 4.8 µg/kg (n = 2) | 9.6 µg/kg (n = 1) | 19.2 µg/kg (n = 2) |
|---|---|---|---|---|---|---|---|
| Best overall response - No. (%) | | | | | | | |
| Stringent complete response | 0 | 0 | 0 | 0 | 0 | 0 | 0 |
| Complete response | 0 | 0 | 0 | 0 | 0 | 0 | 0 |
| Very good partial response | 0 | 0 | 0 | 0 | 0 | 0 | 0 |
| Partial response | 0 | 0 | 0 | 0 | 0 | 0 | 0 |
| Stable disease | 1 (100) | 1 (100) | 0 | 2 (66.7) | 1 (50.0) | 1 (100) | 2 (100) |
| Progressive disease | 0 | 0 | 1 (100) | 1 (33.3) | 1 (50.0) | 0 | 0 |
| Overall response - No. (%)† | 0 | 0 | 0 | 0 | 0 | 0 | 0 |
| Very good partial response or better - No. (%) | 0 | 0 | 0 | 0 | 0 | 0 | 0 |
| Complete response or better - No. (%) | 0 | 0 | 0 | 0 | 0 | 0 | 0 |

*Investigator assessment of evaluable patients who had at least one dose of teclistamab and at least one postbaseline disease evaluation; includes unconfirmed responses.
†Includes stringent complete response, complete response, very good partial response, and partial response.

TABLE 16

Response to Teclistamab in Evaluable Patients in Weekly Intravenous Dosing Cohorts*

| Variable | 19.2 µg/kg (n = 1) | 38.4 µg/kg (n = 1) | 38.4 µg/kg (n = 4)† | 57.6 µg/kg (n = 10)‡ | 80.0 µg/kg (n = 12)‡ | 80.0 µg/kg (n = 5)§ | 120 µg/kg (n = 6)‖ | 180 µg/kg (n = 6)¶ | 270 µg/kg (n = 12)¶ | 720 µg/kg (n = 15)** | Total (n = 83) |
|---|---|---|---|---|---|---|---|---|---|---|---|
| Best overall response - No. (%) | | | | | | | | | | | |
| Stringent complete response | 0 | 0 | 0 | 2 (20.0) | 0 | 0 | 0 | 1 (16.7) | 0 | 1 (6.7) | 4 (4.8) |
| Complete response | 0 | 0 | 1 (25.0) | 0 | 1 (8.3) | 0 | 2 (33.3) | 0 | 5 (41.7) | 3 (20.0) | 12 (14.5) |
| Unconfirmed - No.†† | 0 | 0 | 0 | 0 | 1 | 0 | 0 | 0 | 0 | 0 | 1 |
| Very good partial response | 0 | 0 | 1 (25.0) | 1 (10.0) | 1 (8.3) | 1 (20.0) | 0 | 0 | 3 (25.0) | 6 (40.0) | 13 (15.7) |
| Partial response | 0 | 0 | 0 | 1 (10.0) | 1 (8.3) | 0 | 0 | 0 | 1 (8.3) | 0 | 3 (3.6) |
| Stable disease | 0 | 1 (100) | 1 (25.0) | 2 (20.0) | 6 (50.0) | 0 | 2 (33.3) | 4 (66.7) | 1 (8.3) | 2 (13.3) | 27 (32.5) |
| Progressive disease | 1 (100) | 0 | 1 (25.0) | 4 (40.0) | 3 (25.0) | 4 (80.0) | 2 (33.3) | 1 (16.7) | 2 (16.7) | 3 (20.0) | 24 (28.9) |
| Overall response - No. (%)‡‡ | 0 | 0 | 2 (50.0) | 4 (40.0) | 3 (25.0) | 1 (20.0) | 2 (33.3) | 1 (16.7) | 9 (75.0) | 10 (66.7) | 32 (38.6) |
| Very good partial response or better - No. (%) | 0 | 0 | 2 (50.0) | 3 (30.0) | 2 (16.7) | 1 (20.0) | 2 (33.3) | 1 (16.7) | 8 (66.7) | 10 (66.7) | 29 (34.9) |
| Complete response or better - No. (%) | 0 | 0 | 1 (25.0) | 2 (20.0) | 1 (8.3) | 0 | 2 (33.3) | 1 (16.7) | 5 (41.7) | 4 (26.7) | 16 (19.3) |

IMWG, International Myeloma Working Group.
*Investigator assessment of evaluable patients who had at least one dose of teclistamab and at least one postbaseline disease evaluation; includes unconfirmed responses.
†Step-up dose of 19.2 µg/kg.
‡Step-up dose of 20.0 µg/kg.
§Step-up doses of 20.0 and 57.6 µg/kg.
‖Step-up doses of 20.0 and 60.0 µg/kg.
¶Step-up doses of 10.0 and 60.0 µg/kg.
**Step-up doses of 10.0, 60.0 and 240 µg/kg.
††Patients meet all criteria of complete response per IMWG criteria.
‡‡Includes stringent complete response, complete response, very good partial response, and partial response.

TABLE 17

Response to Teclistamab in Evaluable Patients in Weekly Subcutaneous Dosing Cohorts*

| Variable | 80.0 µg/kg (n = 6)† | 240 µg/kg (n = 7)‡ | 720 µg/kg (n = 15)§ | 1500 µg/kg (n = 40)‖ | 3000 µg/kg (n = 4)¶ | Total (n = 72) |
|---|---|---|---|---|---|---|
| Best overall response - No. (%) | | | | | | |
| Stringent complete response | 0 | 0 | 2 (13.3) | 5 (12.5) | 0 | 7 (9.7) |
| Complete response | 2 (33.3) | 2 (28.6) | 3 (20.0) | 7 (17.5) | 1 (25.0) | 15 (20.8) |
| Unconfirmed - No.** | 0 | 0 | 0 | 2 | 0 | 2 |
| Very good partial response | 1 (16.7) | 1 (14.3) | 4 (26.7) | 11 (27.5) | 3 (75.0) | 20 (27.8) |
| Unconfirmed - No.†† | 0 | 0 | 0 | 2 | 0 | 2 |
| Partial response | 0 | 0 | 0 | 3 (7.5) | 0 | 3 (4.2) |
| Unconfirmed - No.‡‡ | 0 | 0 | 0 | 2 | 0 | 2 |
| Stable disease | 2 (33.3) | 2 (28.6) | 2 (13.3) | 8 (20.0) | 0 | 14 (19.4) |
| Progressive disease | 1 (16.7) | 2 (28.6) | 4 (26.7) | 6 (15.0) | 0 | 13 (18.1) |
| Overall response - No. (%)§§ | 3 (50.0) | 3 (42.9) | 9 (60.0) | 26 (65.0) | 4 (100) | 45 (62.5) |
| Very good partial response or better - No. (%) | 3 (50.0) | 3 (42.9) | 9 (60.0) | 23 (57.5) | 4 (100) | 42 (58.3) |
| Complete response or better - No. (%) | 2 (33.3) | 2 (28.6) | 5 (33.3) | 12 (30.0) | 1 (25.0) | 22 (30.6) |

*Investigator assessment of evaluable patients who had at least one dose of teclistamab and at least one postbaseline disease evaluation; includes unconfirmed responses.
†Step-up dose of 20.0 µg/kg.
‡Step-up doses of 40.0 and 80.0 µg/kg.
§Step-up doses of 60.0 and 240 µg/kg.
‖Step-up doses of 60.0 and 300 µg/kg.
¶Step-up doses of 60.0, 300, and 1500 µg/kg.
**Patients meet all criteria of complete response per IMWG criteria.
††Patients meet all criteria of very good partial response per IMWG criteria.
‡‡Patients meet all criteria of partial response per IMWG criteria.
§§Includes stringent complete response, complete response, very good partial response, and partial response.

TABLE 18

Response to Teclistamab in Evaluable Patients in Treated at the RP2D and Other Active Dose Levels*

| Variable | Weekly 1500 µg/kg Subcutaneous Cohort (n = 40)† | Other Weekly Intravenous Cohorts (≥270 µg/kg) and Subcutaneous Cohorts (≥720 µg/kg) (n = 46)‡ |
|---|---|---|
| Best overall response - No. (%) | | |
| Stringent complete response | 5 (12.5) | 3 (6.5) |
| Complete response | 7 (17.5) | 12 (26.1) |
| Unconfirmed - No.§ | 2 | 0 |
| Very good partial response | 11 (27.5) | 16 (34.8) |
| Unconfirmed - No.‖ | 2 | 0 |
| Partial response | 3 (7.5) | 1 (2.2) |
| Unconfirmed - No.¶ | 2 | 0 |
| Stable disease | 8 (20.0) | 5 (10.9) |
| Progressive disease | 6 (15.0) | 9 (19.6) |
| Overall response - No. (%)** | 26 (65.0) | 32 (69.6) |
| Very good partial response or better - No. (%) | 23 (57.5) | 31 (67.4) |
| Complete response or better No. (%) | 12 (30.0) | 15 (32.6) |
| Median time to first confirmed response (range) - mo | 1.0 (0.2-3.1) | 1.0 (0.7-10.6) |
| Median time to first confirmed very good partial response or better (range) - mo | 1.0 (0.2-4.6) | 1.7 (0.7-6.0) |
| Median time to first confirmed complete response or better (range) - mo | 2.3 (1.6-4.4) | 4.4 (1.6-11.3) |
| Median duration of response (95% CI) - mo | NR (5.8-NR) | NR (10.0-NR) |

IMWG, International Myeloma Working Group; NR, not reached; RP2D, recommended phase 2 dose.
*Investigator assessment of evaluable patients who had at least one dose of teclistamab and atleast one postbaseline disease evaluation; includes unconfirmed responses.
†Step-up doses of 10.0 and 60.0 µg/kg.
‡Weekly intravenous doses of 270 and 720 µg/kg and weekly subcutaneous doses of 720 and 3000 µg/kg.
§Patients meet all criteria of complete response per IMWG criteria.
‖Patients meet all criteria of very good partial response per IMWG criteria.
¶Patients meet all criteria of partial response per IMWG criteria.
**Includes stringent complete response, complete response, very good partial response, and partial response.

Median duration of follow-up for all patients treated at the RP2D was 4.3 months (range, 1.1-10.4+). In response-evaluable patients treated at the RP2D (n=40), the ORR was 65.0%; 57.5% achieved ≥VGPR, and 30.0% achieved CR or better (≥CR). In 33 response-evaluable patients treated at the RP2D who were triple-class refractory, the ORR was 60.6%. Median time to first confirmed response was 1.0 month (range, 0.2-3.1), to first confirmed VGPR was 1.0 month (range, 0.2-4.6), and to first confirmed ≥CR was 2.3 months (range, 1.6-4.4) in the RP2D cohort. Median duration of response was not reached.

Figure 13A:
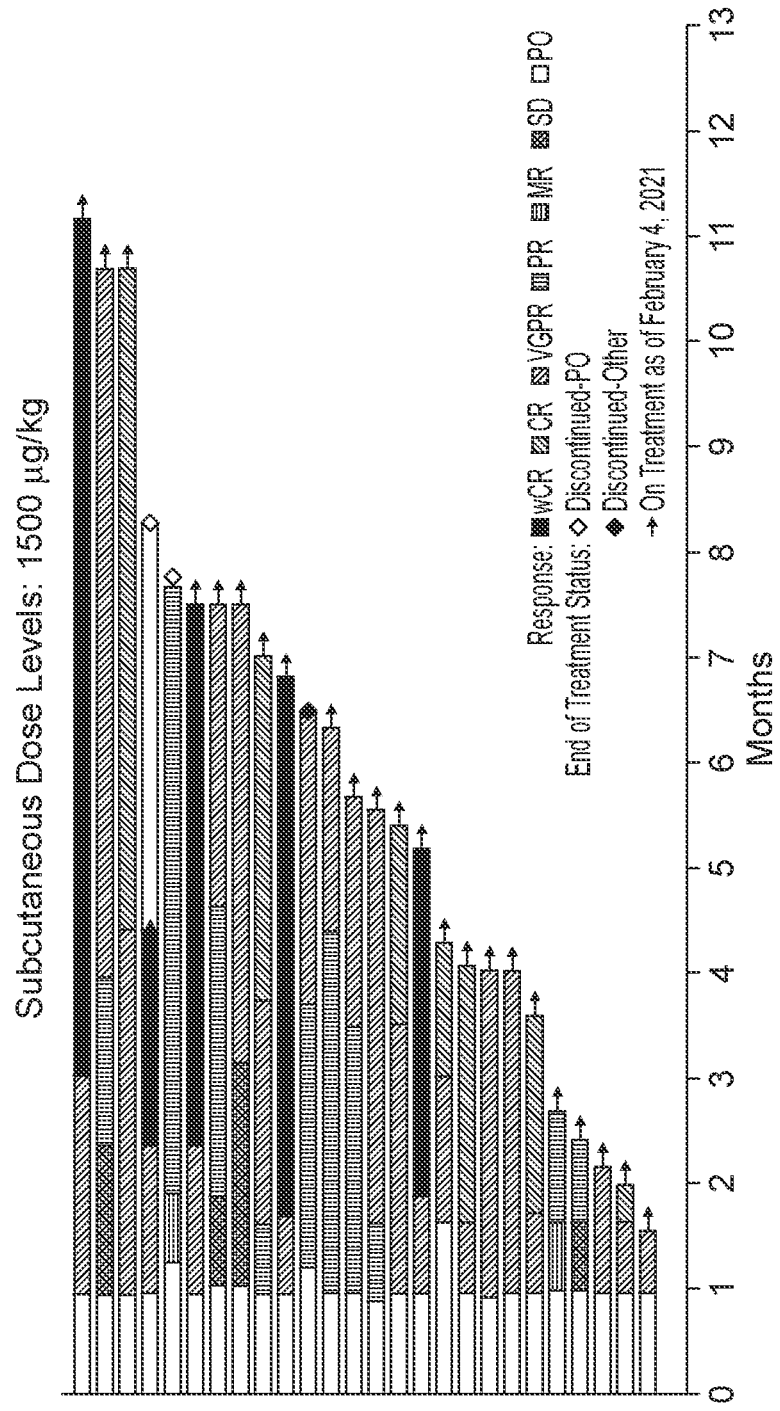
FIG. 13A shows the duration of response in patients treated at the RP2D of Teclistamab at the Second Data Cutoff.
Figure 13B:
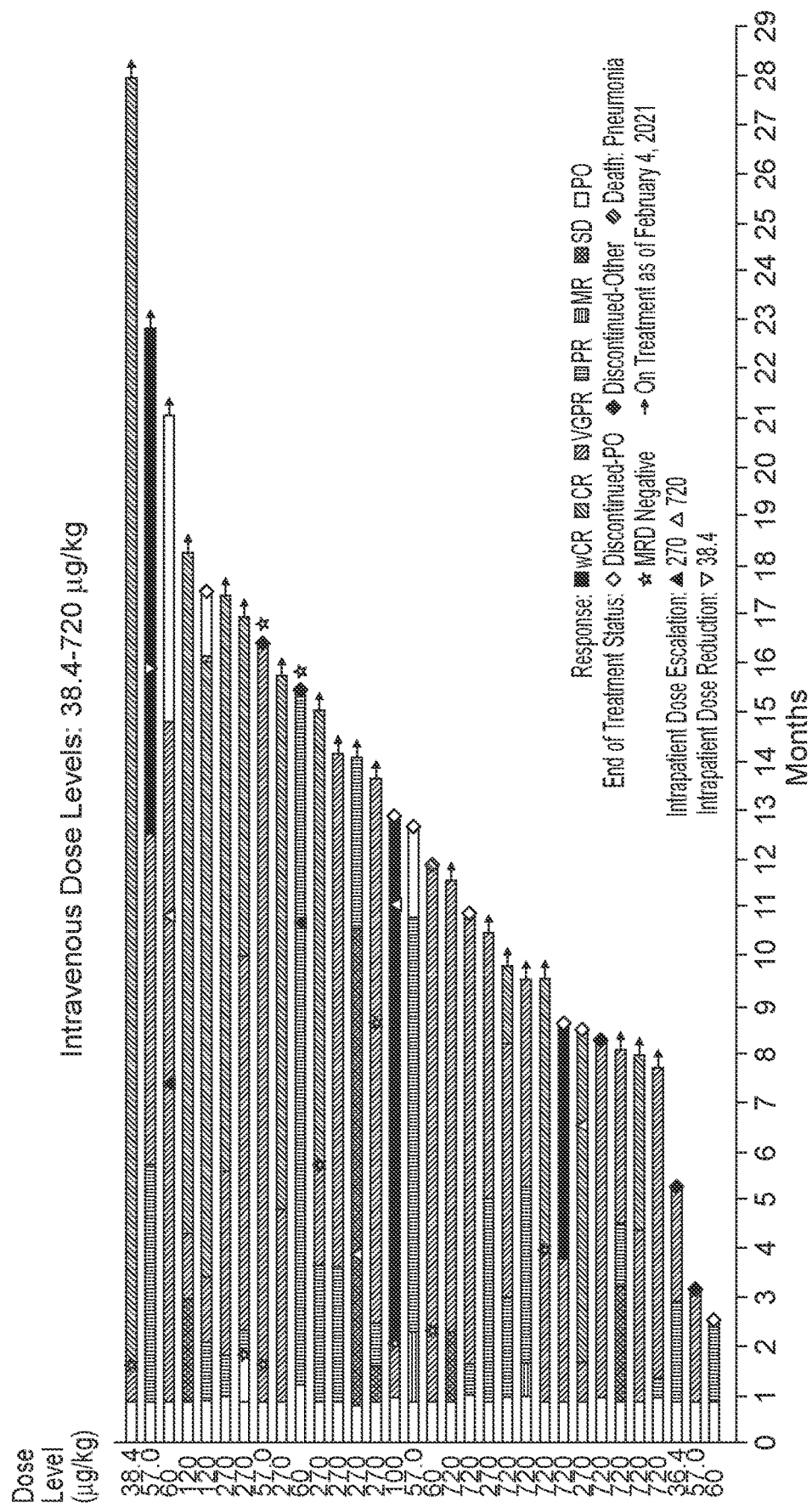
FIG. 13B shows the duration of response in patients in the intravenous dosing cohorts at the Second Data Cutoff.

Responses were durable and deepened over time at the RP2D and in other cohorts (FIG. 13). Among 26 responders treated at the RP2D (median follow-up, 5.3 months [range, 1.2-10.4+]), 23 (88.5%) were alive and continuing on treatment. Given the observed deepening of responses over time, applicants assessed the first 22 patients treated at the RP2D, who comprised a cohort with a median of ≥6 months of follow-up (median, 6.3 months [range, 1.4-10.4+]; in this group, ORR was 72.7%, with 68.2% achieving ≥VGPR and 36.4% achieving ≥CR.

Minimal Residual Disease

Of 26 patients with complete response across all cohorts, 14 had MRD-evaluable samples. Three of 26 patients were missing baseline samples. Of the remaining 23 patients with baseline samples available for MRD analysis, ten samples failed baseline calibration (eight biological failures, one technical failure and one uniqueness failure) and two additional samples were not confirmed complete responses. One patient had a repeated MRD sample collected 14 months after complete response for sustained MRD analysis.

Of 14 evaluable patients across all cohorts, nine had MRD-negative CR or stringent CR at $10^{-6}$. MRD negativity was sustained 14 months after CR in one evaluable patient.

Figure 14A:
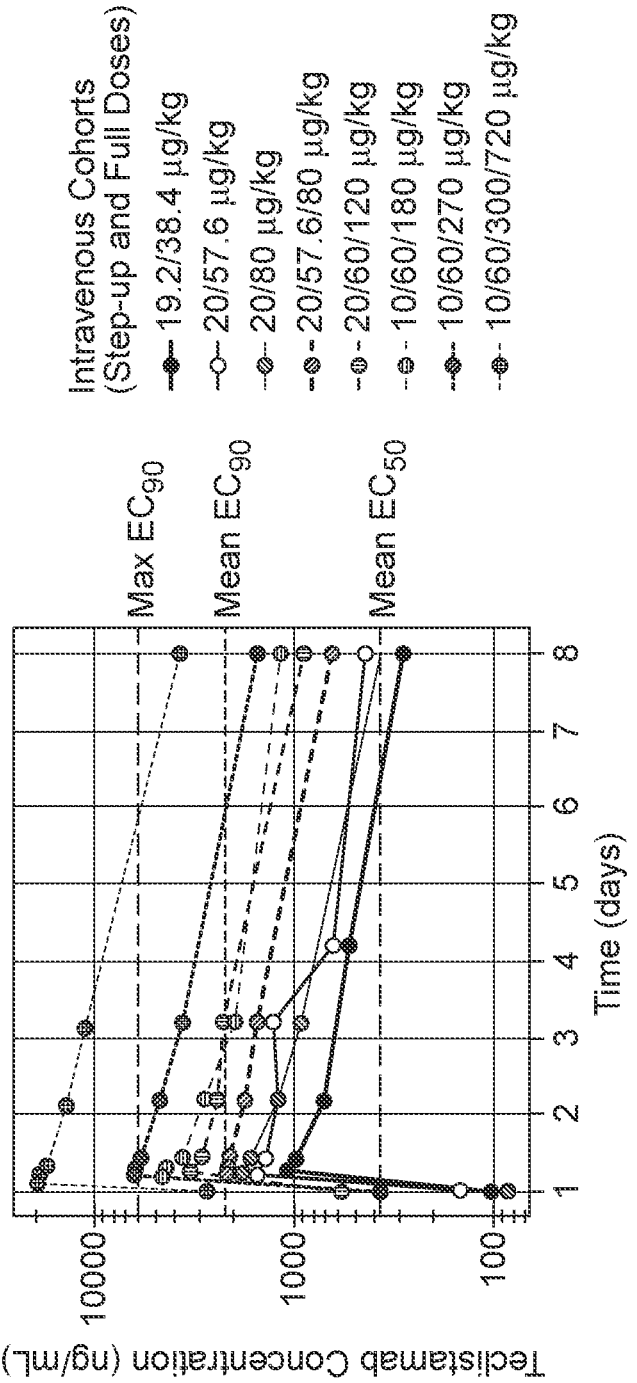
FIG. 14A shows the mean Teclistamab concentrations in the first week following the first full dose of Teclistamab in selected intravenous dosing cohorts, with $EC_{90}$ values from ex vivo cytotoxicity assay using bone marrow mononuclear cells from patients with multiple myeloma.
Figure 14B:
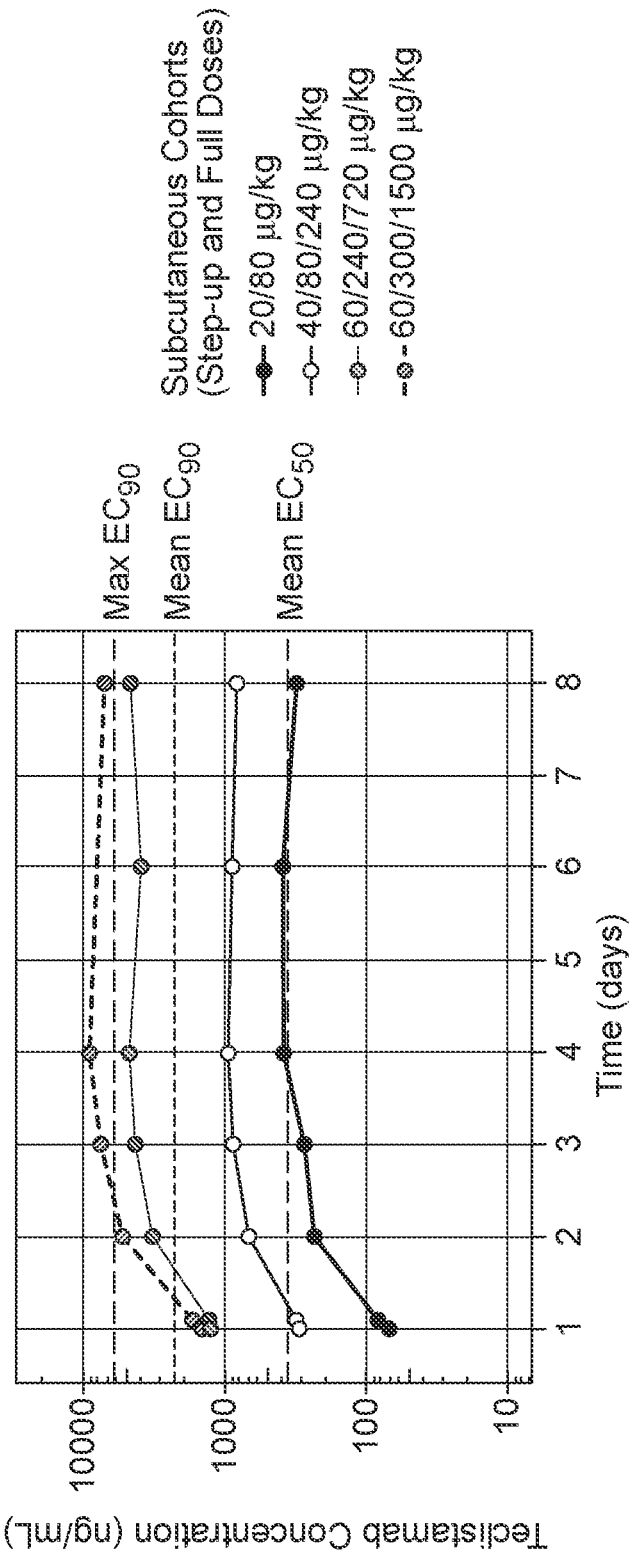
FIG. 14B shows the mean Teclistamab concentrations in the first week following the first full dose of Teclistamab in selected subcutaneous dosing cohorts, with $EC_{90}$ values from ex vivo cytotoxicity assay using bone marrow mononuclear cells from patients with multiple myeloma.

L. Clinical Pharmacokinetics, Pharmacodynamics, and Immunogenicity. Second Data Cutoff Preliminary pharmacokinetic results showed that following intravenous teclistamab administration, maximum concentrations ($C_{max}$) occurred at the end of infusion in most patients and declined rapidly (FIG. 14A). Following the first subcutaneous dose, teclistamab concentrations increased gradually (FIG. 14B), and $C_{max}$ was ~4.5-fold lower than with the dose-normalized intravenous dose. Individual time to $C_{max}$ occurred during days 3-8 after subcutaneous injection. Mean trough levels following the first teclistamab dose were comparable between similar intravenous and subcutaneous weekly doses. Following subcutaneous weekly dosing, mean accumulation was 1.8-3.9-fold. Exposure increased in an approximately dose-proportional manner following multiple subcutaneous dosing across the 80-3000 µg/kg range. Preliminary population pharmacokinetic analysis showed that soluble BCMA levels did not appear to impact teclistamab exposure (data not shown). At the RP2D, mean teclistamab trough levels exceeded the target 90% maximal effective concentration ($EC_{90}$) in an ex vivo cytotoxicity assay (using bone marrow mononuclear cells from patients with MM) (Girgis S, Lin S S X, Pillarisetti K, et al. Translational Approach of Using Ex Vivo Cytotoxicity and Early Clinical Data to Predict Teclistamab Efficacious Therapeutic Range in Multiple Myeloma Patients. Blood 2020;136 (Supplement 1):35) (FIG. 14B).

Figure 14C:
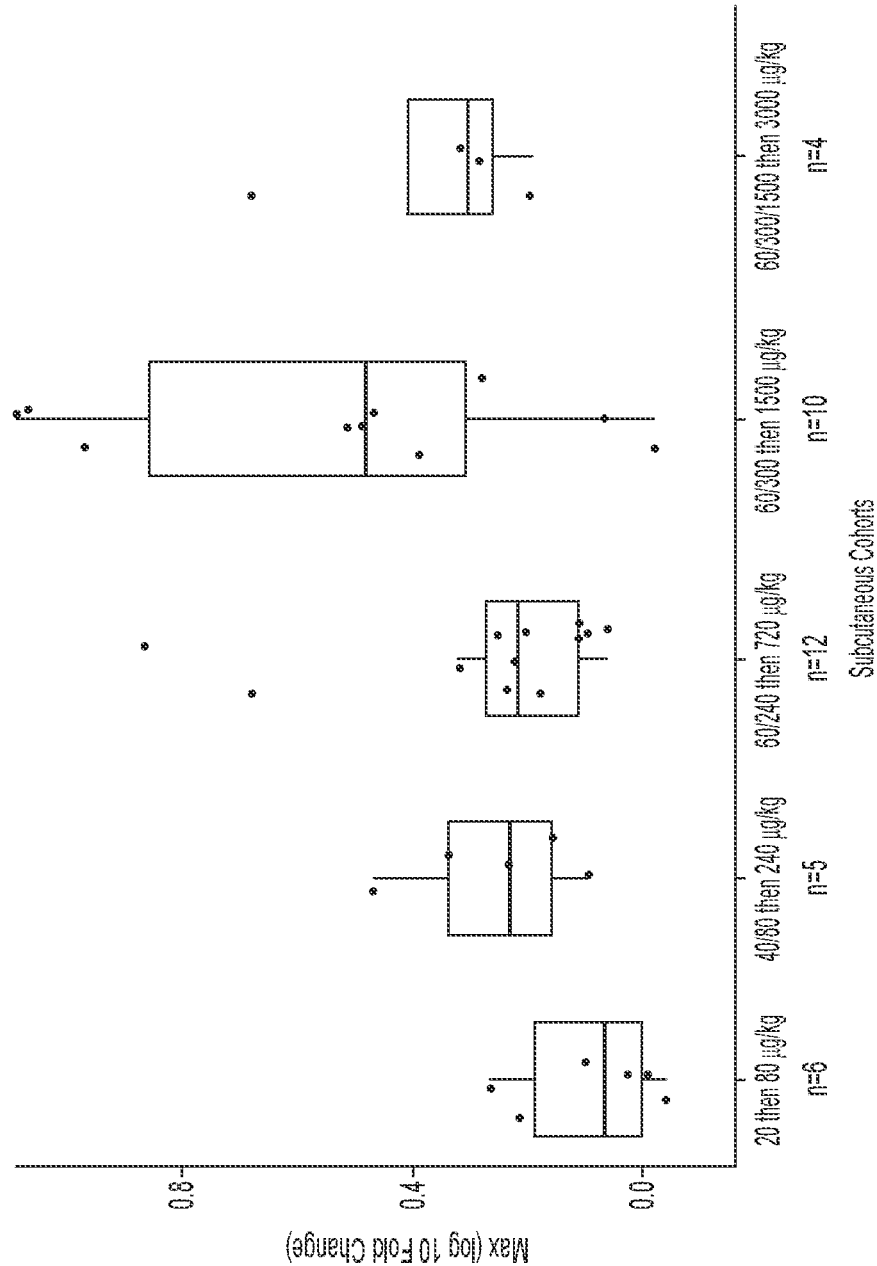
FIG. 14C shows induction of programmed cell death protein-1-positive T cells in subcutaneous dosing cohorts at the Second Data Cutoff.

After weekly subcutaneous teclistamab administration, programmed cell death protein-1-positive T cells were induced in the periphery, with consistent T-cell activation observed at the RP2D (FIG. 14C). Findings were similar with other markers of T-cell activation (data not shown). Consistent increases in cytokines, were observed following teclistamab subcutaneous administration, with higher induction seen in higher dose cohorts, including the RP2D (data not shown).

Anti-teclistamab antibodies at low titers (equal to the minimum required dilution of the assay [1:20]) were detected in two of 107 evaluable patients (1.9%), one in the 80.0 µg/kg intravenous cohort and one in the 240 µg/kg subcutaneous cohort. Anti-teclistamab antibodies did not appear to have an impact on safety or pharmacokinetics in these patients.

M. Conclusions

In this first-in-human study of teclistamab, a weekly 1500 µg/kg subcutaneous dose was selected as the RP2D based on collective safety, efficacy, pharmacokinetic, and pharmacodynamic data. At the RP2D, teclistamab was well-tolerated, and the safety profile was similar to other subcutaneous cohorts. Response rates in this cohort (ORR, 65.0%; ≥VGPR, 57.5%) were consistent with those seen across the five most active doses; responses were durable and deepened over time. Teclistamab exposure was sustained across the dosing interval, with levels exceeding the target exposure derived from the EC90 from an ex vivo cytotoxicity assay (Girgis S, Lin S S X, Pillarisetti K, et al. Translational Approach of Using Ex Vivo Cytotoxicity and Early Clinical Data to Predict Teclistamab Efficacious Therapeutic Range in Multiple Myeloma Patients. Blood 2020;136 (Supplement 1):35).Finally, administration of teclistamab at the RP2D resulted in consistent T-cell activation and cytokine induction. Based on these findings, an international, open-label phase 2 expansion study of teclistamab at the RP2D in patients with RRMM is underway (NCT04557098).

A step-up dosing schedule was employed in multiple cohorts, including patients treated at the RP2D, to mitigate the risk of severe CRS (Blincyto® (blinatumomab) for injection [Prescribing Information]. Amgen Inc., Thousand Oaks, Calif. 2017; Stein A, Franklin J L, Chia V M, et al. Benefit-Risk Assessment of Blinatumomab in the Treatment of Relapsed/Refractory B-Cell Precursor Acute Lymphoblastic Leukemia. Drug Saf 2019; 42:587-601). With this approach, CRS was grade 1/2 and generally occurred during step-up and first full doses of teclistamab. Subcutaneous injection was explored as it requires shorter administration time, is expected to increase convenience for patients and healthcare providers, and may delay CRS due to more gradual absorption. Indeed, serum teclistamab concentrations increased more gradually with subcutaneous versus intravenous administration, and the median time to CRS onset was delayed by one day. The low-grade nature of CRS events suggests that outpatient dosing of teclistamab at the RP2D may be feasible and will be explored in future studies.

Teclistamab showed substantially greater efficacy in this study compared with trials of other novel, approved MM therapies in similar patient populations. Although the subgroup was small in our study, for patients who were triple-class refractory, the ORR was 60.6% with teclistamab at the RP2D compared with 26% for selinexor and 31% for belantamab mafodotin at the approved dose (Chari A, Vogl D T, Gavriatopoulou M, et al. Oral Selinexor-Dexamethasone for Triple-Class Refractory Multiple Myeloma. N Engl J Med 2019; 381:727-38; Lonial S, Lee H C, Badros A, et al. Belantamab mafodotin for relapsed or refractory multiple myeloma (DREAMM-2): a two-arm, randomised, open-label, phase 2 study. Lancet Oncol 2020; 21:207-21). These findings need to be confirmed in a larger patient population; nevertheless, they indicate that teclistamab has encouraging efficacy in patients with RRMM who have exhausted standard treatments and the potential to provide substantial improvement over available therapies. Moreover, teclistamab was well tolerated at the RP2D with no treatment discontinuations due to AEs, whereas selinexor and belantamab mafodotin caused gastrointestinal and ocular toxicities, respectively, that led to treatment discontinuation in a subset of patients.

Teclistamab yielded comparable ORR to other published experimental BCMA-directed immunotherapies, i.e., idecabtagene vicleucel, a CAR-T therapy, and AMG-420, a BiTE (Raje N, Berdeja J, Lin Y, et al. Anti-BCMA CAR T-Cell Therapy bb2121 in Relapsed or Refractory Multiple Myeloma. *N Engl J Med* 2019; 380:1726-37; Topp M S, Duell J, Zugmaier G, et al. Anti-B-Cell Maturation Antigen BiTE Molecule AMG 420 Induces Responses in Multiple Myeloma. *J Clin Oncol* 2020; 38:775-83). The safety profile of teclistamab at the RP2D was favorable compared with idecabtagene vicleucel, with no grade ≥3 CRS (versus 5%) and a low rate of neurotoxicity (2.5% versus 18%). There were no cases of peripheral polyneuropathy, a serious AE observed with AMG-420, following teclistamab treatment. Bispecific antibodies, like teclistamab, have the advantage of ready availability versus CAR-Ts, without the need for collection and production of personalized BCMA-targeting T cells, which delays treatment and may restrict access to patients near large referral centers. Moreover, in contrast with BiTEs, teclistamab is a full-size antibody with a longer half-life (Pillarisetti K, Powers G, Luistro L, et al. Teclistamab is an active T cell-redirecting bispecific antibody against B-cell maturation antigen for multiple myeloma. *Blood Adv* 2020; 4:4538-49), which enables intermittent dosing. In this first report of a full-size bispecific antibody in a robust population of patients with MM, teclistamab showed a favorable efficacy and toxicity profile compared with belantamab mafodotin, the only BCMA-directed agent approved to date, as well as with idecabtagene vicleucel and AMG-420.

In conclusion, this phase 1 study provided evidence that full-size bispecific antibodies can redirect T-cells to MM cells with intermittent subcutaneous dosing and high efficacy. At the weekly 1500 μg/kg subcutaneous dose, teclistamab was well-tolerated, and a substantial proportion of heavily pretreated patients with RRMM achieved a response; responses were durable and deepened over time. Future studies will further evaluate teclistamab in patients with RRMM, in earlier-line MM, as well as in combination with other agents.

Example 4: Phase 1B Dose Escalation/Dose Expansion Study of Daratumumab in Combination with Teclistamab as Treatment for Relapsed or Refractory Multiple Myeloma A Phase 1b, dose escalation/dose expansion, open-label, multicenter, multi-cohort study of daratumumab in combination with teclistamab or another bispecific T cell-redirecting antibody directed toward GPRCSD (talquetamab; also known as JNJ-64407564) to examine the safety, RP2D(s), and preliminary efficacy of the combination is carried out. Adults with multiple myeloma who have received ≥3 prior lines of therapy, including a PI and an IMiD, or who have disease that is double refractory to a PI and an IMiD are enrolled.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

What is claimed:

1. A method of treating relapsed or refractory multiple myeloma in a human subject in need thereof, comprising administering a therapeutically effective amount of a BCMAxCD3 bispecific antibody to the subject to treat the cancer,
wherein the subject is relapsed or refractory to treatment with at least one prior anti-cancer treatment,
wherein the BCMAxCD3 bispecific antibody comprises a BCMA binding domain comprising a heavy chain variable region (VH) having the amino acid sequence of SEQ ID NO: 10 and a light chain variable region (VL) having the amino acid sequence of SEQ ID NO: 11, and a CD3 binding domain comprising a VH having the amino acid sequence of SEQ ID NO: 20 and a VL having the amino acid sequence of SEQ ID NO: 21,
wherein the BCMAxCD3 bispecific antibody is administered subcutaneously at a dose of about 1500 μg/kg weekly, and
wherein the method is effective in treating the multiple myeloma.

2. The method of claim 1, wherein the BCMAxCD3 bispecific antibody is an IgG4 isotype.

3. The method of claim 1, wherein the BCMAxCD3 bispecific antibody comprises a first heavy chain (HC1) having the amino acid sequence of SEQ ID NO: 12, a first light chain (LC1) having the amino acid sequence of SEQ ID NO: 13, a second heavy chain (HC2) having the amino acid sequence of SEQ ID NO: 22, and a second light chain (LC2) having the amino acid sequence of SEQ ID NO: 23.

4. The method of claim 1, wherein the BCMAxCD3 bispecific antibody is teclistamab.

5. The method of claim 1, wherein the BCMAxCD3 bispecific antibody is administered for a time sufficient to achieve complete response, stringent complete response, very good partial response, partial response, minimal response or stable disease status, and can be continued until disease progression or lack of patient benefit.

6. The method of claim 1, wherein the subject is refractory or relapsed to treatment with an anti-CD38 antibody, selinexor, venetoclax, lenalinomide, bortezomib, pomalidomide, carfilzomib, elotozumab, ixazomib, melphalan or thalidomide, or any combination thereof.

7. The method of claim 1, further comprising administering to the subject one or more additional anti-cancer therapies.

8. The method of claim 7, wherein the one or more additional anti-cancer therapies are selected from the group consisting of an autologous stem cell transplant (ASCT), radiation, surgery, a chemotherapeutic agent, a CAR-T therapy, an immunomodulatory agent and a targeted cancer therapy.

9. The method of claim 8, wherein the one or more anti-cancer therapies are selected from the group consisting of selinexor, venetoclax, lenalidomide, thalidomide, pomalidomide, bortezomib, carfilzomib, elotozumab, ixazomib, melphalan, prednisone or dexamethasone, and any combination thereof.

10. The method of claim 1, wherein the treatment achieves an overall response rate of at least 60% in the treated subjects.

11. The method of claim 1, wherein the treatment achieves 15% or more complete response in the treated subjects.

12. The method of claim 1, wherein the subject is relapsed or refractory to treatment with a proteasome inhibitor, an immunomodulatory drug, and an anti-CD38 antibody.

13. The method of claim 1, wherein step-up doses of about 60 μg/kg and about 300 μg/kg are administered to the subject prior to the dose of about 1500 μg/kg weekly.

* * * * *